(12) United States Patent
Gudas et al.

(10) Patent No.: US 7,378,091 B2
(45) Date of Patent: May 27, 2008

(54) ANTIBODIES AGAINST CARBONIC ANHYDRASE IX (CA IX) TUMOR ANTIGEN

(75) Inventors: Jean Gudas, Newark, CA (US); Ian Foltz, Vancouver (CA); Masahisa Handa, El Cerrito, CA (US); Michael L. Gallo, North Vancouver (CA)

(73) Assignee: Amgen Fremont Inc., South San Francisco, CA (US)

( * ) Notice: Subject to any disclaimer, the term of this patent is extended or adjusted under 35 U.S.C. 154(b) by 862 days.

(21) Appl. No.: 10/309,762

(22) Filed: Dec. 2, 2002

(65) Prior Publication Data

US 2004/0018198 A1 Jan. 29, 2004

Related U.S. Application Data

(60) Provisional application No. 60/337,275, filed on Dec. 3, 2001.

(51) Int. Cl.
*A61K 39/395* (2006.01)
*C07K 16/18* (2006.01)
*C07K 16/32* (2006.01)

(52) U.S. Cl. .................. 424/130.1; 424/142.1; 424/146.1; 424/178.1; 424/181.1; 424/183.1; 424/138.1; 530/391.1; 530/388.8; 530/388.21; 530/391.3; 530/391.7

(58) Field of Classification Search ............ None
See application file for complete search history.

(56) References Cited

U.S. PATENT DOCUMENTS 5,387,676 A 2/1995 Zavada et al.

FOREIGN PATENT DOCUMENTS

WO WO 88/08854 11/1988

OTHER PUBLICATIONS

Paul (Fundamental Immunology, (textbook), 1993, pp. 292-293).*
Abstract of Watanabe et al (Kawasaki Igakkaishi, 1997, vol. 23, pp. 241-249).*
Opavsky et al (Genomics, 1996, vol. 33, pp. 480-487).*
Lampman et al (Blood, 1989, vol. 74, pp. 262-269).*
Chrastina, et al., "Biodistribution and pharmacokinetics of $^{125}$I-labeled monoclonal antibody M75 specific for carbonic anhydrase IX, an intrinsic marker of hypoxia, in nude mice xenografted with human colorectal carcinoma", Int. J. Cancer, vol. 105, pp. 873-881, (2003).
Chia, et al., "Prognostic significance of a novel hypoxia-regulated marker, carbonic anhydrase IX, in invasive breast carcinoma", Journal of Clinical Oncology, vol. 19, No. 16, pp. 3660-3668, (Aug. 15, 2001).

Knüppel-Ruppert, et al., "Immunochemical evidence for a unique GPI-anchored carbonic anhydrase isozyme in human cardiomyocytes", American Journal Physiol. Heart Circ. Physiol., vol. 278, pp. H1335-H1344, (2000).
Swinson, et al., "Carbonic anhydrase IX expression, a novel surrogate marker of tumor hypoxia, is associated with a poor prognosis in non-small-cell lung cancer", Journal of Clinical Oncology, vol. 21, No. 3, pp. 473-482, (Feb. 1, 2003).
Vermylen, et al., "Carbonic anhydrase IX antigen differentiates between preneoplastic malignant lesions in non-small cell lung carcinoma", Eur. Respir. Journal, vol. 14, pp. 806-811, (1999).
Wykoff, et al., "Expression of the hypoxia-inducible and tumor-associated carbonic anhydrases in ductal carcinoma in situ of the breast", American Journal of Pathology, vol. 158, No. 3, pp. 1011-1019, (Mar. 2001).
Wykoff, et al., "Hypoxia-inducible expression of tumor-associated carbonic anhydrases", Cancer Research, vol. 60, pp. 7075-7083, (Dec. 15, 2000).
International Search Report dated Sep. 16, 2003, for International Application No. PCT/US02/38550, filed Dec. 2, 2002.
Oosterwijk, et al., Monoclonal Antibody G 250 Recognizes a Determinant Present in Renal-Cell Carcinoma and Absent From Normal Kidney, *Int. J. Cancer*, 38:489-494 (1986).
Oosterwijk, et al., Immunohistochemical Analysis of Monoclonal Antibodies to Renal Antigens, *Am. J. of Pathol*, 123:301-309, (May 1986).
Uemura, et al., MN/CA IX/G250 as a Potential Target for Immunotherapy of Renal Cell Carcinomas, *Br J. Cancer*, 81(4):741-746 (Oct. 1999).
Závada, et al., Human Tumour-Associated Cell Adhesion Protein MN/CA IX: Identification of M75 Epitope and of the Region Mediating Cell Adhesion; *Br. J. Cancer*, 82(11):1808-1813 (2000).
Dijk et al., "Therapeutic Effects of Monoclonal Antibody G250, Interferons and Tumor Necrosis Factor in Mice with Renal-Cell Carcinoma Xenografts," *International Journal of Cancer*, 56: 262-268 (1994).
Steffens et al., "Targeting of Renal Cell Carcinoma with Iodine-131-Labeled Chimeric Monoclonal Antibody G250," *Journal of Clinical Oncology*, 15: 1529-1537 (1997).
Supplementary Partial European Search Report, Application No. EP 02 78 6854, in six (6) pages.

* cited by examiner

*Primary Examiner*—Karen A. Canella
(74) *Attorney, Agent, or Firm*—Knobbe, Martens, Olson & Bear LLP

(57) ABSTRACT

The present invention relates generally to the generation and characterization of anti-CA IX monoclonal antibodies. The invention further relates to the use of such anti-CA IX antibodies in the diagnosis and treatment of disorders associated with increased activity of CA IX, in particular, tumors such as colorectal cancer, renal cell carcinoma (RCC), cervical and other cancers of epithelial origin.

25 Claims, 36 Drawing Sheets

FIGURE 1

Alignment of sequences using VH4-4

```
                        CDR1                                   CDR2
VH4-4        1-QVQLQ ESGPG LVKPS ETLSL TCTVS GGSIS SYYWS WIRQP AGKGL EWIGR IYTSG STNYN 60
MN-21.17.1_HC 1-QVQLQ ESGPG LVKPS ETLSL TCTVS GGSIS SYYWS WIRQP AGKGL EWIGR IYTSG STNYN 60
MN-22.19_HC  1-QVQLQ ESGPG LVKPS ETLSL TCTVS GGSIS FYYWN WIRQP AGKGL EWVGR IYTSG STNYN 60
MN-22.29_HC  1-QVQLQ ESGPG LVKPS ETLSL TCTVS GGSIS SYYWS WIRQP AGKGL EWIGR IYTSG STNYN 60
MN-22.3_HC   1-QVQLQ ESGPG LVKPS ETLSL TCTVS GGSIS SNYWS WIRQP AGKGL EWIGR IYTSG STNYN 60
MN-22.5_HC   1-QVQLQ ESGPG LVKPS ETLSL TCTVS GGSIS FYYWN WIRQP AGKGL EWVGR IYTSG STNYN 60

CDR2                                                      CDR3
VH4-4        61-PSLKS RVTMS VDTSK NQFSL KLSSV TAADT AVYYC AR--- ----- ----- ----- -  97 (SEQ ID NO:1)
MN-21.17.1_HC 61-PSLKS RVTMS VDTSK NQFSL KLSSV TAADT AVYYC ARDG- -QWLE DYGMD VWGQG TTVTV SS 119 (SEQ ID NO:2)
MN-22.19_HC  61-PSLKS RVTMS VDTSK NQFSL KLSSV TAADT AVYYC ARGGF LEWDY YYGMD VWGQG TTVTV SS 122 (SEQ ID NO:3)
MN-22.29_HC  61-PSLKS RVTMS VDTSK NQFSL KLSSV TAADT AVYYC ARDG- -QWLE DYGMD VWGQG TTVTV SS 119 (SEQ ID NO:4)
MN-22.3_HC   61-PSLKS RVTMS VDTSK NQFSL KLSSV TAADT AVYYC ARDQ- -GFLE WLPLD VWGQG TTVTV SS 119 (SEQ ID NO:5)
MN-22.5_HC   61-PSLKS RVTMS VDTSK NQFSL KLSSV TAADT AVYYC ARGGF LEWDY YYGMD VWGQG TTVTV SS 122 (SEQ ID NO:6)
```

FIGURE 3A

Alignment of sequences using VH4-31

```
                              CDR1                                              CDR2
VH4-31        1-QVQLQ ESGPG LVKPS QTLSL TCTVS GGSIS SGGYY WSWIR QHPGK GLEWI GYIYY SGSTY 60
MN-21.2.1_HC  1-QVQLQ ESGPG LVKPS QTLSL TCTVS GGSIS SGGYY WNWIR QHPGK GLEWI GYIYY SGSTY 60
MN-21.5.2_HC  1-QVQLE QSGPG LVKPS QTLSL TCTVS GGSIS SGGRY WSWIR QHPGK GLEWI GYIYY SGSTY 60
MN-21.6.1_HC  1-QVQLQ ESGPG LVKPS QTLSL TCTVS GGSIS SGGYY WSWIR QHPGK GLEWI GYIYY SGSTY 60
MN-21.7.1_HC  1-QVQLQ ESGPG LVKPS QTLSL TCTVS GGSIS SGGYY WSWIR QHPGK GLEWI GYIYY SGNTY 60
MN-21.9.1_HC  1-QVQLQ ESGPG LVKPS QTLSL TCTVS GGSIS SGGYY WSWIR QHPGK GLEWI GYIYY SGNTY 60
MN-22.11_HC   1-QVQLQ ESGPG LVKPS QTLSL TCTVS GGSIS SGGYY WSWIR QHPGK GLEWI GYIYY SGSTY 60
MN-22.15_HC   1-QVQLQ ESGPG LVKPS QTLSL TCTVS GGSIS SGGYY WSWIR QHPGK GLEWI GYIYY SGYTY 60
MN-22.16_HC   1-QVQLQ ESGPG LVKPS QTLSL TCTVS GGSIS SGVYY WSWIR QHPGK GLEWI GYIYY SRSTY 60
MN-22.18_HC   1-QVQLQ ESGPG LVKPS QTLSL TCTVS GGSIS SGGYY WNWIR QHPGK GLEWI GYIYY SGSTY 60
MN-22.21_HC   1-QVQLQ ESGPG LVKPS QTLAL TCTVS GGSIS SGGYY WSWIR QHPGK GLEWI GYIYY SGYTY 60
MN-22.23_HC   1-QVQLQ ESGPG LVKPS QTLSL TCTVS GGSIN SGGYY WSWIR QHPGK GLEWI GYIYY SGSTY 60
MN-22.9_HC    1-QVQLQ ESGPG LVKPS QTLSL TCTVS GGSIN SGGYY WSWIR QHPGK GLEWI GYIYY SGSTY 60

CDR2                                              CDR3
VH4-31        61-YNPSL KSRVT ISVDT SKNQF SLKLS SVTAA DTAVY YCAR- ----- ----- ----- ----- 99
MN-21.2.1_HC  61-YNPSL KSRVT ISVDT SKNQF SLKLS SVTAA DTAVY YCART YYD-- ILTGY PDAFD IWGQG 118
MN-21.5.2_HC  61-YNPSL ISIDT SKNQF SLKLS SVTAA DTAVY YCARA GTYYG ----S GSYLD YWGQG 116
MN-21.6.1_HC  61-YNPSL KSRVT ISVDT SKNQF SLKLS SVTAA DTAVY YCARA GKYYG ----S GSYLD YWGQG 116
MN-21.7.1_HC  61-YNPSL KSRIT ISVDT SKNQF SLKLS SVTAA DTAVY YCART YYD-- FLTGY PDAFD IWGQG 118
MN-21.9.1_HC  61-YNPSL KSRVT ISVDT SKNQF SLKLS SVTAA DTAVY YCARV L---- LWFGE DYGVD VWGQG 116
MN-22.11_HC   61-YNPSL KSRVT ISVDT SKNQF SLKLS SVTAA DTAVY YCARD GYNY- ----- -WYFD LWGRG 113
MN-22.15_HC   61-YNPSL KSRVT ISVDT SKNQF SLKLS SVTAA DTAVY YCARD RYYDI LTGYY NYGMD YFGMD VWGQG 120
MN-22.16_HC   61-YNPSL KSRVT ISVDT SKNQF SLKLS SVTAA DTAVY YCARG N---- -AHDY YFGMD VWGQG 115
MN-22.18_HC   61-YNPSL KSRVT ISVDT SKNQF SLKLS SVTAA DTAVY YCART YYD-- ILTGY PDAFD IWGQG 118
MN-22.21_HC   61-YNPSL KSRVT ISVDT SKNQF SLKLS SVTAA DTAVY YCARE T---- VTDYY YYGMD VWGQG 116
MN-22.23_HC   61-YNPSL KSRVI ISVDT SENQF SLKLS SVTAA DTAVY YCARE R---- VTDYY YYGLD VWGQG 116
MN-22.9_HC    61-YNPSL KSRVI ISVDT SKNQF SLKLS SVTAA DTAVY YCARE R---- VTDYY YYGLD VWGQG 116
```

FIGURE 3B

```
VH4-31         ------                        99  (SEQ ID NO:7)
MN-21.2.1_HC   119-TMVTVS S                 125  (SEQ ID NO:8)
MN-21.5.2_HC   117-TLVTVS S                 123  (SEQ ID NO:9)
MN-21.6.1_HC   117-TLVTVS S                 123  (SEQ ID NO:10)
MN-21.7.1_HC   119-TMVTVS S                 125  (SEQ ID NO:11)
MN-21.9.1_HC   117-TTVTVS S                 123  (SEQ ID NO:12)
MN-22.11_HC    114-TLVTVS S                 120  (SEQ ID NO:13)
MN-22.15_HC    121-TTVTVS S                 127  (SEQ ID NO:14)
MN-22.16_HC    116-TTVTVS S                 122  (SEQ ID NO:15)
MN-22.18_HC    119-TMVTVS S                 125  (SEQ ID NO:16)
MN-22.21_HC    117-TTVTVS S                 123  (SEQ ID NO:17)
MN-22.23_HC    117-TTVTVS S                 123  (SEQ ID NO:18)
MN-22.9_HC     117-TTVTVS S                 123  (SEQ ID NO:19)
```

FIGURE 5

Alignment of sequences using VH4-39

```
                        CDR1
VH4-39         1-QIQLQ ESGPG LVKPS ETLSL TCTVS GGSIS SSSYY WGWIR QPPGK GLEWI GSIYY SGST 59
MN-21.10.1_HC  1---QLE QSGPG LVKPS ETLSL TCTVS DGSIS SSSYY WGWIR QPPGK GLEWI GSIYY SGST 57
MN-22.25_HC    1-QIQLQ ESGPG LVKPS ETLSL TCTVS DGSIS SSSYY WGWIR QPPGK GLEWI GSIYY SGST 59

CDR2                                                    CDR3
VH4-39         60-YYNPS LKSRV TISVD TSKNQ FSLKL SSVTA ADTAV YYCAR ----- ----- ---   99  (SEQ ID NO:20)
MN-21.10.1_HC  58-YYNPS LKSRV TISVD TSKNQ FSLKL SSVTA ADTAV YYCAR HGSFF DYWGQ GTLVT VSS 115 (SEQ ID NO:21)
MN-22.25_HC    60-YYNPS LKSRV TISVD TSKNQ FSLKL SSVTA ADTAV YYCAR HGSFF DYWGQ GTLVT VSS 117 (SEQ ID NO:22)
```

FIGURE 6

Alignment of sequences using VH4-59

```
                                                   CDR1                              CDR2
                                                   _____                       _____
VH4-59           1-QVQLQ ESGPG LVKPS ETLSL TCTVS GGSIS SYYWS WIRQP PGKGL EWIGY IYYSG STNY 59
MN-21.1.1_HC     1-QVQLQ ESGPG LVKPS ETLSL TCTVS GGSIS SYYWS WIRQP PGKGL EWIGY IYYSG STNY 59
MN-21.14.1_HC    1-QVQLQ ESGPG LVKPS ETLSL TCTVS GGSIS SYYWS WIRQP PGKGL EWIGY IYYSG STNY 59
MN-22.12_HC      1-QVQLQ ESGPG LVKPS ETLSL TCTVS GGSIS SYYWS WIRQP PGKGL EWIGY IYSSG STNY 59
MN-22.17_HC      1-QVQLQ ESGPG LVKPS ETLSL TCTVS GGSIS SYYWS WIRQP PGKGL EWIGY IYYSG STNY 59
MN-22.26_HC      1-QVQLQ ESGPG LVKPS ETLSL TCTVS GGSIS RNYWS WIRQP PGKGL EWIGY IYYSG STKY 59
MN-22.27_HC      1-QVQLQ ESGPG LVKPS ETLSL TCTVS GGSIS SYYWS WIRQP PGKGL EWIGY IYYSG STNY 59
MN-22.8.1_HC     1------ -SGPG LVKPS ETLSL TCTVS GGSIS SYYWS WIRQP PGKGL EWIGY IYYSG STNY 53

CDR2                                                        CDR3
                 _____                                                     _____
VH4-59           60-NPSLK SRVTI SVDTS KNQFS LKLSS VTAAD TAVYY CAR-- ----- -----  -----  ----- 97
MN-21.1.1_HC     60-NPSLK SRVTI SVDTS KNQFS LKLSS VTAAD TAVYY CARRG YDILT GYDY-  -FDYW  GQGTL 117
MN-21.14.1_HC    60-NPSLK SRVTI SVDTS KNQFS LKLSS VTAAD TAVYY CARRG YDFLT GYDY-  -FDYW  GQGTL 117
MN-22.12_HC      60-NPSLK SRVTI SVDTS KNQFS LKLSS VTAAD TAVYY CARDQ HSSSF YYYYY  GMDVW  GQGTT 119
MN-22.17_HC      60-NPSLK SRVTI SVDTS KNQFS LKLSS VTAAD TAVYY CARRG YDILT GYDY-  -FDYW  GQGTL 117
MN-22.26_HC      60-NPSLK SRVTI SVDTS KNQFS LKLSS VTAAD TAVYY CARSY YDFLT GYYHV  -FDYW  GQGTL 118
MN-22.27_HC      60-NPSLK SRVTI SVDTS KNQFS LKLSS VTAAD TAVYY CARRG YDFLT GYDY-  -FDYW  GQGTL 117
MN-22.8.1_HC     54-NPSLK SRVTI SVDTS KNQFS LKLTS VTAAD TAVYY CARDQ HSSSV YYYYY  GMDVW  GQGTT 113

VH4-59            97------         (SEQ ID NO:23)
MN-21.1.1_HC     118-VTVSS    122  (SEQ ID NO:24)
MN-21.14.1_HC    118-VTVSS    122  (SEQ ID NO:25)
MN-22.12_HC      120-VTVSS    124  (SEQ ID NO:26)
MN-22.17_HC      118-VTVSS    122  (SEQ ID NO:27)
MN-22.26_HC      119-VTVSS    123  (SEQ ID NO:28)
MN-22.27_HC      118-VTVSS    122  (SEQ ID NO:29)
MN-22.8.1_HC     114-VTVSSA   119  (SEQ ID NO:30)
```

Dendrogram:

FIGURE 8

Alignment of sequences using VK-A19

```
                           CDR1
                           ―――――――――――――――――――――――――
A19         1-DIVMT QSPLS LPVTP GEPAS ISCRS SQSLL HSNGY NYLDW YLQKP GQSPQ LLIYL GSNRA  60
MN-21.5.2_LC 1-DIVMT QSPLS LPVTP GEPAS ISCRS SQSLL HSNGY NYLDW YLQKP GQCPQ LLIYL GSNRA  60
MN-21.6.1_LC 1-DIVMT QSPLS LPVTP GEPAS ISCRS SQSLL HSNGY NYLDW YLQKP GQSPQ LLIYL GSNRA  60
MN-22.7_LC   1-DIVMT QSPLS LPVTP GEPAS ISCRS SQSLL YSNGY NYLDW YLQKP GQSPQ FLIYL GSNRA  60
                                                                      CDR2

CDR2                                 CDR3
             ―――――――――――――                            ――――――――――
A19         61-SGVPD RFSGS GSGTD FTLKI SRVEA EDVGV YYCMQ ALQTP ----- -----  --  100 (SEQ ID NO:31)
MN-21.5.2_LC 61-SGVPD RFSGS GSGTD FTLKI SRVEA EDVGV YYCMQ ALQTP LTFGG GTKVE IK  112 (SEQ ID NO:32)
MN-21.6.1_LC 61-SGVPD RFSGS GSGTD FTLKI SRVEA EDVGV YYCMQ ALQTP LTFGG GTKVE IK  112 (SEQ ID NO:33)
MN-22.7_LC   61-SGVPD RFSGS GSGTD FTLKI SRVEA EDVGV YYCMQ ALQTP RSFGQ GTKLE IK  112 (SEQ ID NO:34)
```

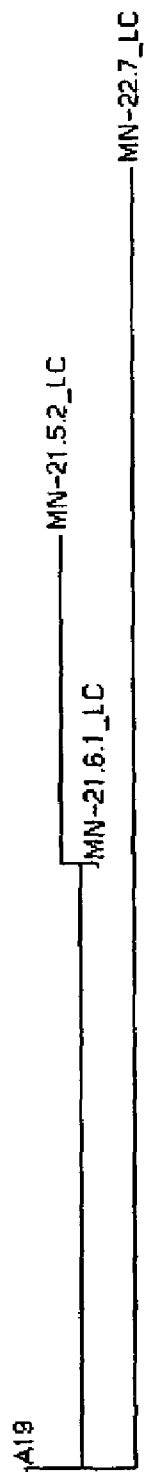

FIGURE 10

Alignment of sequences using VK-A27

```
                        CDR1                                                      CDR2
             _____                                            _____
A27          1-EIVLT QSPGT LSLSP GERAT LSCRA SQSVS SSYLA WYQQK PGQAP RLLIY GASSR ATGIP 60
MN-22.8.1_LC 1-ETQLT QSPGT LSLSP GERAT LSCRA SQSIY INYLA WYQQK PGQAP RLLIS GASSR ATGIP 60
MN-21.17.1_LC 1-EIVLT QSPGT LSLSP GERAT LSCWA SQSVF SNYLA WYQQK PGQAP RLLIY GASSR ATGIP 60
MN-21.8.1_LC 1-EIVLT QSPGT LSLSP GERAT LSCRA SQSVS SSYLA WYQQK PGQAP RLLIY GASSR ATGIP 60
MN-22.11_LC  1-EIVLT QSPGT LSLSP GERAT LSCRA SQSVG SSYLA WYQQK PGQTP RLLIY GASSR ATGIP 60
MN-22.19_LC  1-EIVLT QSPGT LSLSP GERAT LSCRA SQSVS VTYLA WYQQK PGQAP RLLIY GASSR ATGIP 60
MN-22.26_LC  1-EIVLT QSPGT LSLSP GERAT LSCRA SQSVY SNYFA WYQQK PGQAP RLLIY GASSR AAGIP 60
MN-22.27_LC  1-EIVLT QSPGT LSLSP GERAT LSCWA SQSVF SNYLA WYQQK PGQAP RLLIY GASSR ATGIP 60
MN-22.3_LC   1-EIVLT QSPGT LSLSP GERAT LSCRA SQSVS SSYLA WYQQK PGQAP RLLIY GASSR ATGIP 60
MN-22.4_LC   1-EIVLT QSPGT LSLSP GERAT LSCRA SQSVS VTYLA WYQQK PGQAP RLLIY GASSR ATGIP 60
MN-22.5_LC   1-EIVLT QSPGT LSLSP GERAT LSCRA SQSVY SNYFA WYQQK PGQAP RLLIY GASSR AAGIP 60
MN-22.9_LC   1-EIVLT QSPGT LSLSP GERAT LSCRA SQSVY SNYFA WYQQK PGQAP RLLIY GASSR AAGIP 60

CDR3
                                             _____
A27          61-DRFSG SGSGT DFTLT ISRLE PEDFA VYYCQ QYGSS P---- ----- ----- 96  (SEQ ID NO:35)
MN-22.8.1_LC 61-DRFSG SGSGT DFTLT ISRLE PEDFA VYYCQ QYGRS L--TF GGGTE VEIKR 108 (SEQ ID NO:36)
MN-21.17.1_LC 61-DRFSG SGSGT DFPLT ISRLE PEDFA VYYCQ QYGSS P-LIF GGGTK VEIK  108 (SEQ ID NO:37)
MN-21.8.1_LC 61-DRFSG SGSGT DFTLT ISRLE PEDFA VYSCQ QYGSS L--TF GGGTK VEIK  107 (SEQ ID NO:38)
MN-22.11_LC  61-DRFSG SGSGT DFTLT ISRLE PEDFA VYYCQ QYGFS P-LIF GGGTK VEIK  108 (SEQ ID NO:39)
MN-22.19_LC  61-DRFSG SGSGT DFTLT ISRLE PEDFA VYYCQ QYGSS V--TF GGGTK VEIK  107 (SEQ ID NO:40)
MN-22.26_LC 61-DRFSG SGSGT DFTLT ISRLE PEDFA VYYCQ QYGTS PRFSF GQGTK LEIK  109 (SEQ ID NO:41)
MN-22.27_LC 61-DRFSG SGSGT DFPLT ISRLE PEDFA VYYCQ QYGSS P-LIF GGGTK VEIK  108 (SEQ ID NO:42)
MN-22.3_LC  61-DRFSG SGSGT DFTLT ISRLE PEDFA VYYCQ QYGTS P-LIF GQGTR LEIK  108 (SEQ ID NO:43)
MN-22.4_LC  61-DRFSG SGSGT DFTLT ISRLE PEDFA VYSCQ QYGSS L--TF GGGTK VEIK  107 (SEQ ID NO:44)
MN-22.5_LC  61-DRFSG SGSGT DFTLT ISRLE PEDFA VYYCQ QYGSS V--TF GGGTK VEIK  107 (SEQ ID NO:45)
MN-22.9_LC  61-DRFSG SGSGT DFTLT ISRLE PEDFA VYYCQ QYGTS PRFSF GQGTK LEIK  109 (SEQ ID NO:46)
```

FIGURE 12

Alignment of sequences using VK-A30

|              | CDR1 | | | | CDR2 | |
|---|---|---|---|---|---|---|

```
                       CDR1                                    CDR2
                       ‾‾‾‾                                    ‾‾‾‾
A30         1-DIQMT QSPSS LSASV GDRVT ITCRA SQGIR NDLGW YQQKP GKAPK RLIYA ASSLQ SGVPS 60
MN-21.2.1_LC  1-DIQMT QSPSS LSASV GDRVT ITCRA SQDIR NDLGW YQQKP GKAPK RLICA ASSLQ SGVPS 60
MN-21.7.1_LC  1-DIQMT QSPSS LSASV GDRVT ITCRA SQAIR NDLGW YQQKP GKAPK RLIYA ASSLQ SGVPS 60
MN-22.10_LC   1-DIQMT QSPSS LSASV GDRVT ITCRA SQGIR YDLGW YQQKP GKAPK RLIYA TSNLQ SGVPS 60
MN-22.14_LC   1-DIQMT QSPSS LSASV GDRVT ITCRA SQGIR NDLGW YQQKP GKAPK RLIYA ASSLQ SGVPS 60
MN-22.18_LC   1-DIQMT QSPSS LSASV GDRVT ITCRA SQGIR NDLGW YQQKP GKAPK RLICA ASSLQ SGVPS 60
MN-22.20_LC   1-DIQMT QSPSS LSASV GDRVT ITCRA SQGIR NDLGW YQQKP GKAPK RLIYA ASSLQ SGVPS 60
MN-22.21_LC   1-DIQMT QSPSS LSASV GDRVT ITCRA SQAIR NDLGW YQQKP GKAPK RLIYA ASSLQ SGVPS 60
MN-22.24_LC   1-DIQMT QSPSS LSASV GDRVT ITCRA SQGIR YDLGW YQQKP GKAPK RLIYA ASSLQ SGVPS 60
MN-22.25_LC   1-DIQMT QSPSS LSASV GDRVT ITCRA SQGIR NDLGW YQQKP GKAPK RLIYA TSNLQ SGVPS 60
MN-22.28.1_LC 1-DIRLT QSPSS LSASV GDRVT ITCRA SQGIR NDLGW YQQKP GKAPK RLIYA ASSLQ SGVPS 60
MN-22.30_LC   1-DIQMT QSPSS LSASV GDRVT ITCRA SQGIR NDLGW YQQKP GKAPK RLIYA ASSLQ SGVPS 60

CDR3
                           ‾‾‾‾
A30         61-RFSGSG SGTEF TLTIS SLQPE DFATY YCLQH NSYP- ----- TFGQG TKVEI -  94 (SEQ ID NO:47)
MN-21.2.1_LC  61-RFSGSG SGTEF TLTIS SLQPE DFATY YCLQH NSYPW TFGQG TKVEI K 107 (SEQ ID NO:48)
MN-21.7.1_LC  61-RFSGSG SGSEF TLTIS SLQPE DFATY YCLQY HSYPW TFGPG TKVEI K 107 (SEQ ID NO:49)
MN-22.10_LC   61-RFSGSG SGTEF TLTIS SLQPE DFATY YCLQH NSYPP TFGPG TKVDI K 107 (SEQ ID NO:50)
MN-22.14_LC   61-RFSGSG SGTEF TLTIS SLQPE DFATY YCLQH NSYPL TFGGG TKVEI K 107 (SEQ ID NO:51)
MN-22.18_LC   61-RFSGSG SGTEF TLTIS SLQPE DFATY YCLQH NSYPW TFGQG TKVEI K 107 (SEQ ID NO:52)
MN-22.20_LC   61-RFSGSG SGTEF TLTIS SLQPE DFTTY YCLQY KSYPW TFGQG TKVEI K 107 (SEQ ID NO:53)
MN-22.21_LC   61-RFSGSG SGSEF TLTIS SLQPE DFATY YCLQY HSYPW TFGQG TKVDI K 107 (SEQ ID NO:54)
MN-22.24_LC   61-RFSGSG SGTEF TLTIS SLQPE DFATY YCLQH NSYPP TFGPG TKVEI K 107 (SEQ ID NO:55)
MN-22.25_LC   61-RFSGSG SGTEF TLTIS SLQPE DFTTY YCLQY KSYPW TFGGG TKVEI K 107 (SEQ ID NO:56)
MN-22.28.1_LC 61-RFSGSG SGTEF TLTIS SLQPE DFATY YCLQH NSYPL TFGGG TKVEI K 107 (SEQ ID NO:57)
MN-22.30_LC   61-RFSGSG SGTDF TLTIS SLQPE DFATY YCLQH YSYPL TFGGG TKVEI K 107 (SEQ ID NO:58)
```

Dendrogram:

FIGURE 14

Alignment of sequences using VK-L5

```
                              CDR1                                                    CDR2
                              _____                                             _____
L5            1-DIQMT QSPSS VSASV GDRVT ITCRA SQGIS SWLAW YQQKP GKAPK LLIYA ASSLQ SGVPS  60
MN-21.1.1_LC  1-DIQMT QSPSS VSASV GDRVT ITCRA SQGIS IWLTW YQQKP GKAPK LLIYA ASSLQ SGVPS  60
MN-21.14.1_LC 1-DIQMT QSPSS VSASV GDRVT ITCRA SQGIS SWLAW FQQKP GKAPK LLIYA ASSLQ SGVPS  60
MN-22.12_LC   1-DIQMT QSPSS VSASV GDRVT ITCRA SQGIS SWLAW YQQKP GKAPK LLIYA ASSLQ SGVPS  60
MN-22.17_LC   1-DIQMT QSPSS VSASV GDRVT ITCRA SQGIS IWLTW YQQKP GKAPK LLIYA ASSLQ SGVPS  60
MN-22.29_LC   1-DIQMT QSPSS VSASV GDRVT ITCRA SQGIS SWLAW FQQKP GKAPK LLIYA ASSLQ SGVPS  60

CDR3
                                               _____
L5            61-RFSGS GSGTD FTLTI SSLQP EDFAT YYCQQ ANSFP ----- -----  ----- --  95 (SEQ ID NO:59)
MN-21.1.1_LC  61-RFSGS GSGTD FTLTI SSLQP EDFAT YYCQQ ANSFP ITFGQ GTRLE IK 107 (SEQ ID NO:60)
MN-21.14.1_LC 61-RFSGS GSGTD FTLTI SSLQP EDFAT YYCQQ ANSFP ITFGQ GTRLE IK 107 (SEQ ID NO:61)
MN-22.12_LC   61-RFSGS GSGTD FTLTI SSLQP EDFAT YYCQQ ANSFP LTFGP GTKVD IK 107 (SEQ ID NO:62)
MN-22.17_LC   61-RFSGS GSGTD FTLTI SSLQP EDFAT YYCQQ ANSFP ITFGP GTKVD IK 107 (SEQ ID NO:63)
MN-22.29_LC   61-RFSGS GSGTD FTLTI SSLQP EDFAT YYCQQ ANSFP ITFGQ GTRLE IK 107 (SEQ ID NO:64)
```

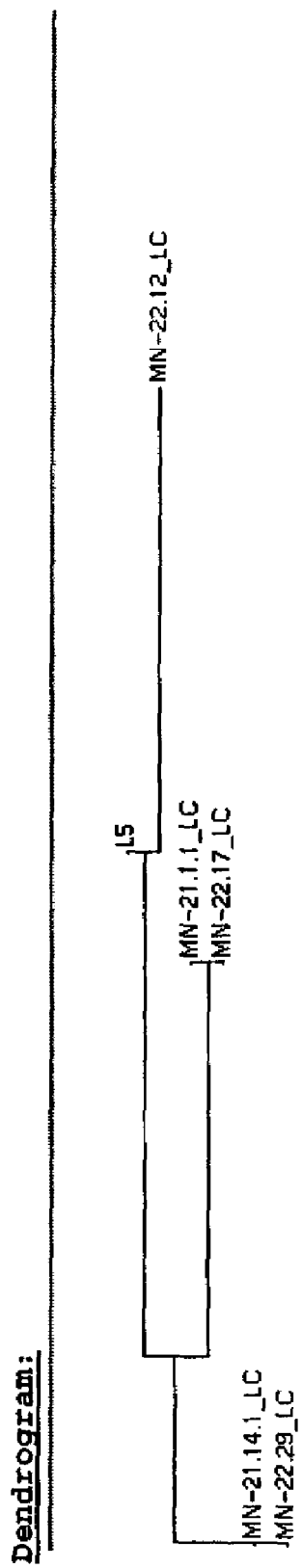

FIGURE 16

Alignment of sequences using VK-O12

```
                              CDR1                                          CDR2

O12          1-DIQMT QSPSS LSASV GDRVT ITCRA SQSIS SYLNW YQQKP GKAPK LLIYA ASSLQ SGVPS 60
MN-21.9.1_LC 1-DIQMT QSPSS LSASV GDRVT ITCRA SQSIT NYLNW YQQKP GKAPK LLIYA ASSLQ SGVPS 60
MN-22.15_LC  1-DIQMT QSPSS LSASV GDRVT ITCRA SQSIS SYLNW YQQKP GKVPK LLIYV ASSLQ SGVPS 60
MN-22.16_LC  1-DIQMT QSPSS LSASV GDRVT ITCRA SQSIS SYLNW YQQKP GKVPK LLIYV ASSLQ SGVPS 60
MN-22.23_LC  1-DIQMT QSPSS LSASV GDRVT ITCRA SQSIT NYLNW YQQKP GKAPK LLIYA ASSLQ SGVPS 60

CDR3
O12          61-RFSGS GSGTD FTLTI SSLQP EDFAT YYCQQ SYSTP ----- -----  -- 95  (SEQ ID NO:65)
MN-21.9.1_LC 61-RFSGS GSGTD FTLTI SSLQP EDFAT YYCQQ SYITP LTFGG GTEVE IK 107  (SEQ ID NO:66)
MN-22.15_LC  61-RFSGS GSGTD FTLTI SSLQP EDFAT YYCQQ SYSTP LTFGG GTKVE IK 107  (SEQ ID NO:67)
MN-22.16_LC  61-RFSGS GSGTD FTLTI SSLQP EDFAT YYCQQ SYSTP LTFGG GTKVE IK 107  (SEQ ID NO:68)
MN-22.23_LC  61-RFSGS GSGTD FTLTI SSLQP EDFAT YYCQQ SYITP LTFGG GTEVE IK 107  (SEQ ID NO:69)
```

Dendrogram:

FIGURE 18

| Well | Single Cell | Vgamma/D/J | FR1 | CDR1 | FR2 | CDR2 |
|---|---|---|---|---|---|---|
| - | - | Germline | QVQLQESGPGLVKPSETLSLTCTVSGGSIS | SYYWS | WIRQPPGKGLEWIG | YIYYSGSTNYNPSLKS |
| 43G10 | 80 | VH4-59/D3-3/JH6b | ---------------------------- | ----- | -------------- | ---------------- |
| 44D2 | 141 | | ------------S--------------- | ----- | -------------- | ---------------- |
| 41D1 | 174 | | ---------------------------- | ----- | -------------- | --F------------- |
| - | - | Germline | QVQLQESGPGLVKPSQTLSLTCTVSGGSIS | SGGYYWS | WIRQHPGKGLEWIG | YIYYSGSTYYNPSLKS |
| 45C9 | 23 | VH4-30.1/D3-9/JH5b | ---------------------------- | ------- | -------------- | ---------------- |
| - | - | Germline | EVQLVESGGGLVKPGGSLRLSCAASGFTFS | SYSMN | WVRQAPGKGLEWVS | SISSSSSYIYYADSVKG |
| 49C8 | 51 | VH3-21/D5-18/JH4b | -----F---------------------- | --FR-- | --------E----- | ---T------------ |
| - | - | Germline | QVQLQESGPGLVKPSETLSLTCTVSGGSIS | SYYWS | WIRQPAGKGLEWIG | RIYTSGSTNYNPSLKS |
| 42E4 | 109 | VH4-04/D1-20/JH6b | ---------------------------- | ----- | -------------- | ---------------- |

| Well | Single Cell | Vgamma/D/J | FR3 | CDR3 | FR4 | |
|---|---|---|---|---|---|---|
| - | - | Germline | RVTISVDTSKNQFSLKLSSVTAADTAVYYCAR | | WGQGTLVTVSS | SEQ ID NO: 70 |
| 43G10 | 80 | VH4-59/D3-3/JH6b | ------------------------------- | DTRTIFGVVSGMDV | ----------- | SEQ ID NO: 71 |
| 44D2 | 141 | | ---------N-H------------------- | DTRTIFGVVSGMDV | ----------- | SEQ ID NO: 72 |
| 41D1 | 174 | | ------------------------------- | DTRTIFGVVSGMDV | ----------- | SEQ ID NO: 73 |
| - | - | Germline | RVTISVDTSKNQFSLKLSSVTAADTAVYYCAR | | WGQGTLVTVSS | SEQ ID NO: 74 |
| 45C9 | 23 | VH4-30.1/D3-9/JH5b | ------------------------------- | ENYDILTGFNWFDP | ----------- | SEQ ID NO: 75 |
| - | - | Germline | RFTISRDNAKNSLYLQMNSLRAEDTAVYYCAR | | WGQGTLVTVSS | SEQ ID NO: 76 |
| 49C8 | 51 | VH3-21/D5-18/JH4b | ------------------------------- | FTAMALDY | ----------- | SEQ ID NO: 77 |
| - | - | Germline | RVTMSVDTSKNQFSLKLSSVTAADTAVYYCAR | | WGQGTLVTVSS | SEQ ID NO: 78 |
| 42E4 | 109 | VH4-04/D1-20/JH6b | ------------------------------- | LITGPYGMDV | ----------- | SEQ ID NO: 79 |

FIGURE 19

| Well | Single Cell | Vkappa/J | FR1 | CDR1 | FR2 | CDR2 |
|---|---|---|---|---|---|---|
| - | - | Germline | EIVLTQSPGTLSLSPGERATLSC | RASQSVSSSYLA | WYQQKPGQAPRLLIY | GASSRAT |
| 43G10 | 80 | A27/JK4 | --------------------- | -----Y------ | --------------- | -----P- |
| 44D2 | 141 | | --------------------- | -T--T-Y-T--- | --------------- | ------- |
| 41D1 | 174 | | --------------------- | -----Y------ | --------------- | ------- |
| - | - | Germline | DIQMTQSPSSVSASVGDRVTITC | RASQGISSWLA | WYQQKPGKAPKLLIY | AASSLQS |
| 45C9 | 23 | L19/JK1 | --------------------- | ------------ | -------V------- | ST-R--- |
| - | - | Germline | DIQMTQSPSSLSASVGDRVTITC | RASQGISNYLA | WYQQKPGKVPKLLIY | AASTLQS |
| 49C8 | 51 | A20/JK1 | --------------------- | ------F----- | --------------- | ------- |
| - | - | Germline | DIQMTQSPSSLSASVGDRVTITC | RASQSISSYLN | WYQQKPGKAPKLLIY | AASSLQS |
| 42E4 | 109 | O2/JK3 | --------------------- | ------------ | --------------- | T-N-RG |

| Well | Single Cell | Vkappa/J | FR3 | CDR3 | FR4 | |
|---|---|---|---|---|---|---|
| - | - | Germline | GIPDRFSGSGSGTDFTLTISRLEPEDFAVYYC | QQYGSSLT | FGGGTKVEIK | SEQ ID NO: 80 |
| 43G10 | 80 | A27/JK4 | ------------------------------- | --H--R-- | ---------- | SEQ ID NO: 81 |
| 44D2 | 141 | | ------------------------------- | --H--R-- | ---------- | SEQ ID NO: 82 |
| 41D1 | 174 | | --------------F---------------- | --H--R-- | ---------- | SEQ ID NO: 83 |
| - | - | Germline | GVPSRFSGSGSGTDFTLTISSLQPEDFATYYC | QQANSFWT | FGQGTKVEIK | SEQ ID NO: 84 |
| 45C9 | 23 | L19/JK1 | -----------------D------------- | ---D-R-- | ---------- | SEQ ID NO: 85 |
| - | - | Germline | GVPSRFSGSGSGTDFTLTISSLQPEDVATYYC | QKYNSAPWT | FGQGTKVEIK | SEQ ID NO: 86 |
| 49C8 | 51 | A20/JK1 | --------------------------V---- | L------- | ---------- | SEQ ID NO: 87 |
| - | - | Germline | GVPSRFSGSGSGTDFTLTISSLQPEDFATYYC | QQSYSTPFT | FGPGTKVDIK | SEQ ID NO: 88 |
| 42E4 | 109 | O2/JK3 | -----------------G------------- | ------SI- | ---------- | SEQ ID NO: 89 |

FIGURE 26A

| Chain Name | V | D | J | FR1 | CDR1 | FR2 | CDR2 |
|---|---|---|---|---|---|---|---|
| | | Germline | | QVQLVQSGAEVKKPGASVKVSCKAS | GYTFTGYYMH | WVRQAPGQGLEWMG | WINPNSGGTNYAQKFQG |
| AX014H21_8_1N1G2 | VH1-2 | D2-27 | JH6b | ---------------------- | ---------- | -------------- | ---------------- |
| | | Germline | | QVQLQESGPGLVKPSETLSLTCTVS | GGSISSYYWS | WIRQPAGKGLEWIG | RIYTSGSTNYNPSLKS |
| AX014H22_5N1G2 | VH4-4 | D3-3 | JH6b | ---------------------- | -F----N--- | -------------- | ----V----------- |
| AX014H22_19N1G2 | " | " | " | ---------------------- | -F----N--- | -------------- | ----V----------- |
| AX014H22_3N1G2 | " | " | " | ---------------------- | ------N--- | -------------- | ---------------- |
| | | Germline | | QVQLQESGPGLVKPSETLSLTCTVS | GGSVSSGGYYWS | WIRQPPGKGLEWIG | YIYYSGSTNYNPSLKS |
| AX014H22_14N1G2 | VH4-61 | D3-10 | JH4b | ---------------------- | ----I------ | -------------- | --------S------- |
| | | Germline | | EVQLLESGGGLVQPGGSLRLSCAAS | GFTFSSYAMS | WVRQAPGKGLEWVS | AISGSGGSTYYADSVKG |
| AX014H22_28_1N1G2 | VH3-23 | D1-26 | JH6b | Q---EQ----------------- | ---------- | -------------- | -----------G----- |
| | | Germline | | QVQLQESGPGLVKPSQTLSLTCTVS | GGSISSGGYYWS | WIRQHPSKGLEWIG | YIYYSGSTYNPSLKS |
| AX014H22_23N1G2 | VH4-31 | D4-17 | JH6b | ---------------------- | ------N--- | -------------- | ---------------- |
| AX014H22_9N1G2 | " | " | " | ---------------------- | ------N--- | -------------- | ---------------- |
| | | Germline | | QVQLVESGGGVVQPGRSLRLSCAAS | GFTFSSYGMH | WVRQAPGKGLEWVA | VISYDGSNKYYADSVKG |
| AX014H22_7N1G2 | VH3-30 | D3-10 | JH6b | ---------------------- | ---------- | -------------- | ---------------- |
| | | Germline | | QVQLQESGPGLVKPSETLSLTCTVS | GGSISSYYWS | WIRQPAGKGLEWIG | RIYTSGSTNYNPSLKS |
| AX014H21_17_1N1G2 | VH4-4 | D6-19 | JH6b | ---------------------- | ---------- | -------------- | ---------------- |
| AX014H22_29N1G2 | " | " | " | ---------------------- | ---------- | -------------- | ---------------- |
| | | Germline | | QVQIQQSGPGLVKPSQTLSLTCAIS | GDSVSSNSAAWN | WIRQSPSRGLEWIG | RTYYRSKWYNDYAVSVKS |
| AX014H22_10N1G2 | VH6-1 | D1-26 | JH4b | ---------------------- | ---------- | -------------- | --------F------- |
| AX014H22_24N1G2 | " | " | " | ---------------------- | ---------- | -------------- | --------F------- |
| | | Germline | | QVQLQESGPGLVKPSQTLSLTCTVS | GGSISSGGYYWS | WIRQHPGKGLEWIG | YIYYSGSTYNPSLKS |
| AX014H21_5_2N1G2 | VH4-31 | D3-10 | JH4b | ---------------------- | -------R--- | -------------- | ---------------- |
| AX014H21_6_1N1G2 | " | " | " | ---------------------- | ---------- | -------------- | ---------------- |
| | | Germline | | QVQLQESGPGLVKPSQTLSLTCTVS | GGSISSGGYYWS | WIRQHPGKGLEWIG | YIYYSGSTYNPSLKS |
| AX014H22_21N1G2 | VH4-31 | D4-11 | JH6b | ----------A----------- | ---------- | -------------- | ----V----------- |
| | | Germline | | QVQLQESGPGLVKPSQTLSLTCTVS | GGSISSGGYYWS | WIRQHPGKGLEWIG | YIYYSGSTYNPSLKS |
| AX014H22_16N1G2 | VH4-31 | D2-21 | JH6b | ---EQ------------------ | --------V-- | -------------- | ----------R----- |
| | | Germline | | QVQLVQSGAEVKKPGASVKVSCKAS | GYTFTGYYMH | WVRQAPGQGLEWMG | WINPNSGGTNYAQKFQG |
| AX014H22_4N1G2 | VH1-2 | D1-26 | JH4b | ---------------------- | ---------- | -------------- | ---------------- |
| | | Germline | | QVQLQESGPGLVKPSETLSLTCTVS | GGSISSYYWS | WIRQPPGKGLEWIG | YIYYSGSTNYNPSLKS |
| AX014H21_1_1N1G2 | VH4-59 | D3-9 | JH4b | ---------------------- | ------RN--- | -------------- | --------K------- |
| AX014H22_27N1G2 | " | " | " | ---------------------- | ---------- | -------------- | ---------------- |
| AX014H21_14_1N1G2 | " | " | " | ---------------------- | ---------- | -------------- | ---------------- |
| AX014H22_17N1G2 | " | " | " | ---------------------- | ---------- | -------------- | ---------------- |
| AX014H22_26N1G2 | " | " | " | ---------------------- | ---------- | -------------- | ---------------- |

FIGURE 26B

| Chain Name | V | D | J | FR3 | CDR3 | J | |
|---|---|---|---|---|---|---|---|
| AX014H21_8_1N1G2 | VH1-2 | Germline | | RVTMTRDTSISTAYMELSRLRSDDTAVYYCAR | ##L###YYYYGMDV | WGQGTTVTVSS | SEQ ID NO: 124 |
| | | D7-27 | JH6b | ----T-- | GE-WAEG | | SEQ ID NO: 125 |
| | | Germline | | RVTMSVDTSKNQFSLKLSSVTAADTAVYYCAR | ##FLEW#YYYGMDV | WGQGTTVTVSS | SEQ ID NO: 126 |
| AX014H22_5N1G2 | VH4-4 | D3-3 | JH6b | | GG---D--- | | SEQ ID NO: 6 |
| AX014H22_19N1G2 | " | " | " | | GG---D--- | | SEQ ID NO: 3 |
| AX014H22_3N1G2 | " | " | " | | DQG----PL- | | SEQ ID NO: 5 |
| | | Germline | | RVTISVDTSKNQFSLKLSSVTAADTAVYYCA# | #MVRG##FDY | WGQGTTVTVSS | SEQ ID NO: 127 |
| AX014H22_14N1G2 | VH4-61 | D3-10 | JH4b | --A----R | S---VS--- | | SEQ ID NO: 128 |
| | | Germline | | RFTISRDNSKNTLYIQMNSLRAEDTAVYY.## | G#YYYYGMDV | WGQGTTVTVSSA | SEQ ID NO: 129 |
| AX014H22_28_1N1G2 | VH3-23 | D1-26 | JH6b | --AS | -R----D-- | | SEQ ID NO: 130 |
| | | Germline | | RVTISVDTSKNQFSLKLSSVTAADTAVYYCAR | ##V##YYYYGMDV | WGQGTTVTVSS | SEQ ID NO: 131 |
| AX014H22_23N1G2 | VH4-31 | D4-17 | JH6b | --I----E | ER-TD-----L- | | SEQ ID NO: 18 |
| AX014H22_9N1G2 | " | " | " | --I----E | ER-TD-----L- | | SEQ ID NO: 19 |
| | | Germline | | RFTISRDNSKNTLYLQMNSLRAEDTAVYYCAR | ##ITNVRG####YYGMDV | WGQGTTVTVSS | SEQ ID NO: 132 |
| AX014H22_7N1G2 | VH3-30 | D3-10 | JH4b | --F-- | RG----APS | | SEQ ID NO: 133 |
| | | Germline | | RVTMSVDTSKNQFSLKLSSVTAADTAVYYCAR | ##QWL##YYGMDV | WGQGTTVTVSS | SEQ ID NO: 134 |
| AX014H21_17_1N1G2 | VH4-4 | D6-19 | JH6b | | DG----ED--- | | SEQ ID NO: 2 |
| AX014H22_29N1G2 | " | " | " | | DG----ED--- | | SEQ ID NO: 4 |
| | | Germline | | RITINPDTSKNQFSLQLNSVTPEDTAVYYCAR | WELL#FDY | WGQGTTVTVSS | SEQ ID NO: 135 |
| AX014H22_10N1G2 | VH6-1 | D1-26 | JH4b | --F-- | ---G----- | | SEQ ID NO: 136 |
| AX014H22_24N1G2 | " | " | " | --F-- | ---G----- | | SEQ ID NO: 137 |
| | | Germline | | RVTISVDTSKNQFSLKLSSVTAADTAVYYCAR | ###YVGSGS##DY | WGQGTTVTVSS | SEQ ID NO: 138 |
| AX014H21_5_2N1G2 | VH4-31 | D3-10 | JH4b | --I-- | AGT-----YI-- | | SEQ ID NO: 9 |
| AX014H21_6_1N1G2 | " | " | " | --I-- | AGK-----YI-- | | SEQ ID NO: 10 |
| | | Germline | | RVTISVDTSKNQFSLKLSSVTAADTAVYYCAR | #TV##YYYYGMDV | WGQGTTVTVSS | SEQ ID NO: 139 |
| AX014H22_21N1G2 | VH4-31 | D4-11 | JH6b | | E--TD---- | | SEQ ID NO: 17 |
| | | Germline | | RVTISVDTSKNQFSLKLSSVTAADTAVYYCAR | GN###YYYGMDV | WGQGTTVTVSS | SEQ ID NO: 140 |
| AX014H22_16N1G2 | VH4-31 | D2-21 | JH6b | | ---AHD--F- | | SEQ ID NO: 15 |
| | | Germline | | RVTMTRDTSISTAYMELSRLRSDDTAVYYCAR | #GA##FDY | WGQGTLVTVSS | SEQ ID NO: 141 |
| AX014H22_4N1G2 | VH1-2 | D1-26 | JH4b | ----F-- | L--TS--- | | SEQ ID NO: 142 |
| | | Germline | | RVTISVDTSKNQFSLKLSSVTAADTAVYYCAR | ##VDILITGY#YFDY | WGQGTLVTVSS | SEQ ID NO: 143 |
| AX014H21_1_1N1G2 | VH4-59 | D3-9 | JH4b | | RG--F----D-- | | SEQ ID NO: 24 |
| AX014H22_27N1G2 | " | " | " | | RG--F----D-- | | SEQ ID NO: 29 |
| AX014H21_14_1N1G2 | " | " | " | | RG--F----D-- | | SEQ ID NO: 25 |
| AX014H22_17N1G2 | " | " | " | | RG--F----D-- | | SEQ ID NO: 27 |
| AX014H22_26N1G2 | " | " | " | ----R | S--F----HV | | SEQ ID NO: 28 |

FIGURE 27A

| Chain Name | V | D | J | FR1 | CDR1 | FR2 | CDR2 |
|---|---|---|---|---|---|---|---|
| | | Germline | | QVQLQESGPGLVKPSQTLSLTCTVS | GGSISSGGYYWS | WIRQHPGKGLEWIG | YIYYSGSTYYNPSLKS |
| AX014H22_11N1G2 | VH4-31 | D5-24 | JH2 | ------------------------- | ------------ | -------------- | ---------------- |
| | | Germline | | EVQLVESGGGLVQPGGSLRLSCAAS | GFTFSSYSMN | WVRQAPGKGLEWVS | VISSSSTIYYADSVKG |
| AX014H22_13_1N1G2 | VH3-48 | | JH6b | R------------------------ | ---R------ | -------------- | ---------------- |
| | | Germline | | QVQLQESGPGLVKPSQTLSLTCTVS | GGSISSGGYYWS | WIRQHPGKGLEWIG | YIYYSGSTYYNPSLKS |
| AX014H22_15N1G2 | VH4-31 | D3-9 | JH6b | ------------------------- | ------------ | -------------- | --------V------- |
| | | Germline | | QLQLQESGPGLVKPSETLSLTCTVS | GGSISSSYYWG | WIRQHPGKGLEWIG | SIYYSGSTYYNPSLKS |
| AX014H22_25N1G2 | VH4-39 | | JH4b | ------------------------- | D---------- | -------------- | ---------------- |
| AX014H21_10_1N1G2 | " | " | " | ##_EQ-------------------- | D---------- | -------------- | ---------------- |
| | | Germline | | QVQLVESGGGVVQPGRSLRLSCAAS | GFTFSSYGMH | WVRQAPGKGLEWVA | VIWYDGSNKYYADSVKG |
| AX014H22_30N1G2 | VH3-33 | D3-10 | JH6b | ------------------------- | ----A------ | -------------- | ------T--------- |
| | | Germline | | QVQLQESGPGLVKPSQTLSLTCTVS | GGSISSGGYYWS | WIRQHPGKGLEWIG | YIYYSGSTYYNPSLKS |
| AX014H22_9_1N1G2 | VH4-31 | D3-10 | JH6b | ------------------------- | ------S-T-- | -------------- | ------T--------- |
| | | Germline | | QVQLQESGPGLVKPSETLSLTCTVS | GGSISSGGYYWS | WIRQHPGKGLEWIG | YIYYSGSTYYNPSLKS |
| AX014H22_18N1G2 | VH4-31 | D3-9 | JH3b | ------------------------- | --------N-- | -------------- | --------N------- |
| AX014H21_7_1N1G2 | " | " | " | ------------------------- | ------------ | -------------- | --------N------- |
| AX014H22_20N1G2 | " | " | " | ------------------------- | ------------ | -------------- | --------N------- |
| AX014H21_2_1N1G2 | " | " | " | ------------------------- | ------------ | -------------- | ---------------- |
| | | Germline | | QVQLQESGPGLVKPSETLSLTCTVS | GGSISSYYWS | WIRQPPGKGLEWIG | YIYYSGSTNYNPSLKS |
| AX014H22_8_1N1G2 | VH4-59 | D6-13 | JH6b | ###### ------------------ | ------------ | -------------- | ---------------- |
| AX014H22_12N1G2 | " | " | " | ------------------------- | ------------ | -------------- | --------S------- |

FIGURE 27B

| Chain Name | V | D | J | FR3 | CDR3 | J | |
|---|---|---|---|---|---|---|---|
| AX014H22_11N1G2 | | Germline | | RVTISVDTSKNQFSLKLSSVTAADTAVYYCAR | DGYNYWYFDI | WGRGTLVTVSS | SEQ ID NO: 144 |
| | VH4-31 | D5-24 | JH2 | | | | SEQ ID NO: 13 |
| AX014H22_13_1N1G2 | VH3-48 | Germline | JH6b | RFTISRDNAKNSLYLQMNSLRDEDTAVYYCAR | ####GMDV | WGQGTTVTVSSA | SEQ ID NO: 145 |
| | | | | ---------S------------------------ | SLRSG----- | ------------ | SEQ ID NO: 146 |
| AX014H22_15N1G2 | VH4-31 | Germline | JH6b | RVTISVDTSKNQFSLKLSSVTAADTAVYYCAR | ##YYDILTG###YGMDV | WGQGTTVTVSS | SEQ ID NO: 147 |
| | | D3-9 | | | DR-----YYN--- | ------------ | SEQ ID NO: 14 |
| AX014H22_25N1G2 | VH4-39 | Germline | JH4b | RVTISVDTSKNQFSLKLSSVTAADTAVYYCAR | ####FDY | WGQGTLVTVSS | SEQ ID NO: 148 |
| AX014H21_10_1N1G2 | " | " | " | | HGSF--- | | SEQ ID NO: 22 |
| | | | | | HGSF--- | | SEQ ID NO: 21 |
| AX014H22_30N1G2 | VH3-33 | Germline | JH6b | RFTISRDNSKNTLYLQMNSLRAEDTAVYYCAR | ###LLWFGEL###YGMDV | WGQGTTVTVSS | SEQ ID NO: 149 |
| | | D3-10 | | | DRG-----SPH--- | | SEQ ID NO: 150 |
| AX014H21_9_1N1G2 | VH4-31 | Germline | JH6b | RVTISVDTSKNQFSLKLSSVTAADTAVYYCAR | VLLWFG##YGMDV | WGQGTTVTVSS | SEQ ID NO: 151 |
| | | D3-10 | | | ED--v--- | | SEQ ID NO: 12 |
| AX014H22_18N1G2 | VH4-31 | Germline | JH3b | RVTISVDTSKNQFSLKLSSVTAADTAVYYCA# | #YVDILTGY##AFDI | WGQGTMVTVSS | SEQ ID NO: 152 |
| | | D3-9 | | | T-------PD--- | | SEQ ID NO: 16 |
| AX014H21_7_1N1G2 | " | " | " | ---I---------------------------- | T---F---YPD--- | | SEQ ID NO: 11 |
| AX014H22_20N1G2 | " | " | " | | T-------YPD--- | | SEQ ID NO: 153 |
| AX014H21_2_1N1G2 | " | " | " | | T-------PD--- | | SEQ ID NO: 8 |
| AX014H22_8_1N1G2 | VH4-59 | Germline | JH6b | RVTISVDTSKNQFSLKLSSVTAADTAVYYCAR | ###SSS#YYYYYGMDY | WGQGTTVTVSSA | SEQ ID NO: 154 |
| | | D6-13 | | ---T----------------------------- | DQH---V--- | | SEQ ID NO: 30 |
| AX014H22_12N1G2 | " | " | " | | DQH---F--- | | SEQ ID NO: 26 |

FIGURE 28A

| Chain Name | V | J | FR1 | CDR1 | FR2 | CDR2 |
|---|---|---|---|---|---|---|
| AX014H22_15N1K | O12 | Germline | DIQMTQSPSSLSASVGDRVTITC | RASQSISSYLN | WYQQKPGKAPKLLIY | AASSLQS |
| AX014H22_23N1K | " | JK4 | ---------------------- | ----------- | -------V------- | -V----- |
| AX014H21_9_1N1K | " | " | ---------------------- | ----TN----- | --------------- | ------- |
| AX014H22_16N1K | " | " | ---------------------- | ----TN----- | --------------- | ------- |
| AX014H22_3N1K | A27 | Germline | EIVLTQSPGTLSLSPGERATLSC | RASQSVSSSYLA | WYQQKPGQAPRLLIY | GASSRAT |
| | | JK5 | ---------------------- | -------V---- | -------V------ | -V----- |
| AX014H21_6_1N1K | A3 | Germline | DIVMTQSPLSLPVTPGEPASISC | RSSQSLLHSNGYNYLD | WYLQKPGQSPQLLIY | LGSNRAS |
| AX014H21_5_2N1K | " | JK4 | ---------------------- | --------------- | --------------- | ------- |
| AX014H22_8_1N1K | A27 | Germline | EIVLTQSPGTLSLSPGERATLSC | RASQSVSSSYLA | WYQQKPGQAPRLLIY | GASSRAT |
| AX014H22_27N1K | " | JK4 | -TQ------------------- | -----IYIN----- | -----------S--- | ------- |
| AX014H22_5N1K | " | " | ---------------------- | W----F-N----- | --------------- | ------- |
| AX014H21_17_1N1K | " | " | ---------------------- | -------VT---- | --------------- | ------- |
| AX014H22_11N1K | " | " | ---------------------- | W----F-N----- | --------------- | ------- |
| AX014H21_8_1N1K | " | " | ---------------------- | -------G----- | ------------T-- | ------- |
| AX014H22_19N1K | " | " | ---------------------- | -------VT---- | --------------- | ------- |
| AX014H22_4N1K | " | " | ---------------------- | --------------- | --------------- | ------- |
| AX014H22_30N1K | A30 | Germline | DIQMTQSPSSLSASVGDRVTITC | RASQGIRNDLG | WYQQKPGKAPKRLLY | AASSLQS |
| AX014H22_14N1K | " | JK4 | ---------------------- | ----------- | --------------- | ------- |
| AX014H22_28_1N1K | " | " | --RL------------------ | ----------- | --------------- | ------- |
| AX014H21_1_1N1K | L5 | Germline | DIQMTQSPSSVSASVGDRVTITC | RASQGISSWLA | WYQQKPGKAPKLLIY | AASSLQS |
| AX014H22_29N1K | " | JK5 | ---------------------- | ---I---T---- | ---F----------- | ------- |
| AX014H21_14_1N1K | " | " | ---------------------- | ---I---T---- | ---F----------- | ------- |
| AX014H22_17N1K | " | " | ---------------------- | ------------ | --------------- | ------- |
| AX014H22_24N1K | A30 | Germline | DIQMTQSPSSLSASVGDRVTITC | RASQGIRNDLG | WYQQKPGKAPKRLLY | AASSLQS |
| AX014H22_10N1K | " | JK3 | ---------------------- | ------V----- | --------------- | --T-N-- |
| | | " | ---------------------- | ------V----- | --------------- | --T-N-- |
| AX014H21_10_1N1K | A1 | Germline | DVVMTQSPLSLPVTLGQPASISC | RSSQSLVYSDGNTYLN | WFQQRPGQSPRRLIY | KVSNWDS |
| | | JK4 | -------------D-------- | ---------------- | --------------- | ------- |
| AX014H22_9N1K | A27 | Germline | EIVLTQSPGTLSLSPGERATLSC | RASQSVSSSYLA | WYQQKPGQAPRLLIY | GASSRAT |
| AX014H22_26N1K | " | JK2 | ---------------------- | -----Y-N-F--- | --------------- | -----A |
| | | " | ---------------------- | -----Y-N-F--- | --------------- | -----A |

FIGURE 28B

| Chain Name | V | J | | FR3 | CDR3 | J | |
|---|---|---|---|---|---|---|---|
| AX014H22_15N1K | O12 | JK4 | Germline | GVPSRFSGSGSGTDFTLTISSLQPEDFATYYC | QQSYST##T | FGGGTKVEIK | SEQ ID NO: 155 |
| | | | | | | | SEQ ID NO: 67 |
| AX014H22_23N1K | " | " | | ------------------------------ | ---PL--- | ---------- | SEQ ID NO: 69 |
| AX014H21_9_1N1K | " | " | | ------------------------------ | --I----- | --------E- | SEQ ID NO: 66 |
| AX014H22_16N1K | " | " | | ------------------------------ | --I----- | --------E- | SEQ ID NO: 68 |
| AX014H22_3N1K | A27 | JK5 | Germline | GIPDRFSGSGSGTDFTLTISRLEPEDFAVYYC | QQYGSSPIT | FGQGTRLEIK | SEQ ID NO: 156 |
| | | | | | | | SEQ ID NO: 43 |
| | | | | --------------------------- | ---T---- | ---------- | SEQ ID NO: 157 |
| AX014H21_6_1N1K | A3 | JK4 | Germline | GVPDRFSGSGSGTDFTLKISRVEAEDVGVYYC | MQALQT##T | FGGGTKVEIK | SEQ ID NO: 33 |
| AX014H21_5_2N1K | " | " | | ------------------------------ | ---PL--- | ---------- | SEQ ID NO: 32 |
| | | | | ------------------------------ | ---PL--- | ---------- | SEQ ID NO: 80 |
| AX014H22_8_1N1K | A27 | JK4 | Germline | GIPDRFSGSGSGTDFTLTISRLEPEDFAVYYC | QQYGSSLT | FGGGTKVEIKR | SEQ ID NO: 36 |
| AX014H22_27N1K | " | " | | ------------------------------ | ---R---- | --------E- | SEQ ID NO: 42 |
| AX014H22_5N1K | " | " | | ------------------------------ | ---PL--- | ---------- | SEQ ID NO: 45 |
| AX014H21_17_1N1K | " | " | | -----P------------------------ | ---SV--- | ---------- | SEQ ID NO: 37 |
| AX014H22_11N1K | " | " | | -----P------------------------ | ---PL--- | ---------- | SEQ ID NO: 39 |
| AX014H21_8_1N1K | " | " | | ------------------------------ | ---F---- | ---------- | SEQ ID NO: 38 |
| AX014H22_19N1K | " | " | | ------------------------S----- | ---SV--- | ---------- | SEQ ID NO: 40 |
| AX014H22_4N1K | " | " | | ------------------------S----- | ---SV--- | ---------- | SEQ ID NO: 44 |
| AX014H22_30N1K | A30 | JK4 | Germline | GVPSRFSGSGSGTEFTLTISSLQPEDFATYYC | LQHNSY##T | FGGGTKVEIK | SEQ ID NO: 158 |
| | | | | | | | SEQ ID NO: 58 |
| AX014H22_14N1K | " | " | | --------D--------------------- | --Y-PL--- | ---------- | SEQ ID NO: 51 |
| AX014H22_28_1N1K | " | " | | ------------------------------ | ---PL--- | ---------- | SEQ ID NO: 57 |
| AX014H21_1_1N1K | L5 | JK5 | Germline | GVPSRFSGSGSGTDFTLTISSLQPEDFATYYC | QQANSFPIT | FGQGTRLEIK | SEQ ID NO: 159 |
| | | | | | | | SEQ ID NO: 60 |
| AX014H22_29N1K | " | " | | ------------------------------ | --------- | ---------- | SEQ ID NO: 64 |
| AX014H21_14_1N1K | " | " | | ------------------------------ | --------- | ---------- | SEQ ID NO: 61 |
| AX014H22_17N1K | " | " | | ------------------------------ | --------- | ---------- | SEQ ID NO: 63 |
| AX014H22_24N1K | A30 | JK3 | Germline | GVPSRFSGSGSGTEFTLTISSLQPEDFATYYC | LQHNSYPPT | FGPGTKVDIK | SEQ ID NO: 160 |
| AX014H22_10N1K | " | " | | ------------------------------ | --------- | ---------- | SEQ ID NO: 55 |
| AX014H21_10_1N1K | A1 | JK4 | Germline | GVPDRFSGSGSGTDFTLKISRVEAEDVGVYYC | MQGTHWPPLT | FGGGTKVEIKR | SEQ ID NO: 161 |
| | | | | | | | SEQ ID NO: 50 |
| AX014H22_9N1K | A27 | JK2 | Germline | GIPDRFSGSGSGTDFTLTISRLEPEDFAVYYC | QQYGSSP### | FGQGTKLEIK | SEQ ID NO: 162 |
| | | | | | | | SEQ ID NO: 46 |
| AX014H22_26N1K | " | " | | ------------------------------ | --T--RFS | ---------- | SEQ ID NO: 163 |
| | | | | ------------------------------ | --T--RFS | ---------- | SEQ ID NO: 41 |

FIGURE 29A

| Chain Name | V | J | FR1 | CDR1 | FR2 | CDR2 |
|---|---|---|---|---|---|---|
| | | Germline | DIQMTQSPSSVSASVGDRVTITC | RASQGISSWLA | WYQQKPGKAPKLLIY | AASSLQS |
| AK014H22_12N1K | L5 | JK3 | | | | |
| | | Germline | DIVMTQSPLSLPVTPGEPASISC | RSSQSLLHSNGYNYLD | WYLQKPGQSPQLLIY | LGSNRAS |
| AK014H22_7N1K | A3 | JK2 | | ---Y--- | ---F--- | |
| | | Germline | DIQMTQSPSSLSASVGDRVTITC | RASQGIRNDLG | WYQQKPGKAPKRLIY | AASSLQS |
| AK014H22_18N1K | A30 | JK1 | | ---D--- | ---C--- | |
| AK014H21_7_1N1K | " | " | | ---A--- | | |
| AK014H22_21N1K | " | " | | ---A--- | | |
| AK014H22_20N1K | " | " | | | | |
| AK014H22_25N1K | " | " | | | | |
| AK014H21_2_1N1K | " | " | | ---D--- | ---C--- | |
| | | Germline | DIVMTQTPLSSPVTLGQPASISC | RSSQSLVHSDGNTYLS | WLQQRPGQPPRLLIY | KISNRFS |
| AK014H22_13_1N1K | A23 | JK4 | | -A- | | |

FIGURE 29B

| Chain Name | V | J | FR3 | CDR3 | J | SEQ ID NO |
|---|---|---|---|---|---|---|
| | | Germline | GVPSRFSGSGSGTDFTLTISSLQPEDFATYYC | QQANSFPLT | FGPGTKVDIK | SEQ ID NO: 164 |
| AX014H22_12N1K | L5 | JK3 | | | | SEQ ID NO: 62 |
| | | Germline | GVPDRFSGSGSGTDFTLKISRVEAEDVGVYYC | MQALQTP## | FGQGTKLEIK | SEQ ID NO: 165 |
| AX014H22_7N1K | A3 | JK2 | | ---RS | | SEQ ID NO: 34 |
| | | Germline | GVPSRFSGSGSGTEFTLTISSLQPEDFATYYC | LQHNSYPWT | FGQGTKVEIK | SEQ ID NO: 166 |
| AX014H22_18N1K | A30 | JK1 | | | | SEQ ID NO: 52 |
| AX014H21_7_1N1K | " | " | ---S------------------------------ | ---YH--- | | SEQ ID NO: 49 |
| AX014H22_21N1K | " | " | ---S------------------------------ | ---YH--- | | SEQ ID NO: 54 |
| AX014H22_20N1K | " | " | ------T--------------------------- | ---YK--- | | SEQ ID NO: 53 |
| AX014H22_25N1K | " | " | ------T--------------------------- | ---YK--- | | SEQ ID NO: 56 |
| AX014H21_2_1N1K | " | " | ---S------------------------------ | | | SEQ ID NO: 48 |
| | | Germline | GVPDRFSGSGAGTDFTLKISRVEAEDVGVYYC | MQATQF##T | FGGGTKVEIKR | SEQ ID NO: 167 |
| AX014H22_13_1N1K | A23 | JK4 | | ---PL--- | | SEQ ID NO: 168 |

ANTIBODIES AGAINST CARBONIC ANHYDRASE IX (CA IX) TUMOR ANTIGEN

RELATED APPLICATIONS

This application claims priority from U.S. Provisional Application No. 60/337,275 filed on Dec. 3, 2001.

BACKGROUND OF THE INVENTION

1. Field of the Invention

Embodiments of the present invention concern antibodies binding carbonic anhydrase IX (CA IX) tumor antigen as well as methods and means for making and using such antibodies.

2. Description of the Related Art

The therapeutic utility of monoclonal antibodies (mAbs) (G. Kohler and C. Milstein, *Nature* 256:495-497 (1975)) is being realized. Monoclonal antibodies have now been approved as therapies in transplantation, cancer, infectious disease, cardiovascular disease and inflammation. Different isotypes have different effector functions. Such differences in function are reflected in distinct 3-dimensional structures for the various immunoglobulin isotypes (P. M. Alzari et al., *Annual Rev. Immunol.*, 6:555-580 (1988)).

Because mice are convenient for immunization and recognize most human antigens as foreign, mAbs against human targets with therapeutic potential have typically been of murine origin. However, murine mAbs have inherent disadvantages as human therapeutics. They require more frequent dosing as mAbs have a shorter circulating half-life in humans than human antibodies. More critically, the repeated administration of murine antibodies to the human immune system causes the human immune system to respond by recognizing the mouse protein as a foreign and generating a human anti-mouse antibody (HAMA) response. Such a HAMA response may result in allergic reaction and the rapid clearing of the murine antibody from the system thereby rendering the treatment by murine antibody useless. To avoid such affects, attempts to create human immune systems within mice have been attempted.

Initial attempts hoped to create transgenic mice capable of responding to antigens with antibodies having human sequences (See Bruggemann et al., *Proc. Nat'l. Acad. Sci. USA* 86:6709-6713 (1989)), but were limited by the amount of DNA that could be stably maintained by available cloning vehicles. The use of yeast artificial chromosome (YAC) cloning vectors led the way to introducing large germline fragments of human Ig locus into transgenic mammals. Essentially a majority of the human V, D, and J region genes arranged with the same spacing found in the human genome and the human constant regions were introduced into mice using YACs. One such transgenic mouse strain is known as XenoMouse(r) mice and is commercially available from Abgenix, Inc. (Fremont Calif.).

XenoMouse mice are strains of mice that have inactivated mouse IgH and IgK loci and is transgenic for functional megabase-sized human IgH and IgK transgenes. Further, XenoMouse mice are transgenic mice capable of producing high affinity, fully human antibodies of the desired isotype (i.e., IgG1) in response to immunization with virtually any desired antigen. Such a mAbs can be used to direct complement dependent cytotoxicity or antibody-dependent cytotoxicity to a target cell.

Because CA IX is a biomarker found to be overexpressed in most cervical carcinomas (Brewer et al., *Gynecol. Oncol.*, 63(3): 337-44 (1996)) and in some tumors, particularly renal cell carcinoma (Beasley et al., *Cancer Res.*, 61(13):5262-7 (2001) esophageal cancers (Kaluz et al., *J. Biol. Chem.*, 274946):32588-32595 (1999)), and breast cancer, the role of CA IX in tumor cell progression and growth is of intense interest. According to Chia et al., *J. Clin. Oncol.*, 19(16): 3660-8 (2001), CA IX, also referred to as MN, may have a role as a marker of hypoxia in carcinomas. Further, overexpression of CA IX may help to maintain the intracellular pH (Beasley et al., *Cancer Res.* 61(13):5262-7 (2001), giving tumor cells a survival advantage and enhancing resistance to radiotherapy and chemotherapy. Accordingly, CA IX may be an ideal potential target for therapy against such tumors.

Monoclonal antibodies specific for CA IX have been generated (Zavada et al., *Br. J. Cancer*, 82(11):1808-13 (2000)). These antibodies were specifically directed to the adhesion domain and affected the ability of CA IX to attach to tumor cells. The adhesion domain is located in the proteoglycan domain and contains a sixfold tandem repeat of the six amino acid sequence GEEDLP (Brewer et al., *Gynecol Oncol.*, 63(3); 337-44 (1996). From a phage display library of random heptapeptides, several heptapeptides with the ability to compete for the adhesion epitope on CA IX and inhibit adhesion of cells to CA IX have been identified.

It is believed that the first anti-MN antibody was the G250 antibody generated by Oosterwijk et al. (Am J Pathol 1986 May; 123(2):301-9; Oosterwijk et al. Int J Cancer 1986 Oct. 15; 38(4):489-94) which was an antibody that bound to an antigen that was expressed preferentially in renal cell carcinomas. The G250 antibody was subsequently identified to bind to the MN antigen (Uemura et al. Br J Cancer 1999October;81(4):741-6).

Although monoclonal antibodies have been identified that specifically bind to CA IX, antibodies that specifically inhibit its biological activities, such as cell proliferation and survival which may be essential to tumor progression are needed. The ability to affect the growth and/or survival of tumor cells expressing CA IX on the cell surface may prove to be a treatment having widespread application to many patients afflicted with tumors.

SUMMARY OF THE INVENTION

Embodiments of the present invention are based on the development of monoclonal antibodies that were found to bind CA IX and affect CA IX function.

In one aspect, the invention provides an anti-human CA IX monoclonal antibody which binds to and neutralizes a biological activity of at least human CA IX. The antibody can significantly reduce or eliminate a biological activity of the human CA IX in question.

The biologic activity of the subject human CA IX is likely to be important for cell proliferation or survival under conditions of stress.

In one embodiment, the invention provides an isolated monoclonal antibody comprising a heavy chain amino acid, having an amino acid sequence selected from the group consisting of SEQ ID NOs: 2, 3, 4, 5, 6, 8, 9, 10, 11, 12, 13, 14, 15, 16, 17, 18, 19, 21, 22, 24, 25, 26, 27, 28, 29, 30, 71, 72, 73, 75, 77, 79, 90, 92, 94, 96, 98, 100, 102, 125, 128, 130, 133, 136, 137, 142, 146, 150, 153, 169, 171, 172 and 246 and wherein said monoclonal antibody specifically binds CA IX. The antibody is preferably a fully human antibody. In a further embodiment, the antibody further comprises a light chain amino acid having an amino acid sequence selected from the group consisting of SEQ ID NOs: 32, 33, 34, 36, 37, 38, 39, 40, 41, 42, 43, 44, 45, 46, 48, 49, 50, 51, 52, 53, 54, 55, 56, 57, 58, 60, 61, 62, 63, 64, 66, 67, 68, 69, 81, 82, 83, 85, 87, 89, 91, 93, 95, 97, 99, 101, 103, 162, 168, 175, 177, 179 and 245. The monoclonal antibody may further be associated with a therapeutically acceptable carrier or may be conjugated to a therapeutic or cytotoxic agent whereing the further therapeutic agent is a toxin, such as a catalytic toxin, ricin, Pseudomonas exotoxin, or the drug-like toxin, maytansinoid, auristatinE or geldanamycin, or a radioisotope. Preferably, such an antibody may be used for treatment of diseases, such as tumors.

In another aspect, the invention provides a method of inhibiting cell proliferation associated with the expression of CA IX tumor antigen comprising treating cells expressing CA IX with an effective amount of an CA IX monoclonal antibody.

In another aspect, the invention provides a method for treatment of a disease associated with the expression of CA IX in a patient, comprising administering to the patient an effective amount of an CA IX monoclonal antibody. The patient is preferably a human mammalian patient and the disease is preferably a tumor that is selected from the group consisting of colorectal neoplasms, colorectal tumors, renal cell carcinoma (RCC), cervical carcinoma, cervical intraepithelial squamous and glandular neoplasia, esophageal tumors, and breast cancer.

Also provided is an isolated nucleic acid molecule encoding any of the antibodies described herein, a vector comprising the isolated nucleic acid molecule, a host cell transformed with the nucleic acid molecule, and a method of producing the antibody comprising culturing the host cell under conditions wherein the nucleic acid molecule is expressed to produce the antibody and optionally recovering the antibody from the host cell. The antibody may be of the IgG class. The isolated nucleic acid molecule preferably comprises a nucleotide sequence encoding a heavy chain variable domain of a monoclonal antibody, wherein said nucleotide sequence is selected from the group consisting of SEQ ID NOs: 104, 106, 108, 110, 112, 114, 116, 118, 170, 172, 174, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211 and 212, or a nucleotide sequence encoding a light chain variable domain of a monoclonal antibody, wherein said nucleotide sequence is selected from the group consisting of SEQ ID NOs: 105, 107, 109, 111, 113, 115, 117, 119, 176, 178, 180, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243 and 244.

In yet another aspect, the invention provides an antibody of the invention linked to a radioisotope.

BRIEF DESCRIPTION OF THE DRAWINGS

FIG. 1 shows the alignment of the amino acid sequences encoding for the heavy chain variable domain regions of the immunoglobulins directed against CA IX, AB-MN-21.17.1_HC (SEQ ID NO: 2), AB-MN-22.19_HC (SEQ ID NO: 3), AB-MN-22.29_HC (SEQ ID NO: 4), AB-MN-22.3_HC (SEQ ID NO: 5) and AB-MN-22.5_HC (SEQ ID NO: 6), with germline Vgamma/D/J sequence of VH4-4 (SEQ ID NO: 1). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIGS. 3A and 3B show the alignment of the amino acid sequences encoding for the heavy chain variable domain regions of the immunoglobulins directed against CA IX, AB-MN-21.2.1_HC (SEQ ID NO: 8), AB-MN-21.5.2_HC (SEQ ID NO: 9), AB-MN-21.6.1_HC (SEQ ID NO: 10), AB-MN-21.7.1_HC (SEQ ID NO: 11), AB-MN-21.9.1_HC (SEQ ID NO: 12), AB-MN-22.11_HC (SEQ ID NO: 13), AB-MN-22.15_HC (SEQ ID NO: 14), AB-MN-22.16_HC (SEQ ID NO: 15), AB-MN-22.18_HC (SEQ ID NO: 16), AB-MN-22.21_HC (SEQ ID NO: 17), AB-MN-22.23_HC (SEQ ID NO: 18) and AB-MN-22.9_HC (SEQ ID NO: 19) with germline Vgamma/D/J sequence of VH4-31 (SEQ ID NO: 7). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 5 shows the alignment of the amino acid sequences encoding for the heavy chain variable domain regions of the immunoglobulins directed against CA IX, AB-MN-21.10.1_HC (SEQ ID NO: 21) and AB-MN-22.25_HC (SEQ ID NO: 22) with germline Vgamma/D/J sequence of VH4-39 (SEQ ID NO: 20). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 6 shows the alignment of the amino acid sequences encoding for the heavy chain variable domain regions of the immunoglobulins directed against CA IX, AB-MN-21.1.1_HC (SEQ ID NO: 24), AB-MN-21.14.1_HC (SEQ ID NO: 25), AB-MN-22.12_HC (SEQ ID NO: 26), AB-MN-22.17_HC (SEQ ID NO: 27), AB-MN-22.26_HC (SEQ ID NO: 28), AB-MN-22.27_HC (SEQ ID NO: 29) and AB-MN-22.8.1_HC (SEQ ID NO: 30) with germline Vgamma/D/J sequence of VH4-59 (SEQ ID NO: 23). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 8 shows the alignment of the amino acid sequences encoding for the light chain variable domain regions of the immunoglobulins directed against CA IX, AB-MN-21.5.2_LC (SEQ ID NO: 32), AB-MN-21.6.1_LC (SEQ ID NO: 33) and AB-MN-22.7_LC (SEQ ID NO: 34) with germline $V_{Kappa}$/J sequence of VK-A19 (SEQ ID NO: 31). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 9 shows a dendrogram representing the hierarchy of the anti-CA IX immunoglobulins, AB-MN-21.5.2_LC, AB-MN-21.6.1_LC and AB-MN-22.7_LC based on their similarity with the variable light chain region of VK-A19.

FIG. 10 shows the alignment of the amino acid sequences encoding for the light chain variable domain regions of the immunoglobulins directed against CA IX, AB-MN-22.8.1_LC (SEQ ID NO: 36), AB-MN-21.17.1_LC (SEQ ID NO: 37), AB-MN-21.8.1_LC (SEQ ID NO: 38), AB-MN-22.11_LC (SEQ ID NO: 39), AB-MN-22.19_LC (SEQ ID NO: 40), AB-MN-22.26_LC (SEQ ID NO: 41), AB-MN-22.27_LC (SEQ ID NO: 42), AB-MN-22.3_LC (SEQ ID NO: 43), AB-MN-22.4_LC (SEQ ID NO: 44), AB-MN-22.5_LC (SEQ ID NO: 45) and AB-MN-22.9_LC (SEQ ID NO: 46) with germline $V_{Kappa}$/J sequence of VK-A27 (SEQ ID NO: 35). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 12 shows the alignment of the amino acid sequences encoding for the light chain variable domain regions of the immunoglobulins directed against CA IX, AB-MN-21.2.1_LC (SEQ ID NO: 48), AB-MN-21.7.1_LC (SEQ ID NO: 49), AB-MN-22.10_LC (SEQ ID NO: 50), AB-MN-22.14_LC (SEQ ID NO: 51), AB-MN-22.18_LC (SEQ ID NO: 52), AB-MN-22.20_LC (SEQ ID NO: 53), AB-MN-22.21_LC (SEQ ID NO: 54), AB-MN-22.24_LC (SEQ ID NO: 55), AB-MN-22.25_LC (SEQ ID NO: 56), AB-MN-22.28.1_LC (SEQ ID NO: 57) and AB-MN-22.30_LC (SEQ ID NO: 58) with germline $V_{Kappa}$/J sequence of VK-A30 (SEQ ID NO: 47). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 14 shows the alignment of the amino acid sequences encoding for the light chain variable domain regions of the immunoglobulins directed against CA IX, AB-MN-21.1.1_LC (SEQ ID NO: 60), AB-MN-21.14.1_LC (SEQ ID NO: 61), AB-MN-22.12_LC (SEQ ID NO: 62), AB-MN-22.17_LC (SEQ ID NO: 63) and AB-MN-22.29_LC (SEQ ID NO: 64) with germline $V_{Kappa}$/J sequence of VK-L5 (SEQ ID NO: 59). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 15 shows a dendrogram representing the hierarchy of the anti-CA IX immunoglobulins, AB-MN-21.1.1_LC, AB-MN-21.14.1_LC, AB-MN-22.12_LC, AB-MN-22.17_LC and AB-MN-22.29_LC based on their similarity with the variable light chain region of VK-L5.

FIG. 16 shows the alignment of the amino acid sequences encoding for the light chain variable domain regions of the immunoglobulins directed against CA IX, AB-MN-21.9.1_LC (SEQ ID NO: 66), AB-MN-22.15_LC (SEQ ID NO: 67), AB-MN-22.16_LC (SEQ ID NO: 68) and AB-MN-22.23_LC (SEQ ID NO: 69) with germline $V_{Kappa}$/J sequence of VK-O12 (SEQ ID NO: 65). The CDRs, CDR1, CDR2, CDR3 in the immunoglobulins are shown under the solid horizontal lines. "AB-MN-21." antibodies are generated in IgG1 mice and "AB-MN-22." antibodies are generated in IgG2 mice. The letters in bold represent conservative and non-conservative amino acid changes.

FIG. 18 shows the alignment of the amino acid sequences encoding for the heavy chain variable domain regions of the immunoglobulins directed against CA IX, AB-MN-XG1-080 (SEQ ID NO: 71), AB-MN-XG1-141 (SEQ ID NO: 72), AB-MN-XG1-174 (SEQ ID NO: 73) with germline Vgamma/D/J sequence of VH4-59 (DP-71)/D3-JH4b (SEQ ID NO: 70), AB-MN-XG1-023 (SEQ ID NO: 75), germline Vgamma/D/J sequence of VH4-30.1 (DP-65)/D3-9/JH5b (SEQ ID NO: 74) AB-MN-XG1-051 (SEQ ID NO: 77) germline Vgamma/D/J sequence of VH3.21 (DP-77)/D5-18/JH4b (SEQ ID NO: 76), and AB-MN-XG1-109 (SEQ ID NO: 79) with germline Vgamma/D/J sequence of VH4.04 (VIV-4)/D1-20/JH6b (SEQ ID NO 78). The CDRs, CDR1, CDR2, CDR3 in the immunoglobulins are shown under respective column headings. These "AB-MN-XG1" antibodies are generated in IgG1 Xenomice.

FIG. 19 shows the alignment of the amino acid sequences encoding for the light chain variable domain regions of the immunoglobulins directed against CA IX, AB-MN-XG1-080 (SEQ ID NO: 81), AB-MN-XG1-141 (SEQ ID NO: 82), AB-MN-XG1-174 (SEQ ID NO: 83) with germline $V_{Kappa}$/J sequence of A27/JK4 (SEQ ID NO: 80), AB-MN-XG1-023 (SEQ ID NO: 85), germline $V_{Kappa}$/J sequence of L19/JK1 (SEQ ID NO: 84) AB-MN-XG1-051 (SEQ ID NO: 87) germline $V_{Kappa}$/J sequence of A20/JK1 (SEQ ID NO: 86), and AB-MN-XG1-109 (SEQ ID NO: 89) with germline $V_{Kappa}$/J sequence of O2/JK3 (SEQ ID NO 88). The CDRs, CDR1, CDR2, CDR3 in the immunoglobulins are shown under respective column headings. These "AB-MN-XG1" antibodies are generated in IgG1 Xenomice.

FIGS. 26A-B show the alignment of the amino acid sequences encoding for the heavy chain variable domain regions of the immunoglobulins directed against CA IX, AX014H21_8_1N1G2 (SEQ ID NO: 125) with germline Vgamma/D/J sequence of VH1-2/D7-27/JH6b (SEQ ID NO: 124), AX014H22_5N1G2 (SEQ ID NO: 6), AX014H22_19N1G2 (SEQ ID NO: 3) and AX014H22_3N1G2 (SEQ ID NO: 5) with germline Vgamma/D/J sequence of VH4-4/D3-3/JH6b (SEQ ID NO: 126), AX014H22_14N1G2 (SEQ ID NO: 128) with Vgamma/D/J sequence of VH4-61/D3-10/JH46 (SEQ ID NO: 127), AX014H22_28.1N1G (SEQ ID NO: 130) with Vgamma/D/J sequence of VH3-23/D1-26/JH6b (SEQ ID NO: 129), AX014H22_23N1G2 (SEQ ID NO: 18) and AX014h22_9N1G2 (SEQ ID NO: 19) with Vgamma/D/J sequence of VH4-31/D4-17/JH6b (SEQ ID NO: 131), AX014H22_7N1G2 (SEQ ID NO: 133) with Vgamma/D/J sequence of VH3-30/D3-10/JH6b (SEQ ID NO: 132), AX014H21_17_1N1G (SEQ ID NO: 2) and AX014H22_29N1G2 (SEQ ID NO: 4) with Vgamma/D/J sequence of VH4-4/D6-19/JH6b (SEQ ID NO: 134), AX014H22_10N1G2 (SEQ ID NO: 136) AND AX014H22_24N1G2 (SEQ ID NO: 137) with Vgamma/D/J sequence of VH6-1/D1-26/JH4b (SEQ ID NO: 135), AX014H21_5_2N1G2 (SEQ ID NO: 9) and AX014H21_6_1N1G2 (SEQ ID NO: 10) with Vgamma/D/J sequence of VH4-31/D3-10/JH4b (SEQ ID NO: 138), AX014H22_21N1G2 (SEQ ID NO: 17) with Vgamma/D/J sequence of VH4-31/D4-11/JH6b (SEQ ID NO: 139), AX014H22_16N1G2 (SEQ ID NO: 15) with VH4-31/D2-21/JH6b (SEQ ID NO: 140), AX014H22_4N1G2 (SEQ ID NO: 142) with Vgamma/D/J sequence of VH1-2/D1-26/JH4b (SEQ ID NO: 141). AX014H21_1_1N1G2 (SEQ ID NO: 24), AX014H22_27N1G2 (SEQ ID NO: 29), AX014H21_14_1N1G2 (SEQ ID NO: 25), AX014H22_17N1G2 (SEQ ID NO: 27) and AX014H22_26N1G2 (SEQ ID NO: 28) with Vgamma/D/J sequence of VH4-59/D3-9/JH4b (SEQ ID NO: 143). The CDRs, CDR1, CDR2, CDR3 and FR regions in the immunoglobulins are shown under the respective column headings. The "AX014H21" and "AX014H22" antibodies are generated in IgG1 and IgG2 Xenomice, respectively.

FIGS. 27A-B show the alignment of the amino acid sequences encoding for the heavy chain variable domain regions of the immunoglobulins directed against CA IX, AX014H22_11N1G2 (SEQ ID NO: 13) with germline Vgamma/D/J sequence of VH4-31/D5-24/JH2 (SEQ ID NO: 144), AX014H22_13_1N1G2 (SEQ ID NO: 146) with germline Vgamma/D/J sequence of VH3-48/JH6b (SEQ ID NO: 145), AX014H22_15N1G2 (SEQ ID NO: 14) with germline Vgamma/D/J sequence of VH4-31/D3-9/JH46 (SEQ ID NO: 147), AX014H22_25N1G2 (SEQ ID NO: 22) and AX014H21_10_1N1G2 (SEQ ID NO: 21) with germline Vgamma/D/J sequence of VH4-39/JH6b (SEQ ID NO: 148), AX014H22_30N1G2 (SEQ ID NO: 150) with germline Vgamma/D/J sequence of VH3-33/D3-10/JH6b (SEQ ID NO: 149), AX014H21_9_1N1G2 (SEQ ID NO: 12) with germline Vgamma/D/J sequence of VH4-31/D3-10/JH6b (SEQ ID NO: 151), AX014H22_18N1G2 (SEQ ID NO: 16), AX014H21_7_1N1G2 (SEQ ID NO: 11), AX014H22_20N1G2 (SEQ ID NO: 153) and AX014H21_2_1N1G2 (SEQ IDNO: 8) with germline Vgamma/D/J sequence of VH4-31/D3-9/JH6b (SEQ ID NO: 152), and AX014H22_8_1N1G2 (SEQ ID NO: 30) and AX014H22_12N1G2 (SEQ ID NO: 26) with germline Vgamma/D/J sequence of VH4-59/D6-13/JH6b (SEQ ID NO: 154). The CDRs, CDR1, CDR2, CDR3 and FR regions in the immunoglobulins are shown under the respective column headings. The "AX014H21" and "AX014H22" antibodies are generated in IgG1 and IgG2 Xenomice, respectively.

FIGS. 28A-B show the alignment of the amino acid sequences encoding for the light chain variable domain regions of the immunoglobulins directed against CA IX, AX014H22_15N1K (SEQ ID NO: 67), AX014H22_23N1K (SEQ ID NO: 69), AX014H21_9_1N1K (SEQ ID NO: 66) and AX014H22-16N1K (SEQ ID NO: 68) with germline Vkappa/J sequence of O12/JK4 (SEQ ID NO: 155), AX014H22_3N1K (SEQ ID NO: 43) with germline Vkappa/J sequence of A27/JK5 (SEQ ID NO: 156), AX014H21_6_1N1K (SEQ ID NO: 33) and AX014H21_5_2N1K (SEQ ID NO: 32) with germline Vkappa/J sequence of A3/JK4 (SEQ ID NO: 157), AX014H22_8_1N1K (SEQ ID NO: 36), AX014H22_27N1K (SEQ ID NO: 42), AX014H22_5N1K (SEQ ID NO: 45), AX014H21_17_1N1K (SEQ ID NO: 37), AX014H22_11N1K (SEQ ID NO: 39), AX014H21_8_1N1K (SEQ ID NO: 38), AX014H22_19N1K (SEQ ID NO: 40) and AX014H22_4N1K (SEQ ID NO: 44) with germline Vkappa/J sequence of A27/JK4 (SEQ ID NO: 80), AX014H22_30N1K (SEQ ID NO: 58), AX014H22_14N1K (SEQ ID NO: 51) and AX014H22_28_1N1K (SEQ ID NO: 57) with germline Vkappa/J sequence of A30/JK4 (SEQ ID NO: 158), AX014H21_1_1N1K (SEQ ID NO: 60), AX014H22_29N1K (SEQ ID NO: 64), AX014H21_14_1N1K (SEQ ID NO: 61) and AX014H22_17N1K (SEQ ID NO: 63) with germline Vkappa/J sequence of L5/JK5 (SEQ ID NO: 159), AX014H22_24N1K (SEQ ID NO: 55) and AX014H22_10N1K (SEQ ID NO: 50) with germline Vkappa/J sequence of A30/JK3 (SEQ ID NO: 160), AX014H21_10_1N1K (SEQ ID NO: 162) with germline Vkappa/J sequence of A1/JK4 (SEQ ID NO: 161) and AX014H22_9N1K (SEQ ID NO: 46) and AX014H22_26N1K (SEQ ID NO: 41) with germline Vkappa/J sequence of A27/JK2 (SEQ ID NO: 163). The CDRs, CDR1, CDR2, CDR3 and FR regions in the immunoglobulins are shown under the respective column headings. The "AX014H21" and "AX014H22" antibodies are generated in IgG1 and IgG2 Xenomice, respectively.

FIGS. 29A-B show the alignment of the amino acid sequences encoding for the light chain variable domain regions of the immunoglobulins directed against CA IX, AX014H22_12N1K (SEQ ID NO: 62) with germline Vkappa/J sequence of L5/JK3 (SEQ ID NO: 164), AX014H22_7N1K (SEQ ID NO: 34) with germline Vkappa/J sequence of A3/JK2 (SEQ ID NO: 165), AX014H22_18N1K (SEQ ID NO: 52), AX014H21_7_1N1K (SEQ ID NO: 49), AX014H22_21N1K (SEQ ID NO: 54), AX014H22_20N1K (SEQ ID NO: 53), AX014H22_25N1K (SEQ ID NO: 56) AND AX014H21_2_1N1K (SEQ ID NO: 48) with germline Vkappa/Jsequence of A30/JK1 (SEQ ID NO: 166) and AX014H22_13_1N1K (SEQ ID NO: 168) with germline Vkappa/J sequence of A23/JK4 (SEQ ID NO: 167). The CDRs, CDR1, CDR2, CDR3 and FR regions in the immunoglobulins are shown under the respective column headings. The "AX014H21" and "AX014H22" antibodies are generated in IgG1 and IgG2 Xenomice, respectively.

DETAILED DESCRIPTION OF THE PREFERRED EMBODIMENT

A. Definitions

Figure 2:
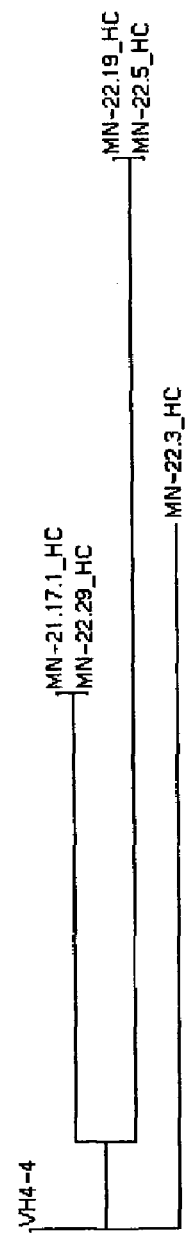
FIG. 2 shows a dendrogram representing the hierarchy of the anti-CA IX immunoglobulins, AB-MN-21.17.1_HC, AB-MN-22.19_HC, AB-MN-22.29_HC, AB-MN-22.3_HC and AB-MN-22.5_HC, based on their similarity with the variable heavy chain region,VH4-4.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* $2^{nd}$ ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

As used herein, the term "CA IX" and "AX014" when used herein represent the tumor-associated antigen that is also an enzyme belonging to the carbonic anhydrase (CA) family. CA IX is also referred to in the art as "MN". For purposes of this invention, from here on, "CA IX" refers to both CA IX and MN. More specifically, CA IX is a transmembrane glycoprotein with an active extracellular enzyme site. Further "AX014H" when used herein refers to human AX014.

"Polymerase chain reaction" or "PCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Pres, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., *Nature* 342:877-883 (1989)).

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The "light chains" of antibodies (immunoglobulins) from any vertebrate species can be assigned to one of two clearly distinct types, called κ and λ, based on the amino acid sequences of their constant domains.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The term "antibody" includes all classes and subclasses of intact immunoglobulins. The term "antibody" also covers antibody fragments. The term "antibody" specifically covers monoclonal antibodies, including antibody fragment clones.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al, *Nature,* 352:624-628 (1991) and Marks et al., *J. Mol. Biol.,* 222:581-597 (1991), for example.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

By "neutralizing antibody" is meant an antibody molecule which is able to eliminate or significantly reduce an effector function of a target antigen to which is binds. Accordingly, a "neutralizing" anti-CA IX antibody is capable of eliminating or significantly reducing an effector function, such as CA IX enzyme activity.

Antibody-dependent cell-mediated cytotoxicity" and "ADCC" refer to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγIII. Fc expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362, or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1988).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991). The constant domains are not involved directly in binding an antibody to an antigen, but exhibit various effector functions, such as participation of the antibody in antibody-dependent cellular toxicity.

Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., *Sequences of Proteins of Immunological Interest*, 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk *J. Mol. Biol* 196:901-917 (1987)). "Framework Region" or "FR" residues are those variable domain residues other than the hypervariable region residues as herein defined.

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for (monoclonal or polyclonal) antibodies on protein antigens.

The term amino acid or amino acid residue, as used herein, refers to naturally occurring L amino acids or to D amino acids as described further below with respect to variants. The commonly used on- and three-letter abbreviations for amino acids are used herein (Bruce Alberts et al., *Molecular Biology of the Cell*, Garland Publishing, Inc., New York (3d ed. 1994)).

The term "disease state" refers to a physiological state of a cell or of a whole mammal in which an interruption, cessation, or disorder of cellular or body functions, systems, or organs has occurred.

The term "treat" or "treatment" refer to both therapeutic treatment and prophylactic or preventative measures wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment of the present invention. This includes chronic and acute disorders or disease including those pathological conditions which predispose the mammal to the disorder in question. Non-limiting examples of disorders to be treated herein include benign and malignant tumors, leukemias and lymphoid malignancies, in particular breast, rectal, ovarian, renal, pancreatic, stomach, endometrial, salivary gland, kidney, colon, thyroid, pancreatic, prostate or bladder cancer. A preferred disorder to be treated in accordance with the present invention is malignant tumor, such as cervical carcinomas and cervical intraepithelial squamous and glandular neoplasia, renal cell carcinoma (RCC), esophageal tumors, and carcinomas of epithelial origin.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Lipofection" refers to a practical nonviral method for introduction of genetic information into target tissues. Non-viral methods include both chemical or physical methods. Lipofection uses an electrostatically bonded complex of positively charged lipids and negatively charged DNA as a vector which fuses with the cell membrane and delivers DNA into the cytoplasm. Lipofection differs from viral methods in that the efficiency of transfer of genetic information by lipofection is lower than by viral vectors and that the expression of the gene is transient. Alternatively, the complex of lipid and DNA is more stable and easier to handle when compared to viral vectors.

A "plaque assay" specifically refers to the ability of a single, antibody-producing plasma cell to initiate killing of target cells. For example, B cells secrete IgM antibody to antigenic determinants present on the surface of target erythrocytes with T-cell help, resulting in antibody-erythrocyte binding. The presence of an adequate complement source allows adequate complement-mediated lysis of the antibody-coated erythrocytes, resulting in the formation of clear-zones or "plaques" in the agar. Located within the center of each plaque is a single, antibody-producing plasma cell.

B. Methods for Carrying Out the Invention

Embodiments of the invention relate to antibodies directed against the CA IX tumor antigen and methods and means for making and using such antibodies. The present invention provides antibodies that affect the ability of the tumor cell marker, CA IX/MN, to function in tumor cell progression.

In one embodiment, antibodies against CA IX are specifically directed to the catalytic domain of CA IX. Since a number of antibodies specific for other regions of CA IX, such as the adhesion domain (Zavada et al., *Br. J. Cancer*, 82(11):1808-13 (2000))., and with distinct affects on CA IX, methods for distinguishing such antibodies from those that particularly bind the catalytic domain of CA IX are herein described. In one aspect, the present invention includes methods for screening for such antibodies specifically directed to the catalytic domain of CA IX. For example, experiments detailed below in Example 2, may be of use for screening such particular antibodies directed to the catalytic domain of CA IX. Specifically, assays for measuring the ability of antibodies to block the catalytic function of CA IX or in some way inhibit CA IX to perform its catalytic function, for example, by promoting internalization of CA IX into cells so that CA IX is no longer able to perform its catalytic function on the surface of cells such as tumor cells are included. Such assays may be of use for distinguishing antibodies that bind the catalytic domain and affect the catalytic activity of CA IX from antibodies that function in a different manner. In a further aspect, screening for binding of antibodies that bind to the catalytic domain of CA IX may be performed using the catalytic domain (CD) of CA IX as a target in ELISA screening, further described in Example 2.

In another particular embodiment, the antibodies of the present invention are directed for use in human therapy against diseases. Disease include diseases associated with abnormal cell growth such as tumors. More specifically, diseases may include diseases that rely on the catalytic activity of CA IX for survival and progression. In a particular aspect of the invention, antibodies that are able to inhibit the role of CA IX/MN in cell growth and progression, more specifically tumor cell growth, survival and progression, find use in the treatment of such diseases characterized by abnormal cell growth, in particular, tumors, carcinomas such as renal cell carcinoma and cervical carcinoma, and cancers.

1. Generation of Anti-CA IX Antibodies

A description follows as to exemplary techniques for the production of the antibodies used in accordance with the present invention.

(a) Monoclonal Antibodies

Monoclonal antibodies may be made using the hybridoma method first described by Kohler et al., *Nature* 256: 495 (1975), or may be made by recombinant DNA methods (U.S. Pat. No. 4,816,567).

In the hybridoma method, a mouse or other appropriate host animal, such as a hamster or macaque monkey, is immunized as herein above described to elicit lymphocytes that produce or are capable of producing antibodies that will specifically bind to the protein used for immunization. Alternatively, lymphocytes may be immunized in vitro. Lymphocytes or more preferably, lymphocytes enriched for B cells then are fused with myeloma cells by an electrocell fusion process or by using a suitable fusing agent, such as polyethylene glycol, to form a hybridoma cell (Goding, *Monoclonal Antibodies: Principles and Practice*, pp.59-103, [Academic Press, 1996]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and MC.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); Brodeur et al., *Monoclonal Antibody Production Techniques and Applications*, pp. 51-63, Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis of Munson et al., *Anal. Biochem.* 107: 220 (1980).

After hybridoma cells are identified that produce antibodies of the desired specificity, affinity, and/or activity, the cells may be subcloned by limiting dilution procedures and grown by standard methods (Goding, *Monoclonal Antibodies: Principles and Practice*, pp.59-103, Academic Press, 1996). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by covalently joining to the immunoglobulin coding sequence all or part of the coding sequence for a non-immunoglobulin polypeptide. In that manner, "chimeric" or "hybrid" antibodies are prepared that have the binding specificity of an anti-CA IX monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an CA IX and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

(b) Human Antibodies

Attempts to use the same technology for generating human mAbs have been hampered by the lack of a suitable human myeloma cell line. The best results were obtained using heteromyelomas (mouse×human hybrid myelomas) as fusion partners (Kozbor, *J. Immunol.* 133: 3001 (1984); Brodeur, et al., *Monoclonal Antibody Production Techniques and Applications*, pp.51-63, Marcel Dekker, Inc., New York, 1987). Alternatively, human antibody-secreting cells can be immortalized by infection with the Epstein-Barr virus (EBV). However, EBV-infected cells are difficult to clone and usually produce only relatively low yields of immunoglobulin (James and Bell, *J. Immunol. Methods* 100: 5-40 [1987]). In future, the immortalization of human B cells might possibly be achieved by introducing a defined combination of transforming genes. Such a possibility is highlighted by a recent demonstration that the expression of the telomerase catalytic subunit together with the SV40 large T oncoprotein and an oncogenic allele of H-ras resulted in the tumorigenic conversion of normal human epithelial and fibroblast cells (Hahn et al., *Nature* 400: 464-468 [1999]).

It is now possible to produce transgenic animals (e.g. mice) that are capable, upon immunization, of producing a repertoire of human antibodies in the absence of endogenous immunoglobulin production (Jakobovits et al., *Nature* 362: 255-258 [1993]; Lonberg and Huszar, *Int. Rev. Immunol.* 13: 65-93 [1995]; Fishwild et al., *Nat. Biotechnol.* 14: 845-851 [1996]; Mendez et al., *Nat. Genet.* 15: 146-156 [1997]; Green, *J. Immunol. Methods* 231: 11-23 [1999]; Tomizuka et al., *Proc. Natl. Acad. Sci. USA* 97: 722-727 [2000]; reviewed in Little et al., *Immunol. Today* 21: 364-370 [2000]). For example, it has been described that the homozygous deletion of the antibody heavy chain joining region ($J_H$) gene in chimeric and germ-line mutant mice results in complete inhibition of endogenous antibody production (Jakobovits et al., *Proc. Natl. Acad. Sci. USA* 90: 2551-2555 [1993]). Transfer of the human germ-line immunoglobulin gene array in such germ-line mutant mice results in the production of human antibodies upon antigen challenge (Jakobovits et al., *Nature* 362: 255-258 [1993]).

Mendez et al. (*Nature Genetics* 15: 146-156 [1997]) have generated a line of transgenic mice designated as "XenoMouse® II" that, when challenged with an antigen, generates high affinity fully human antibodies. This was achieved by germ-line integration of megabase human heavy chain and light chain loci into mice with deletion into endogenous $J_H$ segment as described above. The XenoMouse® II harbors 1,020 kb of human heavy chain locus containing approximately 66 $V_H$ genes, complete $D_H$ and $J_H$ regions and three different constant regions (μ, δ and γ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Such a XenoMouse may be immunized with an antigen of particular interest. Sera from such immunized animals may be screened for antibody-reactivity against the initial antigen. Lymphocytes may be isolated from lymph nodes or spleen cells and may further be selected for B cells by selecting for CD138-negative and CD19+ cells. In one aspect, such B cell cultures (BCCs) may be fused to myeloma cells to generate hybridomas as detailed above. In another aspect, such B cell cultures may be screened further for reactivity against the initial antigen, preferably CA IX protein. Such screening includes ELISA with CA IX-His protein, a competition assay with known antibodies that bind the antigen of interest, such as antibody G250, and in vitro binding to transiently transfected CHO or other cells that express full length CA IX. Such screens are further described in the Examples. To isolate single B cells secreting antibodies of interest, a CA IX-specific hemolytic plaque assay is performed. Cells targeted for lysis are preferably sheep red blood cells (SRBCs) coated with the CA IX antigen. In the presence of a B cell culture secreting the immunoglobulin of interest and complement, the formation of a plaque indicates specific CA IX-mediated lysis of the target cells. The single antigen-specific plasma cell in the center of the plaque can be isolated and used for isolation of mRNA. Using reverse-transcriptase PCR, the DNA encoding the variable region of the antibody secreted can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, preferably CHO cells, and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

In one particular embodiment, the present invention includes a human anti-CA IX monoclonal antibody heavy chain or a fragment thereof, comprising at least one of the following CDR's (as defined by Kabat et al., *Sequences of Proteins of Immunological Interest*, Fifth Edition, NIH Publication 91-3242, Bethesda Md. (1991), vols. 1-3): (a) CDR1 having the sequence of amino acids 26 to 35 of SEQ ID NOs: 2-6, 24-29 125, 130, 133, 142 or 150, amino acids 20 to 29 of SEQ ID NO: 30, amino acids 26 to 37 of SEQ ID NOs: 8-19, 22, 128, 136, 137, 146 or 153, amino acids 24 to 35 of SEQ ID NO: 21, amino acids 31 to 35 of SEQ ID NOs: 71-73, 77 or 79 or amino acids 31 to 37 of SEQ ID NO: 75; (b) CDR2 having the sequence of amino acids 50 to 65 of SEQ ID NOs: 2-6, amino acids 52 to 67 of SEQ ID NOs: 8-19 or 22, amino acids 50 to 65 of SEQ ID NOs: 21, amino acids 50 to 65 of SEQ ID NOs: 24-29, amino acids 44 to 59 of SEQ ID NO: 30, amino acids 50 to 65 of SEQ ID NOs: 71-73, 77 or 79, amino acids 52 to 67 of SEQ ID NO: 75, 128, 146 or 153, amino acids 52 to 69 of SEQ ID NO: 136, amino acids 52 to 69 of SEQ ID NO: 137 or amino acids 50 to 66 of SEQ ID NO: 125, 130, 133, 142 or 150, and/or (c) CDR3 having the sequence of amino acids 98 to 109 of SEQ ID NO: 2, 4 or 5, amino acids 98 to 111 of SEQ ID NOs: 3 or 6, amino acids 100-114 of SEQ ID NOs: 8, 11 or 16, amino acids 100-112 of SEQ ID NOs: 9, 10, 12, 17, 18 or 19 amino acids 100-109 of SEQ ID NO: 13, amino acids 100-116 of SEQ ID NO: 14, amino acids 100-111 of SEQ ID NO: 15, amino acids 98 to 104 of SEQ ID NO: 21, amino acids 100-106 of SEQ ID NO: 22, amino acids 98 to 111 of SEQ ID NOs: 24, 25, 26, 29, amino acids 98 to 113 of SEQ ID NO: 27, amino acids 98 to 112 of SEQ ID NO: 28, amino acids 92 to 107 of SEQ ID NO: 30, amino acids 98 to 111 of SEQ ID NOs: 71-73, amino acids 100 to 113 of SEQ ID NO: 75, amino acids 98 to 105 of SEQ ID NO: 77, amino acids 98 to 107 of SEQ ID NO: 79, amino acids 102 to 109 of SEQ ID NO: 136 or 137, amino acids 100 to 109 of SEQ ID NO: 128 amino acids 100 to 114 of SEQ ID NO: 153, amino acids 99 to 109 of SEQ ID NO: 130, amino acids 99 to 116 of SEQ ID NO: 150, amino acids 99 to 115 of SEQ ID NO: 133, amino acids 99 to 113 of SEQ ID NO: 125, amino acids 99 to 106 of SEQ ID NO: 142 or amino acids 100 to 111 of SEQ ID NO: 146. The scope of the invention also covers the heavy chain variable domain of such anti-CA IX monoclonal antibodies. Such heavy chain variable domain can include the entire sequence of SEQ ID NOs: 2-6, 8-10, 21-22, 24-30, 71-73, 75, 77, 79, 136, 128, 153, 137, 130, 150, 133, 125, 142 or 146.

In yet another aspect, the invention provides an anti-human CA IX monoclonal antibody light chain or a fragment thereof, comprising the following CDR's: (a) CDR1 having the sequence of amino acids 23 to 39 of SEQ ID NOs: 32-34, amino acids 24 to 35 of SEQ ID NOs: 36-46, amino acids 24 to 34 of SEQ ID NOs: 48-58, 60-64, 66-69; amino acids 24 to 35 of SEQ ID NOs: 81-83 or amino acids 24 to 34 of SEQ ID NOs: 85, 87, or 89 or amino acids 24 to 39 of SEQ ID NO: 162 or 168 (b) CDR2 having the sequence of amino acids 55 to 61 of SEQ ID NOs: 32-34, amino acids 51 to 57 of SEQ ID NOs: 36-46, amino acids 50 to 56 of SEQ ID NOs: 48-58, 60-64 or 66-69; amino acids 51 to 57 of SEQ ID NOs: 81-83,amino acids 50 to 56 of SEQ ID NOs: 85, 87 or 89 or amino acids 55 to 61 of SEQ ID NO: 162 or 168, and/or (c) CDR3 having the sequence of amino acids 94 to 102 of SEQ ID NOs: 32-34, amino acids 90 to 97 of SEQ ID NOs: 36, 38, 40, 44, 45, amino acids 90 to 98 of SEQ ID NOs: 37, 39, 42, 43, amino acids 90 to 99 of SEQ ID NO: 41 or 46, amino acids 88 to 96 of SEQ ID NOs: 48-58, amino acids 89 to 97 of SEQ ID NOs: 60-64 or 66-69, amino acids 90 to 97 of SEQ ID NOs: 81-83, amino acids 89 to 96 of SEQ ID NOs: 85, 87 or 89, amino acids 94 to 103 of SEQ ID NO: 162 or amino acids 94 to 102 of SEQ ID NO: 168. The scope of the invention also covers the light chain variable domain of such anti-CA IX monoclonal antibodies. Such light chain variable domain can include the entire sequence of SEQ ID NOs: 32-34, 36-66, 48-58, 60-64, 66-69, 81-83, 85, 87, 89, 162 or 168.

In a further aspect, the invention provides an anti-human CA IX monoclonal antibody comprising (A) at least one heavy chain or a fragment thereof, comprising the following CDR's: (a) CDR1 having the sequence of amino acids 26 to 35 of SEQ ID NOs: 2-6, 24-29 125, 130, 133, 142, 150, amino acids 20 to 29 of SEQ ID NO: 30, amino acids 26 to 37 of SEQ ID NOs: 8-19, 22, 128, 136, 137, 146 or 153, amino acids 24 to 35 of SEQ ID NO: 21, amino acids 31 to 35 of SEQ ID NOs: 71-73, 77 or 79 or amino acids 31 to 37 of SEQ ID NO: 75; (b) CDR2 having the sequence of amino acids 50 to 65 of SEQ ID NOs: 2-6, amino acids 52 to 67 of SEQ ID NOs: 8-19 or 22, amino acids 50 to 65 of SEQ ID NOs: 21, amino acids 50 to 65 of SEQ ID NOs: 24-29, amino acids 44 to 59 of SEQ ID NO: 30, amino acids 50 to 65 of SEQ ID NOs: 71-73, 77 or 79, amino acids 52 to 67 of SEQ ID NO: 75, 128, 146 or 153, amino acids 52 to 69 of SEQ ID NO: 136, amino acids 52 to 69 of SEQ ID NO: 137 or amino acids 50 to 66 of SEQ ID NO: 125, 130, 133, 142 or 150, and/or (c) CDR3 having the sequence of amino acids 98 to 109 of SEQ ID NO: 2, 4 or 5, amino acids 98 to 111 of SEQ ID NOs: 3 or 6, amino acids 100-114 of SEQ ID NOs: 8, 11 or 16, amino acids 100-112 of SEQ ID NOs: 9, 10, 12, 17, 18 or 19 amino acids 100-109 of SEQ ID NO: 13, amino acids 100-116 of SEQ ID NO: 14, amino acids 100-111 of SEQ ID NO: 15, amino acids 98 to 104 of SEQ ID NO: 21, amino acids 100-106 of SEQ ID NO: 22, amino acids 98 to 111 of SEQ ID NOs: 24, 25, 26, 29, amino acids 98 to 113 of SEQ ID NO: 27, amino acids 98 to 112 of SEQ ID NO: 28, amino acids 92 to 107 of SEQ ID NO: 30, amino acids 98 to 111 of SEQ ID NOs: 71-73, amino acids 100 to 113 of SEQ ID NO: 75, amino acids 98 to 105 of SEQ ID NO: 77, amino acids 98 to 107 of SEQ ID NO: 79, amino acids 102 to 109 of SEQ ID NO: 136 or 137, amino acids 100 to 109 of SEQ ID NO: 128 amino acids 100 to 114 of SEQ ID NO: 153, amino acids 99 to 109 of SEQ ID NO: 130, amino acids 99 to 116 of SEQ ID NO: 150, amino acids 99 to 115 of SEQ ID NO: 133, amino acids 99 to 113 of SEQ ID NO: 125, amino acids 99 to 106 of SEQ ID NO: 142 or amino acids 100 to 111 of SEQ ID NO: 146, and/or (B) at least one light chain or a fragment thereof, comprising the following CDR's: (a) CDR1 having the sequence of amino acids 23 to 39 of SEQ ID NOs: 32-34, amino acids 24 to 35 of SEQ ID NOs: 36-46, amino acids 24 to 34 of SEQ ID NOs: 48-58, 60-64, 66-69; amino acids 24 to 35 of SEQ ID NOs: 81-83 or amino acids 24 to 34 of SEQ ID NOs: 85, 87, or 89 or amino acids 24 to 39 of SEQ ID NO: 162 or 168 (b) CDR2 having the sequence of amino acids 55 to 61 of SEQ ID NOs: 32-34, amino acids 51 to 57 of SEQ ID NOs: 36-46, amino acids 50 to 56 of SEQ ID NOs: 48-58, 60-64 or 66-69; amino acids 51 to 57 of SEQ ID NOs: 81-83,amino acids 50 to 56 of SEQ ID NOs: 85, 87 or 89 or amino acids 55 to 61 of SEQ ID NO: 162 or 168, and/or (c) CDR3 having the sequence of amino acids 94 to 102 of SEQ ID NOs: 32-34, amino acids 90 to 97 of SEQ ID NOs: 36, 38, 40, 44, 45, amino acids 90 to 98 of SEQ ID NOs: 37, 39, 42, 43, amino acids 90 to 99 of SEQ ID NO: 41 or 46, amino acids 88 to 96 of SEQ ID NOs: 48-58, amino acids 89 to 97 of SEQ ID NOs: 60-64 or 66-69, amino acids 90 to 97 of SEQ ID NOs: 81-83, amino acids 89 to 96 of SEQ ID NOs: 85, 87 or 89, amino acids 94 to 103 of SEQ ID NO: 162 or amino acids 94 to 102 of SEQ ID NO: 168. In one aspect, the present invention includes antibodies generated such as AB-MN-21.5.2, AB-MN-21.6.1, AB-MN-22.7, AB-MN-22.8.1, AB-MN-21.17.1, AB-MN-21.8.1, AB-MN-22.11, AB-MN-22.19, AB-MN-22.26, AB-MN-22.27, AB-MN-22.3, AB-MN-22.4, AB-MN-22.5, AB-MN-22.9, AB-MN-21.2.1, AB-MN-21.7.1, AB-MN-22.10, AB-MN-22.14, AB-MN-22.18, AB-MN-22.20, AB-MN-22.21, AB-MN-22.24, AB-MN-22.25, AB-MN-22.28.1, AB-MN-22.30, AB-MN-21.1.1, AB-MN-21.14.1, AB-MN-22.12, AB-MN-22.17, AB-MN-22.29, AB-MN-21.9.1, AB-MN-22.15, AB-MN-22.16, AB-MN-22.23, AB-MN-22.17.1, AB-MN-21.10.1, AB-MN-22.10, AB-MN-22.14, AB-MN-22.20, AB-MN-22.24, AB-MN-22.28.1, AB-AN-22.30, AB-MN-22.7, AB-MN-21.8.1, AB-MN-22.4 and AB-MN-22.13.1 wherein the "AB-MN-21." and "AB-MN-22." designations represent the fact that the antibody was isolated from IgG1 Xenomice or IgG2 Xenomice, respectively, that were immunized with CA IX antigen. The B cells were isolated from the immunized Xenomice and cultured in vitro or fused with a myeloma cell. As described above, the supernatants from the B cell cultures were analyzed for CA IX antibodies. Using a rosette assay, the one B cell making the desired anti-CA IX antibody was identified and the RNA was isolated. The mRNA encoding for the desired antibody was cloned and expressed in a CHO cell. Alternatively, the antibody containing supernates from the myeloma fusion were screened directly using an ELISA assay. The number following "AB-MN-21." or "AB-MN-22.", for example the "21.5.2" in "AB-MN-21.5.2", correlates with the sequence identifed from a hybridoma cell derived from an IgG1 xenomouse. The designation AB-MN 22_indicates that the sequence was derived from a hybridoma derived from an IgG2 immunized mouse. Further, the number following "AX014H", for example the 21_5_2 in "AX014H21_5_2" also correlates with the sequence identified as single cell "21.5.2." The present invention further includes antibodies, such as AB-MN-XG2-109, AB-MN-XG2-051, AB-MN-XG2-023, AB-MN-XG1-080, AB-MN-XG1-141, AB-MN-XG1-174, AB-MN-XG2-109, AB-MN-XG2-051 and AB-MN-XG2-023. "XG1" and "XG2" antibodies were generated by taking lymphocytes from Xenomice immunized with CA IX. The lymphocytes were fused with myeloma cells to generate hybridomas expressing the CA IX antibodies as described above. The CDR and FR regions in the variable regions of the AB-MN-XG1-109 and AB-MN-XG2-109 are identical. The CDR and FR regions in the variable regions of the AB-MN-XG1-051 and AB-MN-XG2-051 are identical. The CDR and FR regions in the variable regions of the AB-MN-XG1-023 and AB-MN-XG2-023 are identical.

(1) Antibodies from Hybridomas

The amino acid sequence of the heavy chain and light chain variable region, having V, D and partial J regions or AB-MN-21.5.2 are represented by SEQ ID NO: 9 as shown in FIGS. 3A-3B and SEQ ID NO: 32 as shown in FIG. 8, respectively, for AB-MN-21.6.1 are represented by SEQ ID NO: 10 as shown in FIG. 3 and SEQ ID NO: 33 as shown in FIG. 8, respectively, for AB-MN-22.8.1 are represented by SEQ ID NO: 30 as shown in FIG. 6 and SEQ ID NO: 36 as shown in FIG. 10, respectively, for AB-MN-21.17.1 are represented by SEQ ID NO: 2 as shown in FIG. 1 and SEQ ID NO: 37 as shown in FIG. 10, respectively, for AB-MN-22.11 are represented by SEQ ID NO: 13 as shown in FIG. 3 and SEQ ID NO: 39 as shown in FIG. 10, respectively, for AB-MN-22.19 are represented by SEQ ID NO: 3 as shown in FIG. 1 and SEQ ID NO: 40 as shown in FIG. 10, respectively, for AB-MN-21.6.1 are represented by SEQ ID NO: 10 as shown in FIG. 3 and SEQ ID NO: 33 as shown in FIG. 8, respectively, for AB-MN-22.26 are represented by SEQ ID NO: 28 as shown in FIG. 6 and SEQ ID NO: 41 as shown in FIG. 10, respectively, for AB-MN-22.27 are represented by SEQ ID NO: 29 as shown in FIG. 6 and SEQ ID NO: 42 as shown in FIG. 10, respectively, for AB-MN-22.3 are represented by SEQ ID NO: 5 as shown in FIG. 1 and SEQ ID NO: 43 as shown in FIG. 10, respectively, for AB-MN-22.5 are represented by SEQ ID NO: 6 as shown in FIG. 1 and SEQ ID NO: 45 as shown in FIG. 10, respectively and for AB-MN-22.9 are represented by SEQ ID NO: 19 as shown in FIG. 3 and SEQ ID NO: 46 as shown in FIG. 10, respectively.

The amino acid sequence of the heavy chain and light chain variable region for AB-MN-21.2.1 are represented by SEQ ID NOs: 8 as shown in FIGS. 3A-3B and SEQ ID NO:

48 as shown in FIG. 12, respectively, for AB-MN-21.7.1 are represented by SEQ ID NOs: 11 as shown in FIGS. 3A-3B and SEQ ID NO: 49 as shown in FIG. 12, respectively, for AB-MN-22.18 are represented by SEQ ID NOs: 16 as shown in FIGS. 3A-3B and SEQ ID NO: 52 as shown in FIG. 12, respectively, for AB-MN-22.21 are represented by SEQ ID NOs: 17 as shown in FIGS. 3A-3B and SEQ ID NO: 54 as shown in FIG. 12, respectively, for AB-MN-22.25 are represented by SEQ ID NOs: 22 as shown in FIG. 5 and SEQ ID NO: 56 as shown in FIG. 12, respectively.

The amino acid sequence of the heavy chain and light chain variable regions for AB-MN-21.1.1 are represented by SEQ ID NOs: 24 as shown in FIG. 6 and SEQ ID NO: 60 as shown in FIG. 14, respectively, for AB-MN-21.14.1 are represented by SEQ ID NOs: 25 as shown in FIG. 6 and SEQ ID NO: 61 as shown in FIG. 14, respectively, for AB-MN-22.12 are represented by SEQ ID NOs: 26 as shown in FIG. 6 and SEQ ID NO: 62 as shown in FIG. 16, respectively and for AB-MN-22.17 are represented by SEQ ID NO: 27 as shown in FIG. 6 and SEQ ID NO: 63 as shown in FIG. 16, respectively.

The amino acid sequence of the heavy chain and light chain variable domain for AB-MN-21.9.1 is represented by SEQ ID NOs: 12 as shown in FIGS. 3A-3B and SEQ ID NO: 66 as shown in FIG. 16, respectively, for AB-MN-22.15 is represented by SEQ ID NOs: 14 as shown in FIGS. 3A-3B and SEQ ID NO: 67 as shown in FIG. 16, respectively, for AB-MN-22.16 is represented by SEQ ID NOs: 15 as shown in FIGS. 3A-3B and SEQ ID NO: 68 as shown in FIG. 16, respectively, and for AB-MN-22.23 is represented by SEQ ID NO: 18 as shown in FIGS. 3A-3B, AB-MN-22.29 are represented by SEQ ID NO: 4, as shown in FIG. 1 and SEQ ID NO: 69 as shown in FIG. 14, respectively, for AB-MN-22.17.1 are represented by SEQ ID NO: 102 and SEQ ID NO: 103, respectively, for AB-MN-21.10.1 are represented by SEQ ID NO: 21 as shown in FIG. 5 and SEQ ID NO: 162 as shown in FIGS. 28A-B, respectively and for AB-MN-22.13.1 are represented by SEQ ID NO: 146 as shown in FIGS. 27A-B and SEQ ID NO: 168 as shown in FIGS. 29A-B, respectively.

The amino acid sequence of the light chain variable region for AB-MN-22.10 is represented by SEQ ID NO: 50 as shown in FIG. 12, for AB-MN-22.14 is represented by SEQ ID NO: 51 as shown in FIG. 12, for AB-MN-22.20 is represented by SEQ ID NO: 53 as shown in FIG. 12, for AB-MN-22.24 is represented by SEQ ID NO: 55 as shown in FIG. 12, for AB-MN-22.28.1 is represented by SEQ ID NO: 57 as shown in FIG. 12, for AB-MN-22.30 is represented by SEQ ID NO: 58 as shown in FIG. 12, for AB-MN-22.7 is represented by SEQ ID NO: 34 as shown in FIG. 8, for AB-MN-21.8.1 is represented by SEQ ID NO: 38 as shown in FIG. 10 and for AB-MN-22.4 is represented by SEQ ID NO: 44 as shown in FIG. 10.

The amino acid sequence of the heavy chain variable region for AB-MN-22.10, AB-MN-22.14, AB-MN-22.20, AB-MN-22.24, AB-MN-22.28.1, AB-MN-22.30, AB-MN-22.7, AB-MN-21.8.1 and AB-MN-22.4 are represented by the sequences of SEQ ID NO: 136 as shown in FIGS. 26A-B, SEQ ID NO: 128 as shown in FIGS. 26A-B, SEQ ID NO: 153 as shown in FIGS. 27A-B, SEQ ID NO: 137 as shown in FIGS. 26A-B, SEQ ID NO: 130 as shown in FIGS. 26A-B, SEQ ID NO: 150 as shown in FIGS. 27A-B, SEQ ID NO: 133 as shown in FIGS. 26A-B, SEQ ID NO: 125 as shown in FIGS. 26A-B, SEQ ID NO: 142 as shown in FIG. 26A.

The amino acid sequence of the heavy chain variable domain of the Vgamma/D/J germline sequence of VH4-4, VH4-31, VH4-39 and VH4-59 are represented by SEQ ID NOs: 1 as shown in FIG. 1, SEQ ID NO: 7 as shown in FIGS. 3A-3B, SEQ ID NO: 20 as shown in FIG. 5 and SEQ ID NO: 23 as shown in FIG. 6, respectively. The amino acid sequence of the light chain variable domain of the Vkappa/J germline sequence of VK-A19, VK-A27, VK-A30, VK-L5 and VK-O12 are represented by SEQ ID NO: 31 as shown in FIG. 8, SEQ ID NO: 35 as shown in FIG. 10, SEQ ID NO: 47 as shown in FIG. 12, SEQ ID NO: 59 as shown in FIG. 14 and SEQ ID NO: 65 as shown in FIG. 16, respectively.

The amino acid sequence and encoding nucleotide sequence of the heavy chain variable domain, which includes the signal peptide and additional carboxy-terminal sequence, for AB-MN-22.13.1 are represented by SEQ ID Nos: 169 and 170, respectively. The amino acid sequence and encoding nucleotide sequence of the heavy chain variable domain, which includes the additional carboxy-terminal sequence, for AB-MN-22.8.1 are represented by SEQ ID Nos: 171 and 172, respectively. The amino acid sequence and encoding nucleotide sequence of the heavy chain variable domain, which includes additional carboxy-terminal sequence, for AB-MN-21.10.1 are represented by SEQ ID Nos: 173 and 174, respectively. The amino acid sequence and encoding nucleotide sequence of the heavy chain variable domain, which includes additional carboxy-terminal sequence, for AB-MN-22.28.1 are represented by SEQ ID Nos: 246 and 245, respectively.

The amino acid sequence and encoding nucleotide sequence of the light chain variable domain, which includes the signal peptide and additional carboxy-terminal sequence, for AB-MN-22.13.1 are represented by SEQ ID Nos: 175 and 176, respectively. The amino acid sequence and encoding nucleotide sequence of the light chain variable domain, which includes the additional carboxy-terminal sequence, for AB-MN-22.8.1 are represented by SEQ ID Nos: 177 and 178, respectively. The amino acid sequence and encoding nucleotide sequence of the light chain variable domain, which includes the signal peptide and additional carboxy-terminal sequence, for AB-MN-21.10.1 are represented by SEQ ID Nos: 179 and 180, respectively. The amino acid sequence and encoding nucleotide sequence of the light chain variable domain, which includes the signal peptide and additional carboxy-terminal sequence, for AB-MN-22.28..1 are represented by SEQ ID NOs: 245 and 237, respectively.

The nucleotide sequence encoding for the heavy chain and light chain variable regions for AB-MN-21.14.1 are represented by SEQ ID NOs: 181 and 213, respectively, for AB-MN-21.17.1 are represented by SEQ ID NO: 182 and 214, respectively, for AB-MN-21.1.1 are represented by SEQ ID NO: 183 and 215, respectively, for AB-MN-21.2.1 are represented by SEQ ID NO: 184 and 216, respectively, for AB-MN-21.5.2 are represented by SEQ ID NO: 185 and 217, respectively, for AB-MN-21.6.1 are represented by SEQ ID NO: 186 and 218, respectively, for AB-MN-21.7.1 are represented by SEQ ID NO: 187 and 219, respectively, for AB-MN-21.8.1 are represented by SEQ ID NO: 188 and 220, respectively, for AB-MN-21.9.1 are represented by SEQ ID NO: 189 and 221, respectively, for AB-MN-22.10 are represented by SEQ ID NO: 190 and 222, respectively, for AB-MN-22.11 are represented by SEQ ID NO: 191 and 223, respectively, for AB-MN-22.12 are represented by SEQ ID NO: 192 and 224, respectively, for AB-MN-22.14 are represented by SEQ ID NO: 193 and 225, respectively, for AB-MN-22.15 are represented by SEQ ID NO: 194 and 226, respectively, for AB-MN-22.16 are represented by SEQ ID NO: 195 and 227, respectively, for AB-MN-22.17 are represented by SEQ ID NO: 196 and 228, respectively, for AB-MN-22.18 are represented by SEQ ID NO: 197 and 229, respectively, for AB-MN-22.19 are represented by SEQ ID NO: 198 and 230, respectively, for AB-MN-22.20 are represented by SEQ ID NO: 199 and 231, respectively, for AB-MN-22.21 are represented by SEQ ID NO: 200 and 232, respectively, for AB-MN-22.23 are represented by SEQ ID NO: 201 and 233, respectively, for AB-MN-22.24 are represented by SEQ ID NO: 202 and 234, respectively, for AB-MN-22.25 are represented by SEQ ID NO: 203 and 235, respectively, for AB-MN-22.26 are represented by SEQ ID NO: 204 and 236, respectively, for AB-MN-22.27 are represented by SEQ ID NO: 116 and 117, respectively, for AB-MN-22.28.1 are represented by SEQ ID NO: 205 and 237, respectively, for AB-MN-22.29 are represented by SEQ ID NO: 206 and 238, respectively, for AB-MN-22.30 are represented by SEQ ID NO: 207 and 239, respectively, for AB-MN-22.3 are represented by SEQ ID NO: 208 and 240, respectively, for AB-MN-22.4 are represented by SEQ ID NO: 209 and 241, respectively, for AB-MN-22.5 are represented by SEQ ID NO: 210 and 242, respectively, for AB-M-22.7 are represented by SEQ ID NO: 211 and 243, respectively, for AB-MN-22.9 are represented by SEQ ID NO: 212 and 244, respectively. The nucleotide sequence of the heavy chain and light chain variable region for AB-MN-22.27 are represented by SEQ ID NOs: 116 and 117, respectively and for AB-MN-22.17.1 are represented by SEQ ID NOs: 118 and 119, respectively.

Figure 4:
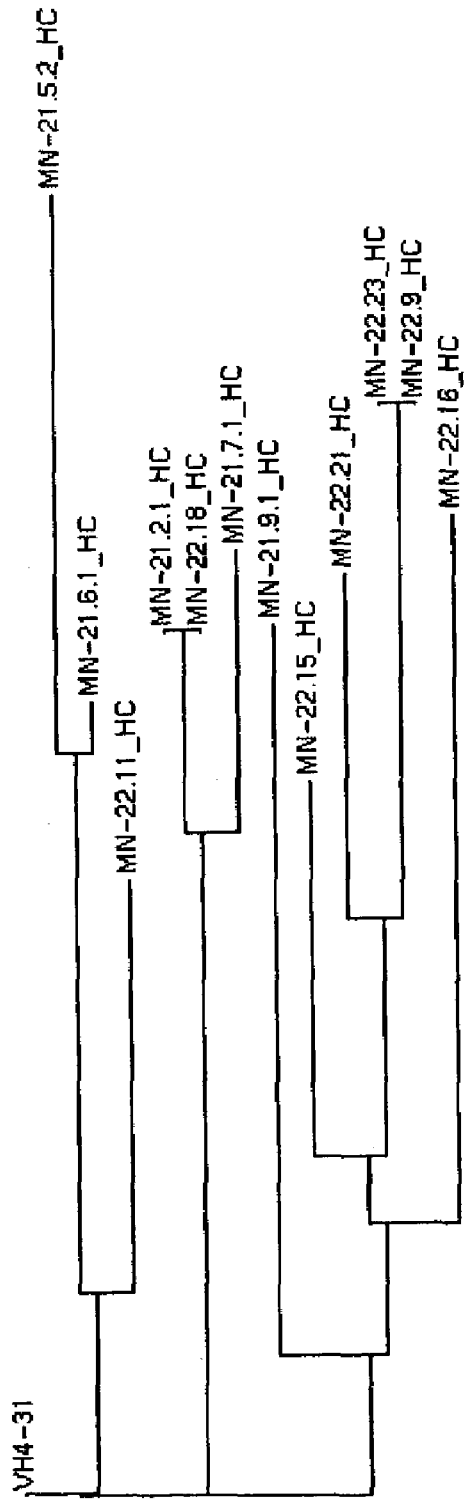
FIG. 4 shows a dendrogram representing the hierarchy of the anti-CA IX immunoglobulins, AB-MN-21.2.1_HC, AB-MN-21.5.1_HC, AB-MN-21.6.1_HC, AB-MN-21.7.1_HC, AB-MN-21.9.1_HC, AB-MN-22.11_HC, AB-MN-22.15_HC, AB-MN-22.16_HC, AB-MN-22.18_HC, AB-MN-22.21_HC, AB-MN-22.23_HC and AB-MN-22.9_HC based on their similarity with the variable heavy chain region, VH4-31.
Figure 7:
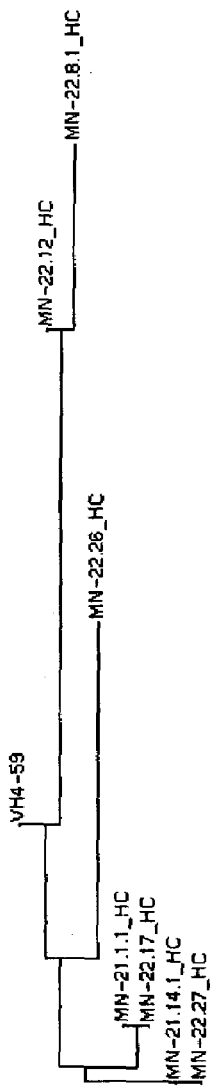
FIG. 7 shows a dendrogram representing the hierarchy of the anti-CA IX immunoglobulins, AB-MN-21.1.1_HC, AB-MN-21.14.1_HC, AB-MN-22.12_HC, AB-MN-22.17_HC, AB-MN-22.26_HC, AB-MN-22.27_HC and AB-MN-22.8.1_HC based on their similarity with the variable heavy chain region of VH4-59.

Dendrograms representing the hierarchy of anti-CA IX antibodies with a particular germline rearrangement, such as Vgamma/D/J germline sequence of VH4-4, VH4-31 and VH4-59 are shown in FIGS. 2, 4, 7, respectively and Vkappa/J germline sequence of VK-A19, VK-A27, VK-A30, VK-L5 and VK-O12 are shown in FIGS. 9, 11, 13, 15 and 17, respectively.

(2) Antibodies from XenoMax

The amino acid sequence of the heavy chain and light chain variable with the signal sequence for AB-MN-XG1-080 is represented by SEQ ID NOs: 71 and 81, respectively, for AB-MN-XG1-141 is represented by SEQ ID NOs: 72 and 82, respectively, for AB-MN-XG1-174 is represented by SEQ ID NOs: 73 and 83, respectively, for AB-MN-XG1-23 is represented by SEQ ID NOs: 75 and 85, respectively, for AB-MN-XG1-51 is represented by SEQ ID NOs: 77 and 87, respectively, and for AB-MN-XG1-109 is represented by SEQ ID NOs: 79 and 89, respectively. The amino acid sequence of the heavy chain variable domain of the Vgamma/D/J germline sequence of VH4-59/D3-3/JH6b, VH4-30.1/D3-9/JH5b, VH3-21/D5-18/JH4b and VH4-04/D1-20/JH6b are represented as shown in FIG. 18 by SEQ ID NOs: 70, 74, 76 and 78, respectively. The amino acid sequence of the light chain variable domain of the Vkappa/J germline sequence of A27/JK4, L19/JK1, A20/JK1 and O2/JK3 are represented as shown in FIG. 19 by SEQ ID NOs: 80, 84, 86 and 88.

The amino acid sequence of the entire heavy chain variable domain for AB-MN-XG1-080, AB-MN-XG1-141, AB-MN-XG1-174, AB-MN-XG1-023, AB-MN-XG1-051 and AB-MN-XG1-109 are represented by SEQ ID NOs: 90, 92, 94, 96, 98 and 100, respectively. The nucleotide sequence of the entire heavy chain variable domain for AB-MN-XG1-080, AB-MN-XG1-141, AB-MN-XG1-174, AB-MN-XG1-023, AB-MN-XG1-051 and AB-MN-XG1-109 are represented by SEQ ID NOs: 104, 106, 108, 110, 112 and 114, respectively.

The amino acid sequence of the entire light chain variable domain for AB-MN-XG1-080, AB-MN-XG1-141, AB-MN-XG1-174, AB-MN-XG1-023, AB-MN-XG1-051 and AB-MN-XG1-109 are represented by SEQ ID NOs: 91, 93, 95, 97, 99 and 101, respectively. The nucleotide sequence of the entire light chain variable domain for AB-MN-XG1-080, AB-MN-XG1-141, AB-MN-XG1-174, AB-MN-XG1-023, AB-MN-XG1-051 and AB-MN-XG1-109 are represented by SEQ ID NOs: 105, 107, 109, 111, 113, and 115, respectively.

2. Screening for Antibodies with the Desired Properties (i) Binding to CA IX Antigen Thus, for example, the anti-CA IX antibodies of the present invention can be identified by incubating a B cell culture or hybridoma supernatant with purified protein from the extracellular domain of CA IX (amino acids 1-413) that has been bound to a microtiter plate. Specific binding can be detected after washing and adding HRP conjugated goat anti-human Fc antibody and determining the optical density with a plate reader set at OD 492 nm.

In another embodiment B cell culture or hybridoma supernatants can be incubated with CHO cells transiently lipofected with full length MN, or more preferably to the catalytic domain of MN, that have been trypsinized and seeded in dishes. After washing, a secondary labeled antibody specific for anti-human IgG Fc is subsequently incubated to allow visualization of binding by fluorescent microscopy.

In one embodiment, the binding assay is a competitive binding assay, where the ability of a candidate antibody to compete with a known anti-CA IX antibody, such as G250, is evaluated. The assay may be performed in various formats, including the ELISA format also illustrated in the Examples below.

Any suitable competition binding assay known in the art can be used to characterize the ability of a candidate anti-CA IX monoclonal antibody to compete with anti-G250 antibody for binding to CA IX antigen. A routine competition assay is described in *Antibodies: A Laboratory Manual*, Cold Spring Harbor Laboratory, Ed Harlow and David Lane (1988). In another embodiment, the CA IX-binding ELISA assay described in Example 2 below could be modified to employ CA IX binding competition between a candidate antibody and another known CA IX binding antibody such as G250. Such an assay could be performed by layering the CA IX on microtiter plates, incubating the layered plates with serial dilutions of unlabeled anti-CA IX antibody or unlabeled control antibody admixed with a select concentration of labeled G250, detecting and measuring the signal from the G250 antibody label, and then comparing the signal measurements exhibited by the various dilution of antibody.

(ii) Inhibition of Biological Activity of CA IX

An important role of carbonic anhydrases such as CA IX in tumors may include a role in tumor survival or progression. The catalytic activity of CA IX includes the conversion of $CO_2$ and $H_2O$ to carbonic acid. The presence of CA IX on primarily carcinoma cell lines and malignant tissues, but not in corresponding normal tissues, suggests a possible role for the enzymatic activity of CA IX in tumor progression, more specifically a role in maintaining the characteristic extracellular acidosis and intracellular alkalosis of tumor cells. This low extracellular pH may serve to protect tumor cells from the infiltration and destructive capabilities of immune cells. Thus inhibition of CA IX by anti-CA IX antibodies may cause tumors to be more susceptible to the normal defense characteristics of the immune system as well as to other standard chemotherapy or antibody based tumor treatments.

In one embodiment, the antibodies of the present invention are subjected to a spectrophotometric assay to assess the ability to inhibit carbonic anydrase activity of CA IX. For example, the substrates of CA IX, $CO_2$ and $H_2O$, are incubated either in the presence or absence (control) of CA IX with phenol red. The absorption of the solution at 558 nm is determined by a spectrophotometer. The time difference for the complete hydration of $CO_2$ and conversion of the solution from a red to a yellow color can be determined by a concomitant change in absorption at 558 nm. The difference between the control and control plus CA IX enzyme indicates the activity of carbonic anhydrase. To test the effect of a candidate antibody on CA IX enzymatic activity, the antibody is incubated with the CA IX prior to addition of the CA IX substrates.

In another embodiment, the antibodies of the present invention are tested for the ability to disrupt normal CA IX activity at the site of tumor progression. Normal CA IX activity includes enzymatic activity converting water and carbon dioxide into carbonic acid. The internalization of CA IX normally present on the surface of tumor cells blocks the ability of the enzyme to perform its normal function. Accordingly, the removal of CA IX activity following internalization may cause the tumor to be more susceptible to the immune system as well as to other chemotherapy or antibody based tumor treatments. Preferably, screening of candidate anti-CA IX antibodies for internalization is performed by incubating with cells, such as SKRC10 cells. A labeled secondary antibody is added and internalization is initiated by shifting the cells to 37° C. The level of cell surface and internalized anti-CA IX antibody is determined by fluorescent microscopy.

In another embodiment, the disruption of proliferation of cells is another possible use for anti-CA IX cells in tumor treatment. An antiproliferative affect of anti-CA IX antibodies would be useful for inhibiting the proliferation of tumor or cancer cells which is important for disease progression. To determine the effect of anti-CA IX antibodies of the present invention on cell proliferation of cells, such as HeLa or MDA468, expressing endogenous CA IX, are assayed for integrity of mitochondrial function. Metabolically active cells with proper mitochondrial function are able to reduce the substrate MTS tetrazolium compound (ProMega) into a colored product that is soluble in tissue culture media and has a characteristic absorbance at 490 nm. The conversion is presumably accomplished by NADPH or NADH produced by dehydrogenase enzymes in metabolically active cells. A decrease in mitochondrial function of such CA IX-expressing cells may lead to a decrease in cell viability under stressful conditions.

(iii) Mediation of ADCC

Antibody-dependent cell-mediated cytotoxicity (ADCC) is the killing of antibody-coated target cells by cells with Fc receptors that recognize the Fc region of the bound antibody. Most ADCC is mediated by natural killer (NK) cells that have the Fc receptor FcγRIII or CD16 on their surface. The ability of the present anti-CA IX antibodies to mediate ADCC may be of use as tumor treatments. In one embodiment, target cells, such as HT-29 or SK-RC-52 cells, a human renal cell carcinoma cell line, are labeled with a fluorescent Europium (EuDTPA). Candidate antibodies were diluted and aliquotted into microtiter plates. Target cells are preferably incubated with the antibodies for a period prior to the addition of effector peripheral blood mononuclear cells (PMBC). The ability of anti-CA IX cells to induce lysis of such target cells by inducing the response of PBMCs is measured by the release of EuDTPA into the supernatant using a Multilabel counter.

3. Therapeutic Compositions and Administration of Anti-CA IX Antibodies

Therapeutic formulations of the anti-CA IX antibodies of the invention are prepared for storage by mixing antibody having the desired degree of purity with optional physiologically acceptable carriers, excipients, or stabilizers (*Remington: The Science and Practice of Pharmacy,* 19th Edition, Alfonso, R., ed, Mack Publishing Co. (Easton, Pa.: 1995)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The anti-CA IX antibody to be used for in vivo administration must be sterile. This is readily accomplished by filtration through sterile filtration membranes, prior to or following lyophilization and reconstitution. The anti-CA IX antibody ordinarily will be stored in lyophilized form or in solution.

Therapeutic anti-CA IX antibody compositions generally are placed into a container having a sterile access port, for example, an intravenous solution bag or vial having a stopper pierceable by a hypodermic injection needle.

The route of anti-CA IX antibody administration is in accord with known methods, e.g. injection or infusion by intravenous, intraperitoneal, intracerebral, subcutaneous, intramuscular, intraocular, intraarterial, intracerebrospinal, or intralesional routes, or by sustained release systems as noted below. Preferably the antibody is given systemically.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547-556 (1983)), poly (2-hydroxyethyl-methacrylate) (Langer et al., *J. Biomed. Mater. Res.,* 15: 167-277 (1981) and Langer, *Chem. Tech.,* 12: 98-105 (1982)), ethylene vinyl acetate (Langer et al., supra) or poly-D-(−)-3-hydroxybutyric acid (EP 133,988). Sustained-release anti-CA IX antibody compositions may also include liposomally entrapped antibody. Liposomes containing antibody are prepared by methods known per se: DE 3,218,121; Epstein et al., *Proc. Natl. Acad. Sci. USA,* 82: 3688-3692 (1985); Hwang et al., *Proc. Natl. Acad. Sci. USA,* 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mol. % cholesterol, the selected proportion being adjusted for the optimal antibody therapy.

Anti-CA IX antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-CA IX antibody can be aerosolized using a fluorocarbon formulation and a metered dose inhaler, or inhaled as a lyophilized and milled powder.

An “effective amount” of anti-CA IX antibody to be employed therapeutically will depend, for example, upon the therapeutic objectives, the route of administration, the type of anti-CA IX antibody employed, and the condition of the patient. Accordingly, it will be necessary for the therapist to titer the dosage and modify the route of administration as required to obtain the optimal therapeutic effect. Typically, the clinician will administer the anti-CA IX antibody until a dosage is reached that achieves the desired effect. The progress of this therapy is easily monitored by conventional assays.

Antibodies specific to tumor antigens such as anti-CA IX are useful in targeting of tumor cells for destruction. For example, ricin, a cellular toxin, is finding unique applications, especially in the fight against tumors and cancer. Implications are being discovered as to the use of ricin in the treatment of tumors. Ricin has been suggested to have a greater affinity for cancerous cells than normal cells (Montfort et al. 1987) and has been often termed as a “magic bullet” for targeting malignant tumors. Toxins such as ricin remain active even if the B chain of the toxin is removed. Accordingly, if the solitary A chain is coupled to a tumor-specific antibody, such as anti-CA IX antibody, the toxin has a specific affinity for cancerous cells over normal cells (Taylorson 1996). For example, ricin immunotoxin has been developed to target the CD5 T-cell antigen often found in T-cell and B-cell malignancies (Kreitman et al. 1998). Other types of toxins such as calichaemycin, geldanamycin and maytansine have also been show to be effective for treating cancerous cells and these type of molecules could be conjugated to anti-CA-IX antibodies (Proc. Natl. Acad. Sci USA 93: 8618, 1996; J. Ntl Cancer Inst.92: 1573, 2000; Cancer Res. 60: 6089, 2000). Further, the linking of such anti-CA IX antibodies to radioisotopes provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. With this “magic bullet,” the patient can be treated with much smaller quantities of radioisotopes than other forms of treatment available today.

The patients to be treated with the anti-CA IX antibody of the invention include patients or those with tumors, such as esophageal, pancreatic, colorectal tumors, carcinomas, such as renal cell carcinoma (RCC), cervical carcinomas and cervical intraepithelial squamous and glandular neoplasia, and cancers, such as colorectal cancer, breast cancer, lung cancer, and other malignancies. Patients are candidates for therapy in accord with this invention until such point as no healthy tissue remains to be protected from tumor progression. It is desirable to administer an anti-CA IX antibody as early as possible in the development of the tumor, and to continue treatment for as long as is necessary.

In the treatment and prevention of tumor-associated disorder by an anti-CA IX antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The “therapeutically effective amount” of antibody to be administered will be governed by such considerations, and is the minimum amount necessary to prevent, ameliorate, or treat the disorder, including treating chronic autoimmune conditions and immunosuppression maintenance in transplant recipients. Such amount is preferably below the amount that is toxic to the host or renders the host significantly more susceptible to infections.

As a general proposition, the initial pharmaceutically effective amount of the antibody administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of antibody, depending on the pattern of pharmacokinetic decay that the practitioner wishes to achieve.

As noted above, however, these suggested amounts of antibody are subject to a great deal of therapeutic discretion. The key factor in selecting an appropriate dose and scheduling is the result obtained, as indicated above. For example, the antibody may be optionally formulated with one or more agents currently used to prevent or treat tumors such as standard- or high-dose chemotherapy and hematopoietic stem-cell transplantation. The effective amount of such other agents depends on the amount of anti-CA IX antibody present in the formulation, the type of disorder or treatment, and other factors discussed above. These are generally used in the same dosages and with administration routes as used hereinbefore or about from 1 to 99% of the heretofore employed dosages.

Further details of the invention can be found in the following example, which further defines the scope of the invention. All references cited throughout the specification, and the references cited therein, are hereby expressly incorporated by reference in their entirety.

EXAMPLE 1

Preparation of CA IX Tumor Antigens

In the present study, recombinant CA IX proteins were prepared. The full length CA IX cDNA was cloned by Reverse Transcriptase-PCR (RT-PCR) from human HT-29 cells (ATCC) with primers based on the sequence of Pastorek et al (*Oncogene* 9: 2877-2888 (1994)) NCBI Accession #X66839.

The primers used for the amplification of full length (FL) CA IX are as follows:

Forward primer: 5'-GTACACACCGTGTGCTGGGAC-3' (SEQ ID NO: 120)

Reverse primer: 5'-CCTCAGATGCCTCTGGCTGG-3' (SEQ ID NO: 121)

The ~1.5 kb PCR product was cloned into pCR3.1 UNI (Invitrogen). Clone #15 was used as a template for PCR amplification of the extracellular domain (aa1-413 of CA IX with the following primers that incorporate a SalI site in the forward primer and a NheI site in the reverse primer):

Forward primer 5'-ATATTACGTCGACGTACACACCGTGTGCTGGAC-3' (SEQ ID NO: 122)

Reverse primer 5'-CAGCTTAGAGCTAGCCCAGCAGCCAGGCAGGAATTCAGC-3' (SEQ ID NO: 123)

The PCR product was digested with SalI and NheI and ligated into CD147HuIgG2 DHFR expression vector (Abgenix, Fremont, Calif.) digested with SalI and NheI. Plasmids were transfected into 293 cells using a CaPO$_4$ method. The CA IX ECD-HuIgG2 fusion protein was purified from harvested conditioned media via Protein A chromatography. The full-length protein was also expressed in B300.19 cells to generate B300.19/CA IX.

EXAMPLE 2

Anti-CA IX Antibodies

A. Antibody Generation

1. Immunization and Selection of Animals for Harvesting by ELISA

Monoclonal antibodies against CA IX were developed by sequentially immunizing XM3B-3 and XMG2 mice with recombinant CA IX antigen. In particular, each mouse was immunized into its' hind footpad with CA IX recombinant antigen, generating a large number of candidate mAbs. These antibodies were then screened for binding and anti-CA IX activity. The mice were initially boosted, and again boosted 3-4 days later with HT-29 cells expressing CA IX at a concentration of $10^7$ cells/mouse. Each mouse was further immunized into each hind footpad six additional times (at 3-4 day intervals) with soluble antigen, specifically 10 μg of CA-IX-IgG2-Fc. Four days after the final boost, sera from the immunized mice were tested by ELISA for titer against purified CA IX antigen bound to microtiter plates.

In some experiments determination of anti-CA IX titer was performed with biotinylated CA IX coated onto plates. 15-500 μg of CA IX protein was diluted in 1 mL of PBS at a pH of 8.6. 10 μl of 10 mg/mL sulfo-NHS-biotin (Biotin stock in DMSO) was added to the 1 mL CA IX-HIS protein solution for an incubation period of 1 hour at roomtemperature with rotation. After the 1 hour incubation, the reaction was quenched with 100 μl of saturated Tris and subjected to centrifugation and a minimum of 4 washes to separate free biotin from the biotinylated CA IX-His. The biotinylated CA IX-His (1 μg/mL) was coated onto Sigma Streptavidin plates for 1 hour at room temperature. A control Streptavidin plate was left uncoated for use as a control. The plates were washed five times with distilled water. Sera from the immunized animals were titrated in 2% Milk/PBS at 1:2 dilutions in duplicate from a 1:100 initial dilution. The last well was left blank as a control. The Streptavidin plates were washed five times with distilled water. A goat anti-human IgG Fc-specific HRP-conjugated antibody was added at a final concentration of 1 μg/mL for 1 hour at room temperature. Following five washes with distilled water, the Streptavidin plates were developed with the addition of TMB for 30 minutes and the ELISA was stopped by the addition of 1 M phosphoric acid. The specific titer for CA IX of the sera from the immunized mice was determined from the optical density at 450 nm.

TABLE 1

Anti-CA IX titre of CA IX-IgG Fc immunized XenoMouse animals

| Fremont Mouse I.D.s | Titer 1 sigma SA plate coated at 1 μg/ml B-MN-His | Titer 2 Sigma SA plate control (not coated) | Titer 3 B-Mn.His on sigma SA plate at 1 μg/ml | Titer 4 B-Mn.His on sigma SA plate at 1 μg/ml | Titer 5 sigma SA plate control (not coated) |
|---|---|---|---|---|---|
| L991-1 | >1:6400 | 1:12800 | >1:204800 | >1:102400 | 1:1600 |
| L991-2 | >1:6400 | 1:12800 | >1:204800 | >1:102400 | 1:1600 |
| L991-3 | >1:6400 | 1:6400 | >1:204800 | >1:102400 | 1:1600 |

TABLE 1-continued

Anti-CA IX titre of CA IX-IgG Fc immunized XenoMouse animals

| Fremont Mouse I.D.s | Titer 1 sigma SA plate coated at 1 μg/ml B-MN-His | Titer 2 Sigma SA plate control (not coated) | Titer 3 B-Mn.His on sigma SA plate at 1 μg/ml | Titer 4 B-Mn.His on sigma SA plate at 1 μg/ml | Titer 5 sigma SA plate control (not coated) |
|---|---|---|---|---|---|
| L991-4 | >1:6400 | 1:25600 | >1:204800 | >1:102400 | 1:3200 |
| L991-5 | >1:6400 | 1:12800 | 1:102400 | >1:102400 | 1:800 |
| naive | 1:6400 | 1:12800 | 1:12800 | 1:3200 | 1:1600 |

2. Harvest of Lymphocytes from Immunized Animals

XenoMouse animals (L991-3 and L991-4) were selected for harvest of plasma cells, based on the anti-CA IX titer data described above. A total of 55 plates were initiated using CD19$^+$ B lymphocytes. These plates were set up from the pooled inguinal, popliteal and para-aortic lymph nodes (50 plates) and splenic B lymphocytes (5 plates). The lymph node cells were cultured at either 500 CD19$^+$ cells/well (30 plates) or 250 CD19$^+$ cells/well (20 plates) and the splenic B lymphocytes were cultured at 500 cells/well. B cell cultures were also set up from uncut peripheral blood mononuclear cells at 2500 cells/well (5 plates).

3. Generation of Antibody-Producing Hybridomas

B cells isolated form pooled inguinal, popliteal and para-aortic lymph nodes and splenic B lymphocytes were used for hybridoma generation. Lymphocytes enriched for B cells were fused by electrocell fusion with P3-X63-Ag8.653 myeloma cells and were subjected to hypoxanthine/azaserine (HA) (Sigma, catalog #A9666) selection. Specifically, the fusion was performed by mixing washed enriched B cells and non-secretory myeloma P3X63Ag8.653 cells purchased from ATCC Catalog #CRL1580 (Kearney et al., *J. Immunol.*, 123:1548-1550 (1979) at a ratio of 1:1. The cell mixture was subjected to centrifugation at 800 g. After complete removal of the supernatant, the cells were treated with 2-4 ml of Pronase solution (CalBiochem, catalog #53702; 0.5 mg/ml in PBS) for less than 2 minutes. 3-5 ml of FBS was added to stop the enzyme activity and the suspension was adjusted to 40 ml total volume using electro cell fusion solution (ECFS) (0.3M Sucrose, Sigma, Catalog #S7903, 0.1 mM Magnesium Acetate, Sigma, Catalog #M2545, 0.1 mM Calcium Acetate, Sigma, Catalog #C4705). The supernatant was removed after centrifugation and the cells were resuspended in 40 ml ECFS. The cells were washed in ECFS once more and finally resuspended in ECFS to a concentration of 2×10$^6$ cells/ml. Electro-cell fusion was performed using a fusion generator, model ECM2001, Genetronic, Inc., San Diego, Calif. The fusion chamber size used was 2.0 ml using the following instrument settings:

Alignment condition: voltage: 50 v, time: 50 seconds;

Membrane breaking at: voltage: 3000 v, time: 30 ms; and

Post-fusion holding time: 3 seconds.

The hyridoma culture supernatants were screened by ELISA with a his-V5 tagged version of the CA IX protein. The results from the ELISA screen are presented in Table 6.

4. XenoMax Generation of Antibodies

Alternatively, after immunization and selection of B cells for use in antibody generation, wells with cultured B cells were subjected to a number of screens to determine specificity for CA IX antigen.

(a) ELISA

As mentioned above, cultured B cells were subjected to ELISA with a his-V5 tagged version of the CA IX protein.

Biotinylated CA IX-His was bound to streptavidin plates at 275 ng/ml and incubated for 18 hours at 4° C. The plate was washed five times with distilled water, blocked with 250 μl of 2% Milk/PBS for 30 minutes at room temperature, washed five times with distilled water, incubated with 40 μl of 2% Milk/PBS and 10 μl of B cell supernatant for 1 hour at room temperature, washed again five times with distilled water, incubated with 50 μl of Gt anti-Human (Fc)-HRP at 1 μg/ml for 1 hour at room temperature, washed five times with distilled water, incubated with 50 μl of TMB substrate, and to stop the reaction, incubated with 10 μL of 1M phosphoric acid in each well. The plate was read at a wavelength of 450 nm.

The first 30 plates (derived from the lymph node B-lymphocytes at 500 cells/well) were screened as described above on CA IX-His protein to identify the antigen-specific wells. The data in Table 2 showed that most of the wells had antigen-specific reactivity (2202/2880 at OD 0.3 or greater −78%). This indicated that these wells were quite polyclonal and likely would not be useful for subsequent screens. The Lymph Node B lymphocytes seeded at 250 cells/well and the B-lymphocytes derived from peripheral blood and the spleen (Table 3) were also analyzed. These data indicated that these wells were also likely polyclonal (412/1440 at OD 0.3 or greater −29%).

TABLE 4

Rescreen of one plate of the highest OD

| Tissue | Positives above cutoff OD of: | | | | | | | | | | | |
|---|---|---|---|---|---|---|---|---|---|---|---|---|
| | 0.1 | 0.2 | 0.3 | 0.4 | 0.5 | 0.6 | 0.7 | 0.8 | 0.9 | 1.0 | 1.5 | 2.0 |
| All wells | 95 | 75 | 64 | 60 | 57 | 51 | 46 | 41 | 35 | 30 | 14 | 8 |

(b) Native Binding Assay in Transiently Transfected CHO Cells

This assay for determining native binding to CA IX was conducted on CHO cells transiently expressing full length MN. BCC supernatants were qualitatively assessed and ranked for relative binding by eye. The BCC wells were binned (Table 5) using the combined ELISA, G250 and Native binding assays.

To determine native binding, CHO cells were transiently lipofected with full length MN. After 48 hours, the cells were trypsinized, seeded in Terasaki dishes (5000 cells/well), and cultured overnight at 37° C. The culture media was removed and cells were stained with 10 μL of B-cell culture supernatant for 2 hours on ice. The monoclonal anti-MN antibody 13.15 was included as a positive control; titrating 1:2 from 250 ng/mL. An irrelevant XG2 recombinant control was also included in the assay. After the primary antibody incubation, the media was removed and the cells were fixed with 1% Paraformaldehyde (10 μL for 20 min). The cells were washed twice with 20 μL PBS. The secondary

TABLE 2

30 Plates of Lymph Node B Lymphocytes Cultured at 500 cells/well

| Tissue | Positives above cutoff OD of: | | | | | | | | | | | | | |
|---|---|---|---|---|---|---|---|---|---|---|---|---|---|---|
| | 0.1 | 0.2 | 0.3 | 0.4 | 0.5 | 0.6 | 0.7 | 0.8 | 0.9 | 1.0 | 1.5 | 2.0 | 2.5 | 3 |
| Inguinal, Popliteal, Para-Aortic LN (plates 11-30) | 945 | 873 | 790 | 719 | 664 | 619 | 576 | 528 | 480 | 437 | 271 | 139 | 44 | 0 |
| above LN with "new EL4B5" (plates 1-10) | 1844 | 1589 | 1412 | 1265 | 1132 | 1031 | 947 | 861 | 768 | 670 | 358 | 148 | 32 | 0 |
| Total number positives: | 2789 | 2462 | 2202 | 1984 | 1796 | 1650 | 1523 | 1389 | 1248 | 1107 | 629 | 287 | 76 | 0 |

TABLE 3

10 plates of Lymph Node B-cells cultured at 250 cells/well and 5 plates from spleen and PBMNC

| Tissue | Positives above cutoff OD of: | | | | | | | | | | | |
|---|---|---|---|---|---|---|---|---|---|---|---|---|
| | 0.1 | 0.2 | 0.3 | 0.4 | 0.5 | 0.6 | 0.7 | 0.8 | 0.9 | 1.0 | 1.5 | 2.0 |
| Pooled Lymph Nodes * @ 250 cells/well (plates #31-50) | 957 | 405 | 210 | 146 | 108 | 79 | 56 | 40 | 34 | 30 | 11 | 4 |
| Spleen @ 500 cells/well (plates #51-55) | 475 | 222 | 102 | 33 | 20 | 12 | 11 | 8 | 8 | 7 | 3 | 2 |
| PBMNC @ 2500 cells/well (plates 56-60) | 480 | 235 | 100 | 42 | 16 | 11 | 7 | 6 | 6 | 6 | 2 | 1 |
| Total Number Positives: | 1912 | 862 | 412 | 221 | 144 | 102 | 74 | 54 | 48 | 43 | 16 | 7 |

Rescreening of one plate of the highest OD wells on CA IX-His (Table 4) showed that 67% of the wells repeated at the same OD cutoff. The percentage of positives generated in the initial screen (29%) and the percentage of repeat positives (67%) indicated that our cultures were set up very close to the theoretical limit of polyclonality based on the binomial distribution model (20%).

antibody (Goat anti-Human IgG Fc Alexa 488 2 μg/mL) was incubated on ice with the cells for 1 hour. The cells were washed twice with 2 μL PBS. The cells were viewed by fluorescent microscopy.

When antibodies were identified, the plasma cells were identified and isolated using a hemolytic plaque assay and PCR was performed to rescue the heavy and light chain sequences. The sequences were then cloned into standard antibody expression vectors, producing recombinant human antibodies. The antigen binding of the recombinant antibodies was subsequently confirmed

TABLE 5

Binning of the B Cell Culture wells based on the ability to bind CA-IX based on ELISA, MN G250 and Native Binding Assays

| Well | ELISA screens | | | MN G250 Competition | | Native Binding Terasaki | |
|---|---|---|---|---|---|---|---|
| | 1° Screen OD | 2° Screen OD | 3° Screen OD | SA control OD | G250 competition OD | IF Results IMN-CHO | Bins |
| MN1 Plate 45 C 9 | 0.87 | 0.87 | 2.03 | 0.10 | 0.31 | +5 | A |
| MN1 Plate 49 C 8 | 0.95 | 1.66 | 1.60 | 0.10 | 0.43 | +4 | A |
| MN1 Plate 41 E 1 | 0.55 | 0.55 | 1.51 | 0.09 | 0.49 | +3 | A |
| MN1 Plate 42 E 4 | 1.26 | 1.07 | 1.80 | 0.10 | 0.74 | +4 | A |
| MN1 Plate 41 F 5 | 0.81 | 1.05 | 1.65 | 0.15 | 1.56 | +4 | B |
| MN1 Plate 49 G 4 | 0.59 | 0.99 | 1.59 | 0.09 | 1.83 | +4 | B |
| MN1 Plate 47 H 10 | 0.73 | 0.67 | 1.58 | 0.10 | 2.19 | +4 | B |
| MN1 Plate 43 G 10 | 0.58 | 0.86 | 1.94 | 0.11 | 2.31 | +5 | B |
| MN1 Plate 41 D 1 | 0.58 | 0.50 | 1.39 | 0.10 | 2.53 | +5 | B |
| MN1 Plate 47 D 1 | 0.77 | 0.91 | 2.01 | 0.10 | 2.75 | +5 | B |
| MN1 Plate 44 D 10 | 0.78 | 0.87 | 1.75 | 0.08 | 2.91 | +5 | B |
| MN1 Plate 50 D 2 | 0.72 | 0.55 | 1.14 | 0.11 | 0.27 | +2 | C |
| MN1 Plate 48 G 5 | 0.85 | 0.72 | 1.54 | 0.09 | 0.30 | +1/+2 | C |
| MN1 Plate 48 E 2 | 1.28 | 0.58 | 1.85 | 0.09 | 0.45 | +1 | C |
| MN1 Plate 53 G 8 | 1.28 | 2.50 | 2.15 | 0.11 | 0.73 | | D |
| MN1 Plate 45 H 2 | 0.65 | 0.63 | 1.80 | 0.10 | 0.77 | | D |
| MN1 Plate 44 H 10 | 0.73 | 1.88 | 2.13 | 0.09 | 1.85 | +5 | |
| MN1 Plate 44 H 4 | 1.05 | 0.83 | 1.88 | 0.09 | 1.68 | +5 | |
| MN1 Plate 42 C 4 | 1.14 | 0.51 | 2.03 | 0.11 | 2.95 | +5 | |
| MN1 Plate 45 C 2 | 1.62 | 2.54 | 2.24 | 0.09 | 2.08 | +5 | |
| MN1 Plate 44 D 2 | 1.58 | 1.45 | 2.39 | 0.09 | 1.95 | +5 | |
| MN1 Plate 44 D 4 | 2.30 | 0.95 | 2.15 | 0.10 | 1.94 | +5 | |
| MN1 Plate 45 C 12 | 0.75 | 1.40 | 2.32 | 0.08 | 2.51 | +4 | |
| MN1 Plate 44 A 2 | 1.10 | 1.49 | 2.25 | 0.10 | 2.53 | +4 | |
| MN1 Plate 44 F 3 | 1.12 | 1.27 | 1.84 | 0.10 | 1.74 | +4 | |
| MN1 Plate 42 G 7 | 1.13 | 1.35 | 2.09 | 0.07 | 1.20 | +4 | |
| MN1 Plate 42 F 5 | 1.44 | 2.10 | 1.58 | 0.09 | 2.00 | +4 | |
| MN1 Plate 45 D 3 | 1.52 | 1.34 | 2.17 | 0.08 | 2.71 | +4 | |
| MN1 Plate 46 C 4 | 1.80 | 2.30 | 2.31 | 0.06 | 1.29 | +4 | |
| MN1 Plate 47 D 3 | 0.83 | 0.56 | 1.99 | 0.17 | 2.79 | +3/+4 | |
| MN1 Plate 46 H 6 | 0.87 | 1.25 | 2.00 | 0.10 | 1.94 | +3/+4 | |
| MN1 Plate 48 C 8 | 0.96 | 0.73 | 1.75 | 0.10 | 2.34 | +3/+4 | |
| MN1 Plate 49 B 2 | 0.63 | 0.79 | 1.44 | 0.09 | 2.34 | +3 | |
| MN1 Plate 47 G 10 | 0.66 | 0.89 | 1.74 | 0.10 | 2.13 | +3 | |
| MN1 Plate 49 C 10 | 0.71 | 1.73 | 1.87 | 0.08 | 2.57 | +3 | |
| MN1 Plate 44 E 3 | 0.72 | 0.97 | 1.43 | 0.07 | 2.28 | +3 | |
| MN1 Plate 47 F 8 | 0.74 | 0.58 | 1.32 | 0.08 | 2.35 | +3 | |
| MN1 Plate 47 A 2 | 0.76 | 1.24 | 2.08 | 0.10 | 1.20 | +3 | |
| MN1 Plate 41 B 12 | 0.77 | 0.81 | 2.07 | 0.07 | 2.50 | +3 | |
| MN1 Plate 43 H 7 | 1.02 | 0.97 | 1.98 | 0.09 | 2.50 | +3 | |
| MN1 Plate 46 F 8 | 1.40 | 1.20 | 1.98 | 0.10 | 2.63 | +3 | |
| MN1 Plate 46 E 2 | 2.03 | 2.05 | 2.23 | 0.10 | 1.72 | +2/+3 | |
| MN1 Plate 43 H 10 | 0.64 | 0.58 | 1.51 | 0.09 | 2.38 | +2 | |
| MN1 Plate 47 A 9 | 0.64 | 0.73 | 1.78 | 0.08 | 1.22 | +2 | |
| MN1 Plate 44 A 5 | 0.73 | 0.83 | 2.05 | 0.11 | 2.62 | +2 | |
| MN1 Plate 45 D 8 | 0.89 | 2.02 | 1.94 | 0.12 | 2.35 | +2 | |
| MN1 Plate 50 B 4 | 1.01 | 1.08 | 1.41 | 0.11 | 1.52 | +2 | |
| MN1 Plate 48 B 6 | 1.07 | 1.72 | 2.05 | 0.10 | 2.17 | +2 | |
| MN1 Plate 41 G 8 | 1.12 | 1.33 | 1.50 | 0.11 | 1.12 | +2 | |
| MN1 Plate 41 H 5 | 1.15 | 0.70 | 1.83 | 0.11 | 1.84 | +2 | |
| MN1 Plate 41 F 9 | 1.90 | 1.75 | 2.02 | 0.10 | 2.15 | +2 | |
| MN1 Plate 43 C 2 | 0.92 | 1.02 | 1.91 | 0.09 | 2.50 | +1 | |
| MN1 Plate 50 B 3 | 1.35 | 1.75 | 1.72 | 0.09 | 1.76 | +1 | |
| MN1 Plate 45 F 6 | 3.23 | 2.20 | 0.98 | 0.25 | 1.72 | +1 | |
| MN1 Plate 46 B 1 | 1.98 | 1.30 | 0.35 | 0.13 | 0.50 | +0.5 | |
| MN1 Plate 50 D 5 | 1.72 | 1.20 | 2.04 | 0.09 | 2.82 | no sample | |
| MN1 Plate 47 G 6 | 2.79 | 2.92 | 0.27 | 0.41 | 0.26 | | |

TABLE 5-continued

Bins
A: G250 competers, good native binders
B: good native binders, low OD (<0.1)
C: G250 competers, poor native binders
D: no sample, interesting?

B. Antibody Characterization

Antibodies identified from the XenoMax technology and hybridomas were further characterized by assessing their ability to mediate ADCC, internalize cell surface CA IX and inhibit the enzymatic activity of carbonix anyhydrase. Results from these characterizations are summarized in Table 6.

1. Sequence Alignment

The variable regions of the light chains and heavy chains of the antibodies generated from the XenoMax technology and hybridomas were analyzed for amino acid sequence similarity with germline Vgamma/D/J heavy chain and Vkappa/J light chain sequences. Identity and deletions of the Vgamma and Vkappa sequences, without their signal sequences, with their respective germline sequences are shown by a "–" and a "#", respectively in the figures. Dendrograms representing the similarity with the germlines sequences were also generated.

The sequence alignments of the amino acid sequence of the variable heavy chain regions of anti-CA IX antibodies, AB-MN-21.17.1 (SEQ ID NO: 2), AB-MN-22.19 (SEQ ID NO: 3), AB-MN-22.29 (SEQ ID NO: 4), AB-MN-22.3 (SEQ ID NO: 5), AB-MN-22.5 (SEQ ID NO: 6) with Vgamma/D/J germline sequence of VH4-4 (SEQ ID NO: 1), AB-MN-21.2.1 (SEQ ID NO: 8), AB-MN-21.5.2 (SEQ ID NO: 9), AB-MN-21.6.1 (SEQ ID NO: 10), AB-MN-21.7.1 (SEQ ID NO: 11), AB-MN-21.9.1 (SEQ ID NO: 12), AB-MN-22.11 (SEQ ID NO: 13), AB-MN-22.15 (SEQ ID NO: 14), AB-MN-22.16 (SEQ ID NO: 15), AB-MN-22.18 (SEQ ID NO: 16), AB-MN-22.21 (SEQ ID NO: 17), AB-MN-22.23 (SEQ ID NO: 18), AB-MN-22.9 (SEQ ID NO: 19) with Vgamma/D/J germline sequence of VH4-31 (SEQ ID NO: 7), AB-MN-21.10.1 (SEQ ID NO: 21) and AB-MN-22.25 (SEQ ID NO: 22) with Vgamma/D/J germline sequence of VH4-39 (SEQ ID NO: 20) and AB-MN-21.1.1 (SEQ ID NO: 24), AB-MN-21.14.1 (SEQ ID NO: 25), AB-MN-22.12 (SEQ ID NO: 26), AB-MN-22.17 (SEQ ID NO: 27), AB-MN-22.26 (SEQ ID NO: 28), AB-MN-22.27 (SEQ ID NO: 29), AB-MN-22.8.1 (SEQ ID NO: 30) with Vgamma/D/J germline sequence of VH4-59 (SEQ ID NO: 23) are shown in FIGS. 1, 3, 5 and 6, respectively. Dendrograms of alignments of the variable heavy chain regions of anti-CA IX antibodies with Vgamma/D/J germline sequence of VH4-4, VH4-31 and VH4-59 are shown in FIGS. 2, 4 and 7, respectively. FIGS. 1 and 2 show alignment and dendrogram, respectively, of the variable heavy chain region of anti-CA IX antibodies, AB-MN-21.17.1, AB-MN-22.19, AB-MN-22.29, AB-MN-22.3 and AB-MN-22.5 with VH4-4. FIGS. 3 and 4 show alignment and dendrogram, respectively, of the variable heavy chain regions of anti-CA IX antibodies, AB-MN-21.2.1, AB-MN-21.5.2, AB-MN-21.6.1, AB-MN-21.7.1, AB-MN-21.9.1, AB-MN-22.11, AB-MN-22.15, AB-MN-22.16, AB-MN-22.18, AB-MN-22.21, AB-MN-22.23 and AB-MN-22.9 with VH4-31. FIG. 5 shows alignment of the variable heavy chain regions of anti-CA IX antibodies, AB-MN-21.10.1 and AB-MN-22.25 with VH4-39. FIGS. 6 and 7 show alignment and dendrogram, respectively, of the variable heavy chain regions of anti-CA IX antibodies of AB-MN-21.1.1, AB-MN-21.14.1, AB-MN-22.12, AB-MN-22.17, AB-MN-22.26, AB-MN-22.27 and AB-MN-22.8.1 with VH4-59.

The sequence alignments of the amino acid sequence of the variable heavy chain regions of anti-CA IX antibodies, AB-MN-XG1-080 (SEQ ID NO: 71), AB-MN-XG1-141 (SEQ ID NO: 72) and AB-MN-XG1-174 (SEQ ID NO: 73) with germline sequence of Vgamma/D/J germline sequence of VH4-59/D3-3/JH6b (SEQ ID NO: 70), AB-MN-XG1-023 (SEQ ID NO: 75) with germline sequence of Vgamma/D/J germline sequence of VH4-30.1/D3-9/JH5b (SEQ ID NO: 74), AB-MN-XG1-051 (SEQ ID NO: 77) with VH3-21/D5-18/JH4b (SEQ ID NO: 77) and AB-MN-XG1-109 (SEQ ID NO: 79) with VH4-04/D1-20/JH6b (SEQ ID NO: 79) are shown in FIG. 18.

Figure 11:
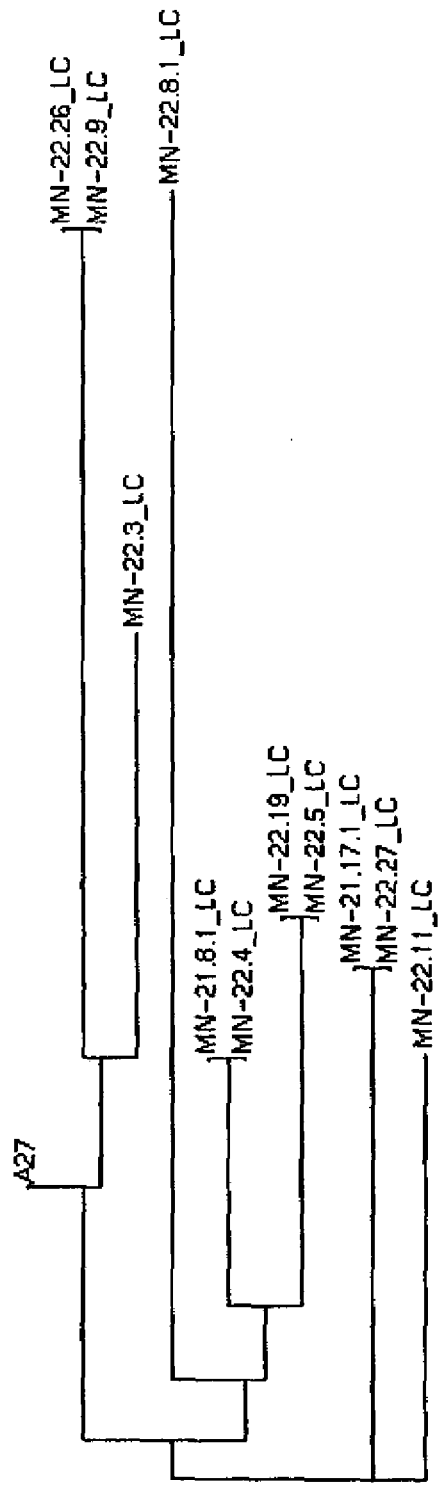
FIG. 11 shows a dendrogram representing the hierarchy of the anti-CA IX immunoglobulins, AB-MN-22.8.1_LC, AB-MN-21.17.1_LC, AB-MN-21.8.1_LC, AB-MN-22.11_LC, AB-MN-22.19_LC, AB-MN-22.26_LC, AB-MN-22.27_LC, AB-MN-22.3_LC, AB-MN-22.4_LC, AB-MN-22.5_LC and AB-MN-22.9_LC based on their similarity with the variable light chain region of VK-A27.
Figure 13:
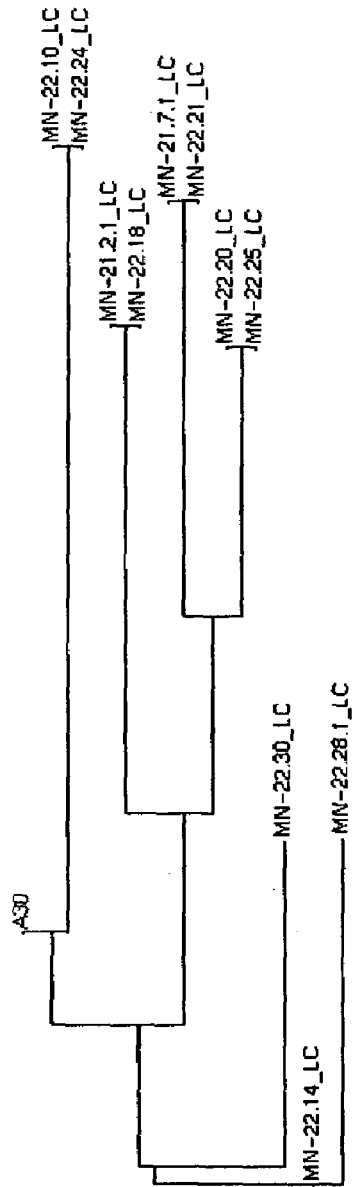
FIG. 13 shows a dendrogram representing the hierarchy of the anti-CA IX immunoglobulins, AB-MN-21.2.1_LC, AB-MN-21.7.1_LC, AB-MN-22.10_LC, AB-MN-22.14_LC, AB-MN-22.18_LC, AB-MN-22.20_LC, AB-MN-22.21_LC, AB-MN-22.24_LC, AB-MN-22.25_LC, AB-MN-22.28.1_LC and AB-MN-22.30_LC based on their similarity with the variable light chain region of VK-A30.
Figure 17:
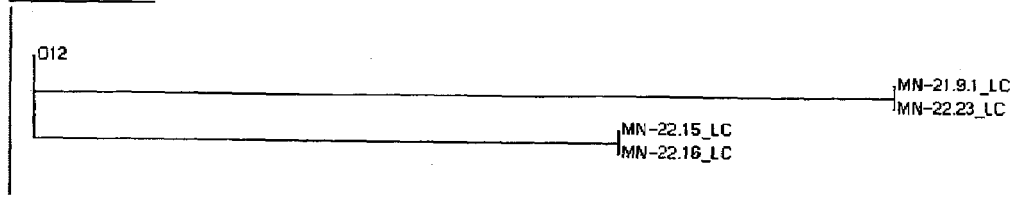
FIG. 17 shows a dendrogram representing the hierarchy of the anti-CA IX immunoglobulins, AB-MN-21.9.1_LC, AB-MN-22.15_LC, AB-MN-22.16_LC and AB-NM-22.23_LC based on their similarity with the variable light chain region of VK-O12.

The sequence alignments of the amino acid sequence of the variable light chain regions of anti-CA IX antibodies AB-MN-21.5.2 (SEQ ID NO: 32), AB-MN-21.6.1 (SEQ ID NO: 33), AB-MN-22.7 (SEQ ID NO: 34) with the amino acid sequence of Vkappa/J germline sequence of VK-A19 (SEQ ID NO: 31), AB-MN-22.8.1 (SEQ ID NO: 36), AB-MN-21.17.1 (SEQ ID NO: 37), AB-MN-21.8.1 (SEQ ID NO: 38), AB-MN-22.11 (SEQ ID NO: 39), AB-MN-22.19 (SEQ ID NO: 40), AB-MN-22.26 (SEQ ID NO: 41), AB-MN-22.27 (SEQ ID NO: 42), AB-MN-22.3 (SEQ ID NO: 43), AB-MN-22.4 (SEQ ID NO: 44), AB-MN-22.5 (SEQ ID NO: 45), AB-MN-22.9 (SEQ ID NO: 46) with the amino acid sequence of Vkappa/J germline sequence VK-A27 (SEQ ID NO: 35), AB-MN-21.2.1 (SEQ ID NO: 48), AB-MN-21.7.1 (SEQ ID NO: 49), AB-MN-22.10 (SEQ ID NO: 50), AB-MN-22.14 (SEQ ID NO: 51), AB-MN-22.18 (SEQ ID NO: 52), AB-MN-22.20 (SEQ ID NO: 53), AB-MN-22.21 (SEQ ID NO: 54), AB-MN-22.24 (SEQ ID NO: 55), AB-MN-22.25 (SEQ ID NO: 56), AB-MN-22.28.1 (SEQ ID NO: 57), AB-MN-22.30 (SEQ ID NO: 58) with the amino acid sequence of Vkappa/J germline sequence of VK-A30 (SEQ ID NO: 47), AB-MN-21.1.1 (SEQ ID NO: 60), AB-MN-21.14.1 (SEQ ID NO: 61), AB-MN-22.12 (SEQ ID NO: 62), AB-MN-22.17 (SEQ ID NO: 63), AB-MN-22.29 (SEQ ID NO: 64) with the amino acid sequence of Vkappa/J germline sequence of VK-L5 (SEQ ID NON: 59) and AB-MN-21.9.1 (SEQ ID NO: 66), AB-MN-22.15 (SEQ ID NO: 67), AB-MN-22.16 (SEQ ID NO: 68), AB-MN-22.23 (SEQ ID NO: 69) with the amino acid sequence of Vkappa/J germline sequence of VK-O12 (SEQ ID NO: 65) are shown in FIGS. 8, 10, 12, 14 and 16, respectively. Dendrograms of alignments of the variable light chain regions of anti-CA IX antibodies with anti-CA IX antibodies with Vkappa/J germline sequence of VK-A19, VK-A27, VK-A30, VK-L5 and VK-O12 are shown in FIGS. 9, 11, 13, 15 and 17, respectively. FIGS. 8 and 9 show alignment and dendrogram, respectively, of the light chain variable domain of anti-CA IX antibodies of 21.5.2, 21.6.1 and 22.7 with VK-A19. FIGS. 10 and 11 show alignment and dendrogram, respectively, of the light chain variable domain of anti-CA IX antibodies of AB-MN-22.8.1, AB-MN-21.17.1, AB-MN-21.8.1, AB-MN-22.11, AB-MN-22.19, AB-MN-22.26, AB-MN-22.27, AB-MN-22.3, AB-MN-22.4, AB-MN-22.5 and AB-MN-22.9 with VK-A27. FIGS. 12 and 13 show alignment and dendrogram, respectively, of the light chain variable domain of anti-CA IX antibodies of AB-MN-21.2.1, AB-MN-21.7.1, AB-MN-22.10, AB-MN-22.14, AB-MN-22.18, AB-MN-22.20, AB-MN-22.21, AB-MN-22.24, AB-MN-22.25, AB-MN-22.28.1 and AB-MN-22.30 with VK-A30. FIGS. 14 and 15 show alignment and dendrogram, respectively, of the light chain variable domain of anti-CA IX antibodies of AB-MN-21.1.1, AB-MN-21.14.1, AB-MN-22.12, AB-MN-22.17, and AB-MN-22.29 with VK-L5. FIGS. 16 and 17 show alignment and dendrogram, respectively, of the light chain variable domain of anti-CA IX antibodies of AB-MN-21.9.1, AB-MN-22.15, AB-MN-22.16 and AB-MN-22.23 with VK-O12.

The sequence alignments of the amino acid sequence of the light chain variable domain of anti-CA IX antibodies, AB-MN-XG1-080 (SEQ ID NO: 81), AB-MN-XG1-141 (SEQ ID NO: 82) and AB-MN-XG1-174 (SEQ ID NO: 83) with Vkappa/J germline sequence of A27/JK4 (SEQ ID NO: 80), AB-MN-XG1-023 (SEQ ID NO: 85) with L19/JK1 (SEQ ID NO: 84), AB-MN-XG1-051 (SEQ ID NO: 88) with A20/JK1 (SEQ ID NO: 87) and AB-MN-XG1-109 (SEQ ID NO: 89) with 02/JK3 (SEQ ID NO: 88) are shown in FIG. 19.

FIGS. 26A-26B show sequence alignments of the amino acid sequences of the variable regions of the heavy chains of CA IX antibodies with the amino acid sequences of the following Vgamma/D/J germline sequences: VHD1-2/D7-27/JH6b (SEQ ID NO: 124), VH4-4/D3-3/JH6b (SEQ ID NO: 126), VH4-61/D3-10/JH4b (SEQ ID NO: 127), VH3-23/D1-26/JH4b (SEQ ID NO: 129), VH4-31/D4-17/JH4b (SEQ ID NO: 131), VH3-30/D3-10/JH4b (SEQ ID NO: 132), VH-4-4/D6-19/JH6b (SEQ ID NO: 134), VH6-1/D1-26/JH4b (SEQ ID NO: 135), VH4-31/D3-10/JH4b (SEQ ID NO: 138), VH4-31/D4-11/JH4b NO: 139), VH4-31/D2-21/JH6b (SEQ ID NO: 140), VHI-2/D1-26/JH4b (SEQ ID NO: 141), VH4-59/D3-9/JH4b (SEQ ID NO: 143). The amino acid sequences of the heavy chain variable domain of CA IX antibodies, AX014H21__8__1N1G2 (SEQ ID NO: 124) was aligned with VH1-2/D7-27/JH6b. The amino acid sequences of the heavy chain variable domain of CA IX antibodies, AX014H22__5N1G2 (SEQ ID NO: 6), AX014H22__19N1G2 (SEQ ID NO: 3) and AX014H22__3N1G2 (SEQ ID NO: 5) were aligned with VH4-4/D3-3/JH6b. The amino acid sequences of the heavy chain variable domain of CA IX antibodies, AX014H22__14N1G2 (SEQ ID NO: 128) was aligned with VH4-61/D3-10/JH6b. The amino acid sequences of the heavy chain variable domain of CA IX antibodies, AX014H22__28__1N1G2 (SEQ ID NO: 130) was aligned with VH3-23/D1-26/JH6b. The amino acid sequences of the heavy chain variable domain of CA IX antibodies, AX014H22__23N1G2 (SEQ ID NO: 18) and AX014H22__9N1G2 (SEQ ID NO: 19) were aligned with VH4-31/D4-17/JH6b. The amino acid sequences of the heavy chain variable domain of CA IX antibodies, AX014H22__7N1G2 (SEQ ID NO: 133) was aligned with VH3-30/D3-10/JH6b. The amino acid sequences of the heavy chain variable domain of CA IX antibodies, AX014H21__17__1N1G2 (SEQ ID NO: 2) and AX014H22__29N1G2 (SEQ ID NO: 4) were aligned with VH4-4/D6-19/JH6b. The amino acid sequences of the heavy chain variable domain of CA IX antibodies, AX014H22__10N1G2 (SEQ ID NO: 136) and AX014H22__24N1G2 (SEQ ID NO: 137) were aligned with VH6-1/D1-26/JH6b. The amino acid sequences of the heavy chain variable domain of CA IX antibodies, AX014H21__52N1G2 (SEQ ID NO: 9) and AX014H21__6__1N1G2 (SEQ ID NO: 10) were aligned with VH4-31/D3-10/JH6b. The amino acid sequences of the heavy chain variable domain of CA IX antibodies, AX014H22__21N1G2 (SEQ ID NO: 17) was aligned with VH4-31/D4-11/JH6b. The amino acid sequences of the heavy chain variable domain of CA IX antibodies, AX014H22__16N1G2 (SEQ ID NO: 15) was aligned with VH4-31/D2-21/JH6b. The amino acid sequences of the heavy chain variable domain of CA IX antibodies, AX014H22__4N1G2 (SEQ ID NO: 142) was aligned with VH1-2/D1-26/JH6b. The amino acid sequences of the heavy chain variable domain of CA IX antibodies, AX014H21__1__1N1G2 (SEQ ID NO: 24), AX014H22__27N1G2 (SEQ ID NO: 29), AX014H21__14__1N1G2 (SEQ ID NO: 25), AX014H22__17N1G2 (SEQ ID NO: 27), AX014H22__26N1G2 (SEQ ID NO: 28) were aligned with VH4-59/D3-9/JH6b.

FIGS. 27A-27B show sequence alignments of the amino acid sequences of the variable regions of the heavy chains of CA IX antibodies with the amino acid sequences of the following Vgamma/D/J germline sequences: VH4-31/D5-24/JH2 (SEQ ID NO: 144), VH3-48/JH6b (SEQ ID NO: 145), VH4-31/D3-9/JH6b (SEQ ID NO: 147), VH4-39/JH4b (SEQ ID NO: 148), VH3-33/D3-10/JH6b (SEQ ID NO: 149), VH4-31/D3-10/JH6b (SEQ ID NO: 151), VH4-31/D3-9/JH3b (SEQ ID NO: 152), VH4-59/D6-13/JH6b (SEQ ID NO: 154). The amino acid sequences of the heavy chain variable domain of CA IX antibodies, AX014H22__11N1G2 (SEQ ID NO: 13) was aligned with VH4-31/D5-24/JH2. The amino acid sequences of the heavy chain variable domain of CA IX antibodies, AX014H22__13__1N1G2 (SEQ ID NO: 146) was aligned with VH3-48/JH6b. The amino acid sequences of the heavy chain variable domain of CA IX antibodies, AX014H22__15N1G2 (SEQ ID NO: 14) was aligned with VH4-31/D3-9/JH6b. The amino acid sequences of the heavy chain variable domain of CA IX antibodies, AX014H22__25N1G2 (SEQ ID NO: 22) and AX014H21__10__1N1G2 (SEQ ID NO: 21)_were aligned with VH4-39/JH4b. The amino acid sequences of the heavy chain variable domain of CA IX antibodies, AX014H22__30N1G2 (SEQ ID NO: 150) was aligned with VH4-33/D3-10/JH6b. The amino acid sequences of the heavy chain variable domain of CA IX antibodies, AX014H21__9__1N1G2 (SEQ ID NO: 12) was aligned with VH4-31/D3-10/JH4b. The amino acid sequences of the heavy chain variable domain of CA IX antibodies, AX014H22__18N1G2 (SEQ ID NO: 16), AX014H21__7__1N1G2 (SEQ ID NO: 11), AX014H22__20N1G2 (SEQ ID NO: 153) and and AX014H21__2__1N1G2 (SEQ ID NO: 8)_were aligned with VH4-31/D3-9/JH3b. The amino acid sequences of the heavy chain variable domain of CA IX antibodies, AX014H22__8__1N1G2 (SEQ ID NO: 30) and AX014H22__12N1G2 (SEQ ID NO: 26) were aligned with VH4-59/D6-13/JH3b.

FIGS. 28A-28B show sequence alignments of the amino acid sequences of the variable regions of the light chains of CA IX antibodies with the amino acid sequences of the following Vkappa/J germline sequences: O12/JK4 (SEQ ID NO: 155), A27/JK5 (SEQ ID NO: 156), A3/JK4 (SEQ ID NO: 157), A27/JK4 (SEQ ID NO: 80), A30/JK4 (SEQ ID NO: 158), L5/JK5 (SEQ ID NO: 159), A30/JK3 (SEQ ID NO: 160), A1/JK4 (SEQ ID NO: 161) and A27/JK2 (SEQ ID NO: 163). The amino acid sequences of the light chain variable domain of CA IX antibodies, AX014H22__15N1K (SEQ ID NO: 67), AX014H22__23N1K (SEQ ID NO: 69), AX014H21_9_1N1K (SEQ ID NO: 66), AX014H22_16N1K (SEQ ID NO: 68) were aligned with O12/JK4. The amino acid sequences of the light chain variable domain of CA IX antibodies, AX014H22_3N1K (SEQ ID NO: 43) were aligned with A27/JK5. The amino acid sequences of the light chain variable domain of CA IX antibodies, AX014H21_6_1N1K (SEQ ID NO: 33) and AX014H21_5_2N1K (SEQ ID NO: 32) were aligned with A3/JK4. The amino acid sequences of the light chain variable domain of CA IX antibodies, AX014H22_8_1N1K (SEQ ID NO: 36), AX014H22_27N1K (SEQ ID NO: 42), AX014H22_5N1K (SEQ ID NO: 45), AX014H21_17_1N1K (SEQ ID NO: 37), AX014H22_11N1K (SEQ ID NO: 39), AX014H21_8_1N1K (SEQ ID NO: 38), AX014H22_19N1K (SEQ ID NO: 40), AX014H22_4N1K (SEQ ID NO: 44) were aligned with A27/JK4. The amino acid sequences of the light chain variable domain of CA IX antibodies, AX014H22_30N1K (SEQ ID NO: 58), AX014H22_14N1K (SEQ ID NO: 51 and AX014H22_28_1N1K (SEQ ID NO: 57), were aligned with A27/JK4. The amino acid sequences of the light chain variable domain of CA IX antibodies, AX014H21_1_1N1K (SEQ ID NO: 60), AX014H22_29N1K (SEQ ID NO: 64), AX014H21_14_1N1K (SEQ ID NO: 61), AX014H22_17N1K (SEQ ID NO: 63) were aligned with L5/JK5. The amino acid sequences of the light chain variable domain of CA IX antibodies, AX014H22_24N1K (SEQ ID NO: 55) and AX014H22_10N1K (SEQ ID NO: 50) were aligned with A30/JK3. The amino acid sequence of the light chain variable domain of AX014H21_10_1N1K (SEQ ID NO: 162) was aligned with A1/JK4. The amino acid sequences of the light chain variable domain of CA IX antibodies, AX014H22_9N1K (SEQ ID NO: 46) and AX014H22_26N1K (SEQ ID NO: 41) were aligned with A27/JK2.

FIGS. 29A-29B show sequence alignments of the amino acid sequences of the variable regions of the light chains of CA IX antibodies with the amino acid sequences of the following Vkappa/J germline sequences: L5/JK3 (SEQ ID NO: 164), A3/JK2 (SEQ ID NO: 165), A30/JK1 (SEQ ID NO: 166) and A23/JK4 (SEQ ID NO: 167). The amino acid sequences of the light chain variable domain of CA IX antibodies, AX014H22_12N1K (SEQ ID NO: 62) was aligned with L5/JK3. The amino acid sequences of the light chain variable domain of CA IX antibodies, AX014H22_7N1K (SEQ ID NO: 34) was aligned with A3/JK2. The amino acid sequences of the light chain variable domain of CA IX antibodies, AX014H22_18N1K (SEQ ID NO: 52), AX014H21_7_1N1K (SEQ ID NO: 49), AX014H22_21N1K (SEQ ID NO: 54), AX014H22_20N1K (SEQ ID NO: 53), AX014H22_25N1K (SEQ ID NO: 56), AX014H21_2_1N1K (SEQ ID NO: 48) were aligned with A30/JK1. The amino acid sequence of the light chain variable domain of CA IX antibodiey, AX014H22_13_1N1K (SEQ ID NO: 168) was aligned with A23/JK4.

2. HT29 Tumor Cell Binding Assay

Binding of anti-CA IX antibodies to tumor cells was determined by immunofluorescence microscopy HT-29 cells were grown overnight in a Black Walled 96-well dish at 37° C. in McCoy's 5a media with 10% FCS. Staining of the cells was performed on ice. AB-hIL8-XG2142 was included as an irrelevant XG2 recombinant control. Mini lipofection supernatants were titrated 1:2 from neet in DMEM with 10% fetal calf serum (FCS). Primary antibody incubation of AB-MN-XG2-109, AB-MN-XG2-051, or AB-MN-XG2-023, was performed on ice for 1 hour, and cells were subsequently washed 2× with 100 μL PBS. The cells were incubated with a secondary antibody (Goat anti-Human IgG Fc Alexa) at concentration of 2 μg/mL for 1 hour on ice. Cells were further washed twice with 100 μL PBS. Cells were fixed with 1% Paraformaldehyde and viewed on Olympus Imaging Station.

Figure 20:
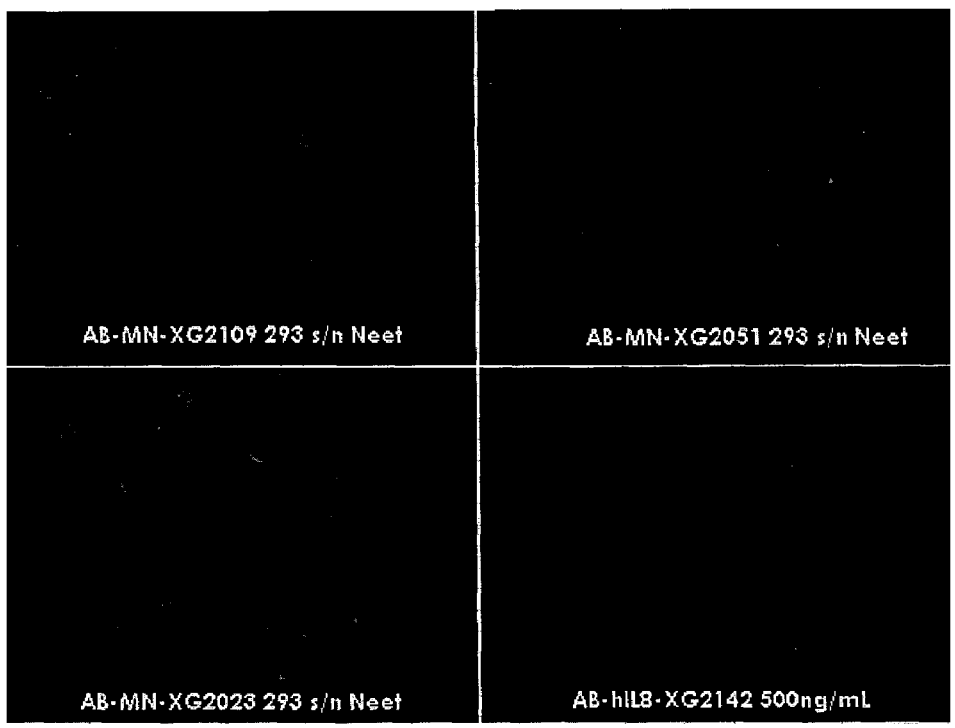
FIG. 20 represents immunofluorescence results showing that anti-CA IX antibodies, AB-MN-XG2-109, AB-MN-XG2-051 and AB-MN-XG2-023 bind to tumor cells while control antibodies against IL8, AB-hIL8-XG2142, do not bind to HT-29 tumor cells.

Results as shown in FIG. 20 show that AB-MN-XG2-109, AB-MN-XG2-023, and AB-MN-XG2-051 were able to bind to HT-29 tumor cells.

3. Proliferation Assay

Figure 21A:
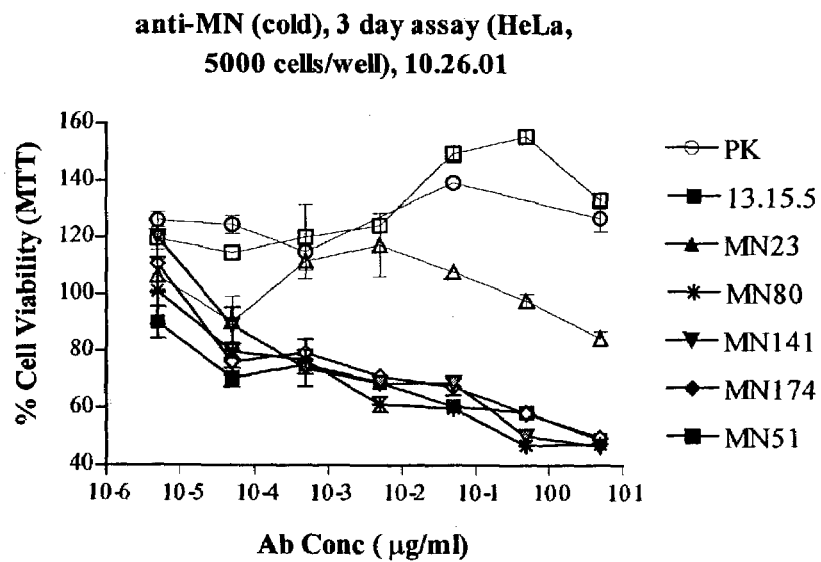
FIGS. 21A-C represent cell viability assay results showing that anti-CA IX antibodies, AB-MN-XG1-023 (MN23), AB-MN-XG1-080 (MN80), AB-MN-XG1-141 (MN141), AB-MN-XG1-174 (MN174) and AB-MN-XG1-051 (MN51) reduced the viability of HeLa and MDA 468 cells expressing endogenous CA IX antigen the affect of anti-CA IX antibodies on the viability of HeLa cell and MDA468 cells expressing endogenous CA IX.
Figure 21B:
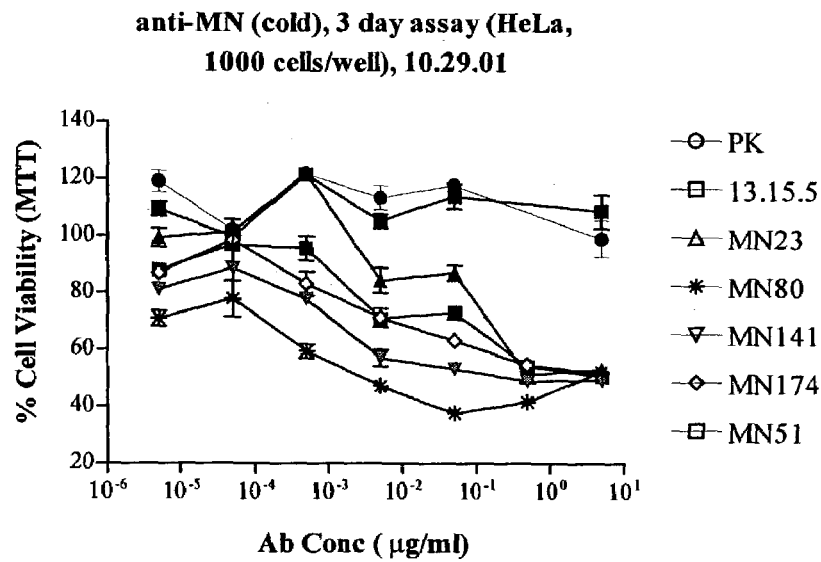

Anti-CA IX antibodies were tested for their ability to reduce the viability of HeLa cells and MDA 468 cells expressing endogenous CA IX antigen (FIGS. 21A and 21B). The cell viability assay directly measures mitochondrial function with decreased mitochondrial activity possibly leading to a decrease in cell viability under stressful conditions.

As described in the Promega's manufacturer's protocol, The CellTiter 96® AQueous One Solution Cell Proliferation Assay (a) was a colorimetric method for determining the number of viable cells in proliferation or cytotoxicity assays. The CellTiter 96® AQueous One Solution Reagent contained a novel tetra-zolium compound [3-(4,5-dimethylthiazol-2-yl)-5-(3-carboxymethoxyphenyl)-2-(4-sul-fopheny)-2H-tetrazolium, inner salt; MTS] and an electron coupling reagent (phenazine ethosulfate; PES). PES had enhanced chemical stability, which allowed it to be combined with MTS to form a stable solution. This convenient "One Solution" format was an improvement over the first version of the CellTiter 96® AQueous Assay, where phenazine methosulfate (PMS) was used as the electron coupling reagent, and PMS Solution and MTS Solution are supplied separately. The MTS tetrazolium compound (Owen's reagent) was bioreduced by cells into a colored formazan product that is soluble in tissue culture medium. This conversion was presumably accomplished by NADPH or NADH produced by dehydro-genase enzymes in metabolically active cells. Assays were performed by adding a small amount of the CellTiter 96® AQueous One Solution Reagent directly to culture wells, incubating for 1-4 hours and then recording absorbance at 490 nm with a 96 well plate reader.

Figure 21C:
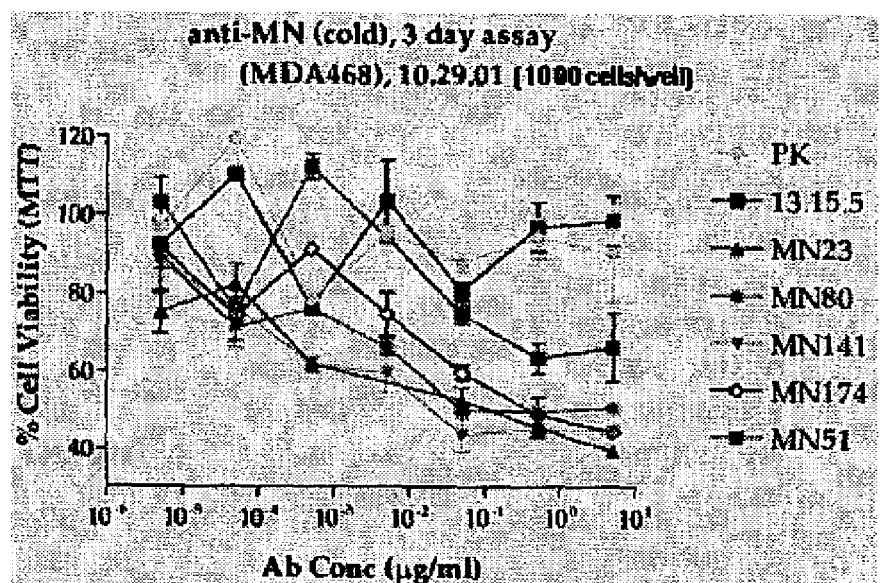

As shown in FIG. 21A, 21B and 21C, AB-MN-XG1-080, AB-MN-XG1-141, AB-MN-XG1-174, AB-MN-XG1-023, AB-MN-XG1-051 reduced the viability of HeLa cells and MDA 468 cells expressing endogenous CA IX antigen.

4. Internalization Assay

Figure 22:
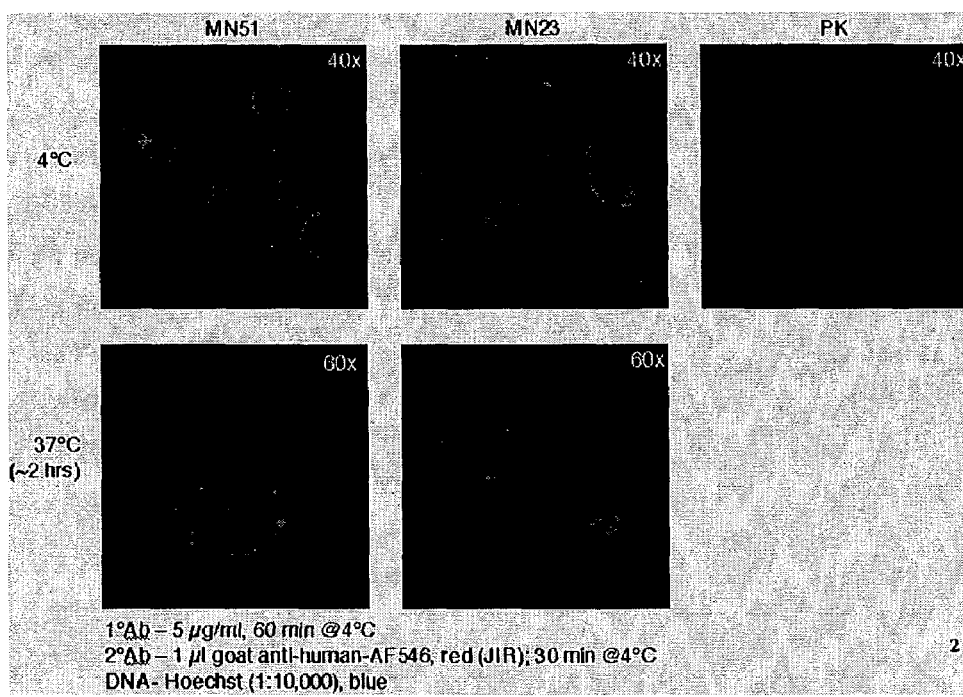
FIG. 22 represents immunofluorescences results showing that anti-CA IX antibodies, AB-MN-XG1-051 (MN51) and AB-MN-XG1-023 (MN23) were internalized into SKRC10 cells.

Anti-CA IX antibodies were further tested for their ability to become internalized by SKRC10 cells (FIG. 22). Internalization of the antibodies were detected by immunofluorescence microscopy.

SKRC10 cells were seeded at 2–5×10$^4$ cells/well in an 8-chamber slide for 24-48 hrs. Anti-CA IX primary antibody (5 μg/ml in 2% FBS/PBS) was added to each well and incubated for 1 hour at 4° C. (100 μl total volume). The wells were washed three times with cold PBS. Secondary antibody (1 μl goat anti-human AF546, Jackson) was added to the wells for 1 hour at 4° C. (100 μl total volume, 2% FBS/PBS). After three washes with cold PBS, internalization was initiated by shifting the chamber slides to 37° C. for specific time points (for cell surface staining, cells were left on ice). Internalization was stopped by shifting the cells from 37° C. to ice. Cells were fixed in formaldehyde (Cytofix, Pharmingen-should be ~3.7%) for a period of 10 min on ice. Cells were then washed 3 times with cold PBS. DNA was stained with Hoechst (1:10,000 in PBS) for 5 min on ice. The cells were washed three times with cold PBS. Chambers were detached excess buffer was aspirated from the slide. To view cells, 1 drop of mounting medium (Vectashield) was added to each chamber. Cells were viewed under 40×-60× magnification.

As shown in FIG. 22, AB-MN-XG1-051 and AB-MN-XG1-023 antibodies were internalized into SKRC10 cells.

5. Antibody-Dependent Cell-Mediated Cytotoxicity (ADCC) Assay

Peripheral blood mononuclear cells (PBMCs) purified from whole blood over Ficoll-paque were used as effector cells to mediate lysis of antibody sensitized SKRC-52 cells labeled with EuDTPA.

SKRC-52 renal cancer cell lines which express MN antigen were used as target cells and were incubated with various concentrations of anti-CA IX antibodies ranging from 0.0001 μg/mL to 10 μg/mL. The cells were cultured in McCoy's 5a medium supplemented with 2 mM glutamine, 100 units/mL penicillin, 100 μg/mL streptomycin and 10% fetal bovine serum. SKRC-52 cells were washed once with HEPES buffer (containing 50 mM Hepes, 93 mM NaCl, 5 mM KCl and 2 mM $MgCl_2$, pH 7.4). $10 \times 10^6$ target cells were suspended in 1.0 mL of cold labeling buffer containing 600 μM $EuCl_3$, 3 mM DTPA and 25 μg/mL dextran sulphate and incubated on ice for 20 minutes with frequent shaking. Labeling of target cells was terminated with the addition of 9 mL of repair buffer (Hepes buffer containing 2 mM $CaCl_2$ and 10 mM D-glucose at pH 7.4) followed by further incubation on ice for 5 minutes. Then the tube was filled up with repairing buffer and the cells are spun down. Labeled cells were washed three times more with repairing buffer and twice with assay medium (RPMI 1640 medium with 10% fetal bovine serum) and kept on ice until required. Immediately prior to the experiment, the cells were washed once more in assay medium and the cell pellet was transferred to a clean test tube, diluted to $10^5$ cells/mL.

Anti-CA LX monoclonal antibodies used in the assay were AB-MN-21.1.1, AB-MN-21.2.1, AB-MN-21.6.1, AB-MN-21.7.1, AB-MN-21.8.1, AB-MN-21.9.1, AB-MN-21.10.1, AB-MN-21.11.1, AB-MN-21.13.1, AB-MN-21.14.1, AB-MN-21.15.1, AB-MN-21.17.1, AB-MN-21.18.1, AB-MN-21.5.2 (IgG1) and AB-MN-22.1, AB-MN-22.22 (IgG2). Antibody controls and samples were diluted in 10 fold dilutions in assay medium and 50 μL volumes pipetted into U-bottomed microtiter plates. The assay blank consisted of medium only. The assay plates containing samples were pre-cooled on ice for 30 minutes. Target cells labeled with EuDTPA as described above were added in 50 μL volumes ($0.5 \times 10^4$ cells) and incubated on ice for 30 minutes. Effector cells, peripheral blood mononuclear cells (PBMC) isolated from the interface created upon centrifigation of fresh blood from normal donors on a Ficoll-Paque gradient (Amersham Pharmacia Biotech AB) with a density of 1.0770 g/ml were added in 100 μl volumes (E:T ratio of 50:1). The plates were shaken briefly on a plate shaker. ADCC mediated lysis of target cells was induced after pelleting cells by centrifugation at 1800 rpm for 5 minutes, followed by incubation at 37° C. in a humidified $CO_2$ incubator for 2 hours. The cells were centrifuged again and 20 μL supernatants collected for estimation of EuDTPA release to a flat-bottomed microtiter isoplate, to which was added 200 μL enhancement solution containing 15 μM 2-naphthoyl-trifluoroacetone, 50 μM tri-n-octylphosphine oxide and 0.1% (v/v) Triton X-100. EuDTPA and enhancement solution was mixed for 10 minutes on a shaker. Fluorescence was quantified using a wallac 1420 Multilabel Counter.

The lysis of target cells was determined in the presence of antibody (experimental release), without antibody (spontaneous release) or in 1% Triton X-100 (total release). Percent specific cell lysis was calculated using the equation:

$$\text{Percent specific lysis} = \frac{(\text{experimental release}) - (\text{spontaneous release})}{(\text{total release}) - (\text{spontaneous release})} \times 100$$

Figure 23A:
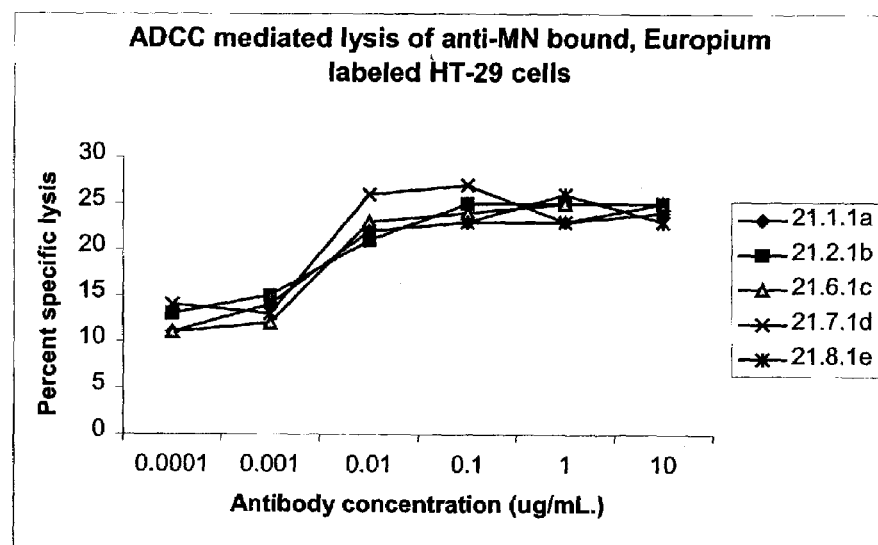
FIGS. 23A-C shows the induction of antibody-dependent cell-mediated cytotoxicity (ADCC) by anti-CA IX antibodies in HT-29 or SK-RC-52, cells from a renal cell carcinoma cell line, target cells.
Figure 23B:
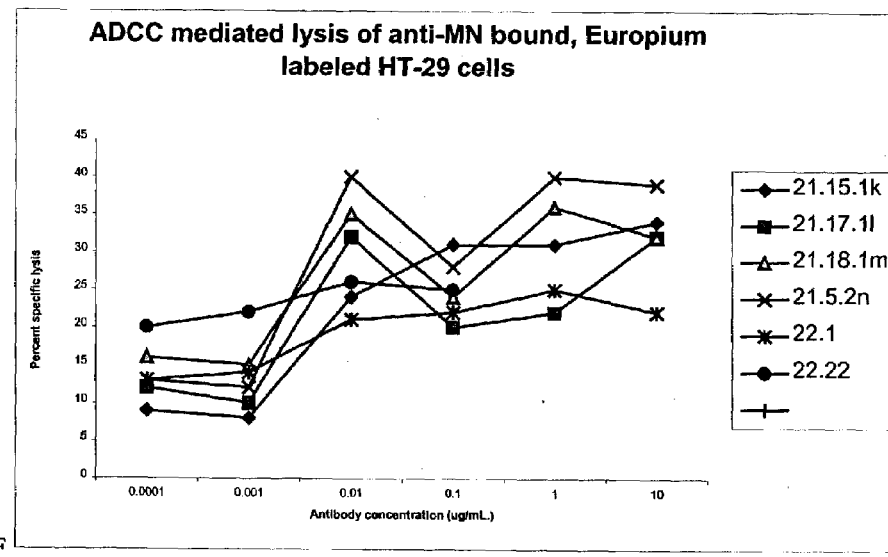
Figure 23C:
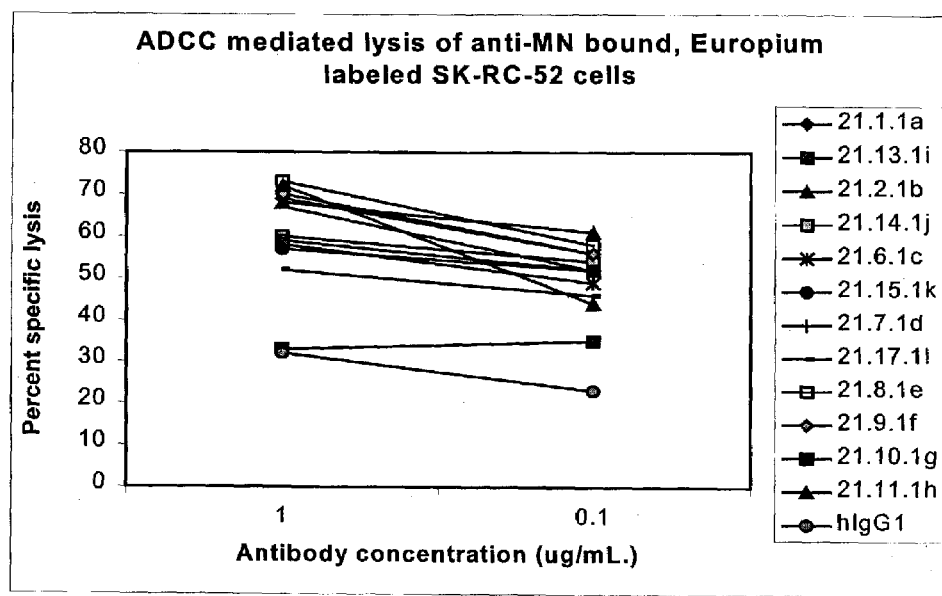

FIGS. 23A, 23B and 23C show that as low as 0.01 mg/mL anti-CA IX IgG1 antibodies induced a cellular cytotoxicity of about 25-40% compared to 15-20% lysis induced by IgG2 antibodies. Anti-CA IX IgG1 antibodies induced a cellular cytotoxicity of about 55-75% with 1 μg/mL and 45-60% with 0.1 μg/mL antibody concentration compared to 30% and 20% lysis induced by hIgG1 isotype control at 1 mg/mL and 0.1 mg/mL, respectively using SK-RC-52 target cells.

6. Carbonic Anhydrase Spectrophotometric Assay

To determine whether the anti-CA IX antibodies affect the enzymatic activity of CA IX, the antibodies were tested in a spectrophotometric assay. 50 μL of carbonic anhydrase or MN protein at 0.01 mg/mL was added to 2.4 ml of phenol red at 12.5 mg/L before mixing with the substrates of CA IX, $H_2O$ and $CO_2$. As a control, 2.4 ml of phenol red at 12.5 mg/L was mixed with 0.6 mL of water saturated with $CO_2$ in the absence of carbonic anhydrase or MN protein. Mixing was performed at the T-junction between two syringes, one containing phenol red/carbonic anhydrase and the other water/$CO_2$. The mixed solution was dispensed into a UV cuvette and the absorbance at 558 nm is recorded. This reaction was monitored at a temperature of about 15° C. Carbonic anhydrase activity was demonstrated by the difference in time for the complete hydration of $CO_2$ between the control by itself and the control with carbonic anhydrase or MN protein. The completion of the reaction was indicated by the solution changing from red to yellow. To test the effect of an antibody on carbonic anhydrase activity, antibody was incubated with the MN receptor at 2-8° C. for 4 hours before it was added to the substrate containing solution. The assay was carried out as described above.

All antibodies that bound CA IX were tested for their ability to inhibit enzyme activity. CA IX antibodies, AB-MN-21.7 and AB-MN-21.17.1, AB-MN-22.8, AB-MN-22.12, AB-MN-22.13, AB-MN-22.27 and AB-MN-22.28 tested positive for the ability to inhibit the carbonic anhydrase activity CA IX (Table 6).

7. Affinity Determination

Anti-CA-IX antibodies of the present invention were further tested for their affinity for CA IX antigen.

All CA IX antibodies of the present invention were diluted in running buffer with BSA and CM-Dextran (3 g/250 ml, respectively) according to their concentration using the following methods: dilution 1/70 with a concentration greater than 0.3 mg/ml; 1/300 dilution with a concentration greater than or equal to 0.3 mg/ml; 1/1500 with a concentration greater than or equal to 0.6 mg/ml; 1/3000 with a concentration greater than or equal to 3.0 mg/ml. Each monoclonal antibody was captured on a separate surface using 5-minute contact, and a 6-minute wash for stabilization of monoclonal antibody. Kinject CA IX antigen at 600 nM over all surfaces for one minute was followed by 2-minute dissociation. Two different antigens were used to determine affinity. One antigen comprised the entire extracellular domain and the other contained only the catalytic domain. At higher concentrations, the protein containing the catalytic domain resulted in cleaner data than the protein containing the entire extracellular domain. However, no DTT was added in the screening process of the affinity of the antibodies for CA IX since the addition of 10 mM DTT abolished binding of both proteins. Binding data was prepared by subtracting the baseline drift of a buffer kinject just prior to the injection of the antigen from the measurements taken after the injection of the antigen. Data were normalized for the amount of CA IX antibody captured on each surface, and were further fit globally to a 1:1 interaction model to determine binding kinetics. The data are summarized in Table 6.

The 96 different cancer cells were grown in respective medium, aliquoted into 96 well plates and incubated with 5 μg/ml of CA IX antibody, AB-MN-21.141 for 1 hour. The cells were washed 2 times and then incubated with the secondary antibody, goat anti-human IgG-HRP (Jackson Immunoresearch). After washing the secondary antibody, tetramethylbenzidine (TMB) substrate (Zymed) was added to each well. The OD was measured at 650 nm.

Figure 24A:
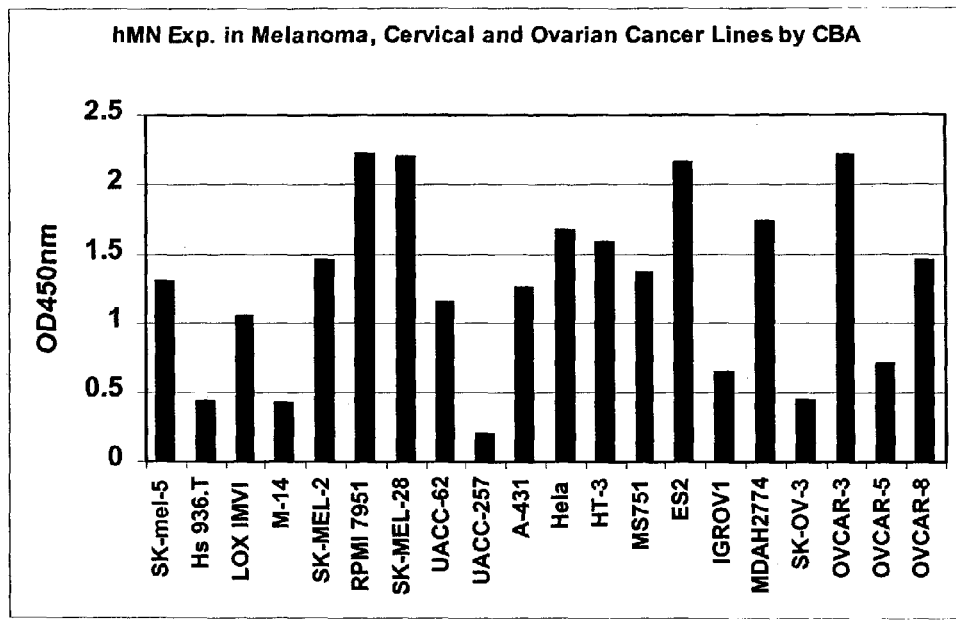
FIGS. 24A,B represent cell based array (CBA) results that show the level of CA IX expression in a number of tumor cell lines. Human CA IX expression in melanoma, cervical and ovarian cancer cell lines are shown in the upper panel while human CA IX expression in pancrease, prostate and renal cancer cell lines are shown in the lower panel of the figure.
Figure 24B:
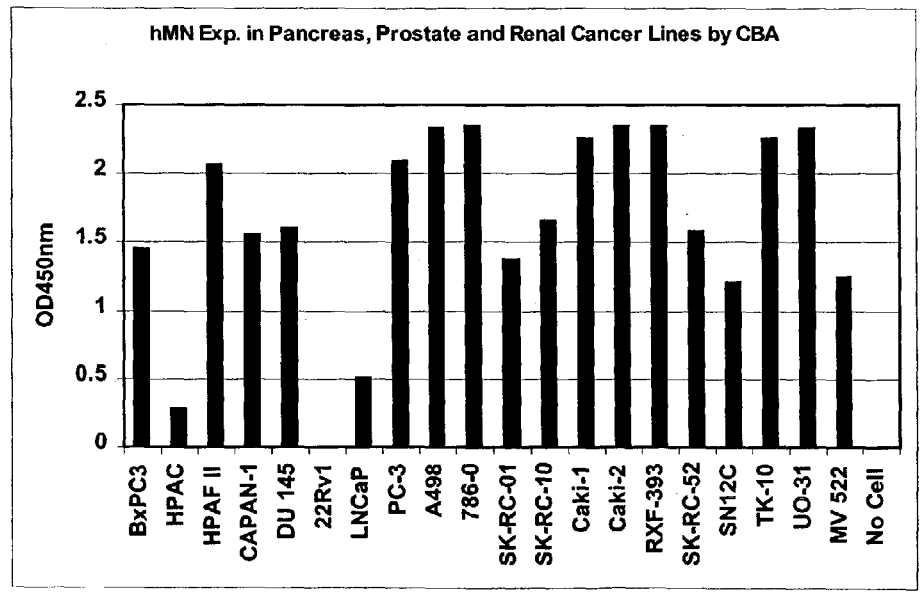

The graphs in FIGS. 24A and 24B represents the results of CA IX expression in a subset of the cancer cell lines tested

TABLE 6

Summary Table of Antibodies that have been Characterized

| Antibody Designation | IgG Isotype | CA-IX-His-ECD | CA9-CD Binding | Internalization | ADCC Activity | Inhibits CA9 Enzyme | Affinity ECD/CD |
|---|---|---|---|---|---|---|---|
| 21.1.1 a | IgG1 | 1.643 | 2.5 | Yes | Yes | No | 27.4/1.6 |
| 21.2.1 b | IgG1 | 1.209 | 2.485 | Yes | Yes | No | 36/3.2 |
| 21.6.1 c | IgG1 | 0.618 | 2.247 | Yes | Yes | No | 94.9/91 |
| 21.7.1 d | IgG1 | 1.928 | 2.772 | Yes | Yes | Yes | 29.9/1.1 |
| 21.8.1 e | IgG1 | 1.61 | 2.54 | Yes | Yes | No | 225/24 |
| 21.9.1 f | IgG1 | 1.62 | 2.533 | Yes | Yes | No | 417/.09 |
| 21.10.1 g | IgG1 | 0.059 | 0.187 |  | Yes | Yes | 13/NA |
| 21.11.1 h | IgG1 | 1.195 | 2.734 | Yes | Yes | No | 36.9/NA |
| 21.14.1 j | IgG1 | 1.78 | 2.473 | Yes | Yes | No | 18.3/3.0 |
| 21.15.1 k | IgG1 | 1.501 | 2.629 | Yes | Yes | No |  |
| 21.17.1 l | IgG1 | 1.853 | 2.663 | Yes | Yes | Yes | NA/3.7 |
| 21.18.1 m | IgG1 | 1.191 | 2.066 | Yes | Yes | No | 4.6/35 |
| 21.5.2 n | IgG1 | 0.893 | 2.427 | Yes | Yes | No | 120/NA |
| #141 | IgG1 | 2.562 | 2.561 | Yes |  | Yes | 6/.05 |
| #174 | IgG1 | 2.515 | 2.505 | Yes |  | No | NA/2.1 |
| #80 | IgG1 | 2.705 | 2.846 | Yes |  | No | 16.2/NA |
| #23 | IgG1 | 2.221 | 2.419 | Yes |  | No | NA/NA |
| #109 | IgG1 | 1.601 | 2.898 | Yes |  | No | 5.34/3.7 |
| #51 | IgG1 | 2.468 | 2.883 | Yes |  | No | 0.27.84 |
| 22.7 | IgG2 | 0.097 | 0.715 |  |  | No | NA/NA |
| 22.8 | IgG2 | 2.406 | 2.768 | Yes |  | Yes | 16.9/NA |
| 22.9 | IgG2 | 0.395 | 2.276 |  |  | No | NA/NA |
| 22.10 | IgG2 | 0.057 | 0.115 | Yes |  | No | NA/NA |
| 22.11 | IgG2 | 1.156 | 0.79 |  |  | No | NA/NA |
| 22.12 | IgG2 | 2.381 | 2.579 |  |  | Yes | 9.78/4.4 |
| 22.13 | IgG2 | 1.848 | 0.118 |  |  | Yes | 18.8/NA |
| 22.14 | IgG2 | 0.763 | 2.033 |  |  | No | NA/NA |
| 22.15 | IgG2 | 0.831 | 2.528 |  |  | No | 8.8/108 |
| 22.16 | IgG2 | 0.162 | 0.525 |  |  | No | NA/NA |
| 22.17 | IgG2 | 2.163 | 2.568 | Yes |  | No | NA/NA |
| 22.18 | IgG2 | 2.234 | 2.75 | Yes |  | No | 1.1/.05 |
| 22.19 | IgG2 | 2.123 | 3.012 | Yes |  | No | NA/NA |
| 22.20 | IgG2 | 1.72 | 2.707 |  |  | No | NA/NA |
| 22.21 | IgG2 | 2.176 | 2.736 |  |  | No | 0.74/0.1 |
| 22.22 | IgG2 | 2.445 | 2.537 | Yes |  | No | NA/NA |
| 22.23 | IgG2 | 2.008 | 2.692 |  |  | No | NA/NA |
| 22.24 | IgG2 | 0.085 | 0.07 |  |  | No | NA/NA |
| 22.25 | IgG2 | 1.841 | 2.475 |  |  | No | NA/NA |
| 22.26 | IgG2 | 1.991 | 2.747 |  |  | No | NA/NA |
| 22.27 | IgG2 | 1.224 | 1.84 |  |  | Yes | 162/NA |
| 22.28 | IgG2 | 0.404 | 2.537 |  |  | Yes | 2.75/NA |
| 22.29 | IgG2 | 1.957 | 2.52 |  |  | No | NA/NA |
| 22.30 | IgG2 | 2.201 | 2.464 |  |  | No | NA/NA |
| G250 |  |  |  |  |  | NO | NA/NA |

EXAMPLE 3

CA IX Expression

A. Expression of CA IX in Cancer Cells

To determine whether cancer cells express CA IX, 96 different cancer cells were incubated with anti-CA IX antibody and subsequently incubated with anti-human IgG-HRP in a cell based array (CBA).

in the CBA. Results showing expression levels of human CA IX in melanoma cell lines, SK-mel-5, Hs 936.T, LOX IMVI, M-14 SK-MEL-2, UACC-62 and UACC-257, cervical cancer cell lines, A-431, Hela, HT-3, MS751 and ES2 and and ovarian cancer cell lines, IGROV1, MDAH2774, SK-OV-3, OVCAR-4, OVCAR-5 and OVCAR-8 are shown in FIG. 24A. Results showing expression levels of human CA IX in pancreatic cancer cell lines, BxPC3, HPAC, HPAF II and CAPAN-1,, prostate cancer cell lines, DU 145, 22Rv1, LNCaP and PC-3 and renal cancer cell lines, A498, 786-0, SK-RC-01, SK-RC-10, Caki-1, Caki-2, RXF-393, SK-RC-52, SN12C, TK-10, UO-31, MV 522 are shown in FIG. 24B.

B. Induced Expression of CA IX In Hypoxic Conditions

To determine whether CA IX expression is induced when cells are grown under hypoxic conditions, ovarian (OvCar 3) and cervical (HeLa) cancer cells were cultured under aerobic (A) or hypoxic (H), 0.5% oxygen, conditions for 24 to 48 hours. The cells were harvested and the level of cell surface CA IX expression was determined in a cell based assay (CBA) using 5 µg/ml CA IX antibody, AB-MN-21.141, per well. After incubation with the CA IX antibody for 1 hour, the secondary goat anti-human IgG-HRP was added to the wells. The wells were washed 2 times and further incubated with tetramethylbenzidine (TMB) substate. The OD was measured at 650 nm.

Figure 25:
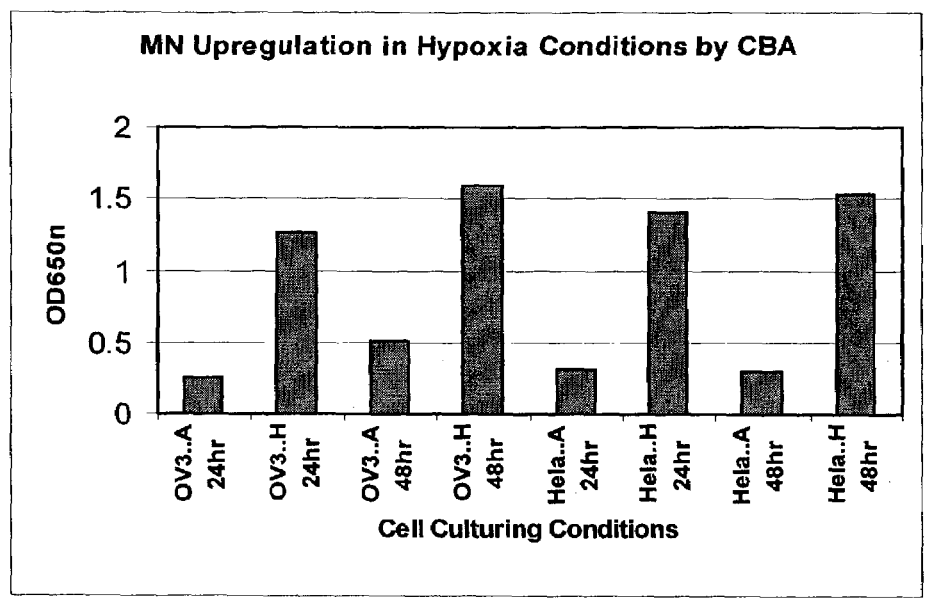
FIG. 25 represents cell based array (CBA) results that show upregulation of CA IX expression in cells cultured in hypoxic conditions.

FIG. 25 shows induction of CA IX expression in cells cultured in hypoxic conditions.

EXAMPLE 4

Uses of Anti-CA IX Antibodies for Tumor Treatment

Antibodies specific to tumor antigens such as anti-CA IX are useful in targeting of tumor cells expressing such antigens for elimination.

A. Linkage of Anti-CA IX Antibody to Ricin and Other Toxins

Ricin, a cellular toxin, is finding unique applications, especially in the fight against tumors and cancer. Implications are being discovered as to the use of ricin in the treatment of tumors. Ricin has been suggested to have a greater affinity for cancerous cells than normal cells (Montfort et al. 1987) and has been often termed as a "magic bullet" for targeting malignant tumors. Toxins such as ricin remain active even if the B chain which is responsible for because of toxin nonspecific lectin activity leads to toxic side effects is removed. Accordingly, if the solitary A chain is coupled to a tumor-specific antibody, the toxin has a specific affinity for cancerous cells over normal cells (Taylorson 1996). For example, ricin immunotoxin has been developed to target the CD5 T-cell antigen often found in T-cell and B-cell malignancies (Kreitman et al. 1998).

A novel method of coupling whole intact ricin to monoclonal antibody is described in Pietersz et al. (*Cancer Res* 48(16):4469-76 (1998)) and includes blocking of nonspecific binding of the ricin B-chain. Coupling of ricin to the anti-CA IX antibodies of the present invention may be done by using the bifunctional reagents S-acetylmercaptosuccinic anhydride for antibody and succinimidyl 3-(2-pyridyldithio) propionate for ricin. The coupling should result in the loss of B-chain binding activity, while impairing neither the toxic potential of the A-chain nor the activity of the antibody. Whole ricin-antibody conjugates produced in this way should not bind nonspecifically to target cells, the most important implication being that such immunotoxins should be more potent that ricin A-chain conjugates and capable of being used in vivo.

Immunoconjugates composed of antibodies coupled to extremely potent drugs have recently been shown to have improved activity against tumor cells. These immunoconjugates are very efficient in delivering toxic drugs such as geldanamycin, calicheamicin and maytansinoids to cells (Proc. Natl. Acad. Sci USA 93: 8618, 1996; J. Ntl Cancer Inst.92: 1573, 2000; Cancer Res. 60: 6089, 2000) and several of these drug-immunoconjugates are in clinical trial. They have the advantage that the small molecule drugs are not immunogenic like ricin and therefore the immunocojugate therapy can be delivered to patients multiple times.

B. Linkage to Radioisotope

The linking of such anti-CA IX antibodies to radioisotopes provides advantages to tumor treatments. Unlike chemotherapy and other forms of cancer treatment, radioimmunotherapy or the administration of a radioisotope-antibody combination directly targets the cancer cells with minimal damage to surrounding normal, healthy tissue. With this "magic bullet," the patient can be treated with much smaller quantities of radioisotopes than other forms of treatment available today. Preferred radioisotopes include yttrium$^{90}$ (90Y), indium$^{111}$ (111In), $^{131}$I, $^{99}$mTc, radiosilver-111, radiosilver-199, Actinium 225 and Bismuth$^{213}$.

Linkage of radioisotopes to antibodies may be performed with conventional bifunctional chelates. Since silver is monovalent, for radiosilver-111 and radiosilver-199 linkage, sulfur-based linkers may be used (Hazra et al., *Cell Biophys,* 24-25:1-7 (1994)). Linkage of silver radioisotopes may involved reducing the immunoglobulin with ascorbic acid. In another aspect, tiuxetan is an MX-DTPA linker chelator attached to ibritumomab to form ibritumomab tiuxetan (Zevalin) (Witzig, T. E, *Cancer Chemother Pharmacol,* 48 Suppl 1:S91-5 (2001). Ibritumomab tiuxetan can react with radioisotypes such as indium$^{111}$ (111In) or 90Y to form 111In-ibritumomab tiuxetan and 90Y-ibritumomab tiuxetan, respectively.

What is claimed:

1. A composition comprising an isolated monoclonal antibody comprising heavy and light chain polypeptides having amino acid sequences selected from the group of sequence pairs consisting of SEQ ID NOs: 2/37, 3/40, 4/64, 5/43, 6/45, 8/48, 9/32, 10/33, 11/49, 12/66, 13/39, 14/67, 15/68, 16/52, 17/54, 18/69, 19/46, 21/162, 22/56, 25/61, 26/62, 28/41, 30/36, 71/81, 72/82, 73/83, 75/85, 77/87, 79/89, 90/91, 92/93, 94/95, 96/97, 98/99, 100/101, 102/103, 125/38, 128/51, 130/57, 133/34, 136/50, 137/55, 142/44, 146/168, 150/58, 153/53, 169/175, 171/177 and 246/245, wherein said monoclonal antibody specifically binds Carbonic Anhydrase IX (CA IX).

2. The composition of claim 1, wherein said monoclonal antibody is a fully human antibody.

3. The composition of claim 1, further comprising a physiologically acceptable carrier.

4. The composition of claim 1, wherein said antibody is conjugated to a therapeutic or cytotoxic agent.

5. The conjugate of claim 4 wherein the further therapeutic agent is a toxin.

6. The conjugate of claim 4 wherein the further therapeutic agent is a radioisotope.

7. The composition of claim 1, wherein the monoclonal antibody comprises heavy and light chain polypeptides having amino acid sequences 11 and 49.

8. The composition of claim 1, wherein the monoclonal antibody comprises heavy and light chain polypeptides having amino acid sequences 21 and 162.

9. The composition of claim 1, wherein the monoclonal antibody comprises heavy and light chain polypeptides having amino acid sequences 2 and 37.

10. The composition of claim 1, wherein the monoclonal antibody comprises heavy and light chain polypeptides having amino acid sequences 92 and 93.

11. The composition of claim 1, wherein the monoclonal antibody comprises heavy and light chain polypeptides having amino acid sequences 171 and 177.

12. The composition of claim 1, wherein the monoclonal antibody comprises heavy and light chain polypeptides having amino acid sequences 30 and 36.

13. The composition of claim 1, wherein the monoclonal antibody comprises heavy and light chain polypeptides having amino acid sequences 26 and 62.

14. The composition of claim 1, wherein the monoclonal antibody comprises heavy and light chain polypeptides having amino acid sequences 169 and 175.

15. The composition of claim 1, wherein the monoclonal antibody comprises heavy and light chain polypeptides having amino acid sequences 130 and 57.

16. A composition comprising a monoclonal antibody that specifically binds CA IX tumor antigen, wherein said monoclonal antibody comprises a heavy chain polypeptide having an amino acid sequence of SEQ ID NO:25 and a light chain polypeptide having an amino acid sequence of SEQ ID NO:61.

17. The composition of claim 16, wherein the monoclonal antibody is a fully human monoclonal antibody.

18. The composition of claim 16, further comprising a physiologically acceptable carrier.

19. The composition of claim 16, wherein said monoclonal antibody is conjugated to a therapeutic agent or cytotoxic agent.

20. The composition of claim 16, wherein the monoclonal antibody is AB-MN-21.14.1.

21. A method of inhibiting cell proliferation associated with the expression of CA IX tumor antigen, comprising treating cells expressing human CA IX with an effective amount of the composition of claim 1.

22. A method for treatment of a tumor associated with the expression of CA IX in a human patient comprising administering to said patient an effective amount of the composition of claim 1.

23. The method for treatment of claim 22 wherein the tumor is selected from the group consisting of colorectal neoplasms, colorectal tumors, renal cell carcinoma (RCC), cervical carcinoma, cervical intraepithelial squamous and glandular neoplasia, esophageal tumors, and breast cancer.

24. A method for treating a tumor associated with the expression of CA IX in a human patient comprising:
    selecting a patient in need of such treatment; and
    administering to said patient a therapeutically effective amount of the composition of claim 16.

25. The method of claim 24, wherein the tumor is selected from the group consisting of: colorectal neoplasms, colorectal tumors, renal cell carcinoma (RCC), cervical carcinoma, cervical intraepithelial squamous and glandular neoplasia, esophageal tumors, and breast cancer.

* * * * *

SEQUENCE LISTING

```
<160> NUMBER OF SEQ ID NOS: 246

<210> SEQ ID NO 1
<211> LENGTH: 97
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30
```

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 2
<211> LENGTH: 118
<212> TYPE: PRT
<213> ORGANISM: Homo sapiens

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Gln Trp Leu Glu Asp Tyr Gly Met Asp Val Trp Gly Gln
                100                 105                 110

Gly Thr Thr Val Thr Val
        115

<210> SEQ ID NO 3
<211> LENGTH: 122
<212> TYPE: PRT
<213> ORGANISM: Homo sapiens

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Phe Tyr
            20                  25                  30

Tyr Trp Asn Trp Ile Arg Gln Pro Ala Gly Lys Gly Leu Glu Trp Val
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Phe Leu Glu Trp Asp Tyr Tyr Tyr Gly Met Asp Val Trp
                100                 105                 110

Gly Gln Gly Thr Thr Val Thr Val Ser Ser
        115                 120

-continued

```
<210> SEQ ID NO 4
<211> LENGTH: 120
<212> TYPE: PRT
<213> ORGANISM: Homo sapiens

<400> SEQUENCE: 4

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gly Gln Trp Leu Glu Asp Tyr Gly Met Asp Val Trp Gly Gln
            100                 105                 110

Gly Thr Thr Val Thr Val Ser Ser
            115                 120

<210> SEQ ID NO 5
<211> LENGTH: 120
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Asn
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gln Gly Phe Leu Glu Trp Leu Pro Leu Asp Val Trp Gly Gln
            100                 105                 110

Gly Thr Thr Val Thr Val Ser Ser
            115                 120

<210> SEQ ID NO 6
<211> LENGTH: 122
<212> TYPE: PRT
<213> ORGANISM: Homo sapiens

<400> SEQUENCE: 6

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Phe Tyr
             20                  25                  30

Tyr Trp Asn Trp Ile Arg Gln Pro Ala Gly Lys Gly Leu Glu Trp Val
         35                  40                  45
```

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Gly Gly Phe Leu Glu Trp Asp Tyr Tyr Gly Met Asp Val Trp
            100                 105                 110

Gly Gln Gly Thr Thr Val Thr Val Ser Ser
        115                 120

<210> SEQ ID NO 7
<211> LENGTH: 99
<212> TYPE: PRT
<213> ORGANISM: Homo sapiens

<400> SEQUENCE: 7

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 8
<211> LENGTH: 125
<212> TYPE: PRT
<213> ORGANISM: Homo sapiens

<400> SEQUENCE: 8

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Asn Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Thr Tyr Tyr Asp Ile Leu Thr Gly Tyr Pro Asp Ala Phe
            100                 105                 110

Asp Ile Trp Gly Gln Gly Thr Met Val Thr Val Ser Ser
            115                 120                 125

<210> SEQ ID NO 9
<211> LENGTH: 123

```
<212> TYPE: PRT
<213> ORGANISM: Homo sapiens

<400> SEQUENCE: 9

Gln Val Gln Leu Glu Gln Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Arg Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Ile Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Ala Gly Thr Tyr Tyr Gly Ser Gly Ser Tyr Leu Asp Tyr
            100                 105                 110

Trp Gly Gln Gly Thr Leu Val Thr Val Ser Ser
        115                 120

<210> SEQ ID NO 10
<211> LENGTH: 123
<212> TYPE: PRT
<213> ORGANISM: Homo sapiens

<400> SEQUENCE: 10

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Ala Gly Lys Tyr Tyr Gly Ser Gly Ser Tyr Leu Asp Tyr
            100                 105                 110

Trp Gly Gln Gly Thr Leu Val Thr Val Ser Ser
        115                 120

<210> SEQ ID NO 11
<211> LENGTH: 125
<212> TYPE: PRT
<213> ORGANISM: Homo sapiens

<400> SEQUENCE: 11

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Asn Thr Tyr Tyr Asn Pro Ser
```

```
                    50                  55                  60
Leu Lys Ser Arg Ile Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Thr Tyr Tyr Asp Phe Leu Thr Gly Tyr Pro Asp Ala Phe
                    100                 105                 110

Asp Ile Trp Gly Gln Gly Thr Met Val Thr Val Ser Ser
                115                 120                 125

<210> SEQ ID NO 12
<211> LENGTH: 123
<212> TYPE: PRT
<213> ORGANISM: Homo sapiens

<400> SEQUENCE: 12

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Thr Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Val Leu Leu Trp Phe Gly Glu Asp Tyr Gly Val Asp Val
                    100                 105                 110

Trp Gly Gln Gly Thr Thr Val Thr Val Ser Ser
                115                 120

<210> SEQ ID NO 13
<211> LENGTH: 120
<212> TYPE: PRT
<213> ORGANISM: Homo sapiens

<400> SEQUENCE: 13

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Asp Gly Tyr Asn Tyr Trp Tyr Phe Asp Leu Trp Gly Arg
                    100                 105                 110

Gly Thr Leu Val Thr Val Ser Ser
             115                 120
```

```
<210> SEQ ID NO 14
<211> LENGTH: 127
<212> TYPE: PRT
<213> ORGANISM: Homo sapiens

<400> SEQUENCE: 14

Gln Val Gln Leu Gln Glu Gly Pro Gly Leu Val Lys Pro Ser Gln
 1               5                  10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Tyr Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Tyr Tyr Asp Ile Leu Thr Gly Tyr Tyr Asn Tyr
            100                 105                 110

Gly Met Asp Val Trp Gly Gln Gly Thr Thr Val Thr Val Ser Ser
        115                 120                 125

<210> SEQ ID NO 15
<211> LENGTH: 122
<212> TYPE: PRT
<213> ORGANISM: Homo sapiens

<400> SEQUENCE: 15

Gln Val Gln Leu Gln Glu Gly Pro Gly Leu Val Lys Pro Ser Gln
 1               5                  10                  15

Thr Leu Ser Leu Thr Cys Thr Val Ser Gly Ser Ile Ser Ser Gly
            20                  25                  30

Val Tyr Tyr Trp Ser Trp Ile Arg Gln His Pro Gly Lys Gly Leu Glu
        35                  40                  45

Trp Ile Gly Tyr Ile Tyr Tyr Ser Arg Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asn Ala His Asp Tyr Tyr Phe Gly Met Asp Val Trp
            100                 105                 110

Gly Gln Gly Thr Thr Val Thr Val Ser Ser
        115                 120

<210> SEQ ID NO 16
<211> LENGTH: 125
<212> TYPE: PRT
<213> ORGANISM: Homo sapiens

<400> SEQUENCE: 16

Gln Val Gln Leu Gln Glu Gly Pro Gly Leu Val Lys Pro Ser Gln
 1               5                  10                  15

Thr Leu Ser Leu Thr Cys Thr Val Ser Gly Ser Ile Ser Ser Gly
            20                  25                  30

Gly Tyr Tyr Trp Asn Trp Ile Arg Gln His Pro Gly Lys Gly Leu Glu
        35                  40                  45
```

Trp Ile Gly Tyr Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Tyr Tyr Asp Ile Leu Thr Gly Tyr Pro Asp Ala Phe
                100                 105                 110

Asp Ile Trp Gly Gln Gly Thr Met Val Thr Val Ser Ser
            115                 120                 125

<210> SEQ ID NO 17
<211> LENGTH: 123
<212> TYPE: PRT
<213> ORGANISM: Homo sapiens

<400> SEQUENCE: 17

Gln Val Gln Leu Gln Glu Ser Gly Pro Gly Leu Val Lys Pro Ser Gln
  1               5                  10                  15

Thr Leu Ala Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Tyr Thr Tyr Tyr Asn Pro Ser
            50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Thr Val Thr Asp Tyr Tyr Tyr Gly Met Asp Val
                100                 105                 110

Trp Gly Gln Gly Thr Thr Val Thr Val Ser Ser
            115                 120

<210> SEQ ID NO 18
<211> LENGTH: 123
<212> TYPE: PRT
<213> ORGANISM: Homo sapiens

<400> SEQUENCE: 18

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asn Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
            50                  55                  60

Leu Lys Ser Arg Val Ile Ile Ser Val Asp Thr Ser Glu Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Arg Val Thr Asp Tyr Tyr Tyr Gly Leu Asp Val
                100                 105                 110

Trp Gly Gln Gly Thr Thr Val Thr Val Ser Ser
            115                 120

<210> SEQ ID NO 19
<211> LENGTH: 123
<212> TYPE: PRT
<213> ORGANISM: Homo sapiens

<400> SEQUENCE: 19

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asn Ser Gly
             20                  25                  30

Gly Tyr Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Ile Ile Ser Val Asp Thr Ser Glu Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Arg Val Thr Asp Tyr Tyr Tyr Gly Leu Asp Val
            100                 105                 110

Trp Gly Gln Gly Thr Thr Val Thr Val Ser Ser
        115                 120
```

<210> SEQ ID NO 20
<211> LENGTH: 99
<212> TYPE: PRT
<213> ORGANISM: Homo sapiens

<400> SEQUENCE: 20

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg
```

<210> SEQ ID NO 21
<211> LENGTH: 115
<212> TYPE: PRT
<213> ORGANISM: Homo sapiens

<400> SEQUENCE: 21

```
Gln Leu Glu Gln Ser Gly Pro Gly Leu Val Lys Pro Ser Glu Thr Leu
  1               5                  10                  15

Ser Leu Thr Cys Thr Val Ser Asp Gly Ser Ile Ser Ser Ser Ser Tyr
             20                  25                  30

Tyr Trp Gly Trp Ile Arg Gln Pro Pro Gly Lys Gly Leu Glu Trp Ile
         35                  40                  45

Gly Ser Ile Tyr Tyr Ser Gly Ser Thr Tyr Tyr Asn Pro Ser Leu Lys
```

```
                50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg His Gly Ser Phe Phe Asp Tyr Trp Gly Gln Gly Thr Leu Val Thr
                100                 105                 110

Val Ser Ser
        115

<210> SEQ ID NO 22
<211> LENGTH: 117
<212> TYPE: PRT
<213> ORGANISM: Homo sapiens

<400> SEQUENCE: 22

Gln Leu Gln Leu Gln Glu Ser Gly Pro Gly Leu Val Lys Pro Ser Glu
  1               5                  10                  15

Thr Leu Ser Leu Thr Cys Thr Val Ser Asp Gly Ser Ile Ser Ser Ser
                 20                  25                  30

Ser Tyr Tyr Trp Gly Trp Ile Arg Gln Pro Pro Gly Lys Gly Leu Glu
                 35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg His Gly Ser Phe Phe Asp Tyr Trp Gly Gln Gly Thr Leu
                100                 105                 110

Val Thr Val Ser Ser
        115

<210> SEQ ID NO 23
<211> LENGTH: 97
<212> TYPE: PRT
<213> ORGANISM: Homo sapiens

<400> SEQUENCE: 23

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
                 35                  40                  45

Gly Tyr Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 24
<211> LENGTH: 122
<212> TYPE: PRT
<213> ORGANISM: Homo sapiens
```

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Tyr Asp Ile Leu Thr Gly Tyr Asp Tyr Phe Asp Tyr Trp
            100                 105                 110

Gly Gln Gly Thr Leu Val Thr Val Ser Ser
        115                 120

<210> SEQ ID NO 25
<211> LENGTH: 122
<212> TYPE: PRT
<213> ORGANISM: Homo sapiens

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Tyr Asp Phe Leu Thr Gly Tyr Asp Tyr Phe Asp Tyr Trp
            100                 105                 110

Gly Gln Gly Thr Leu Val Thr Val Ser Ser
        115                 120

<210> SEQ ID NO 26
<211> LENGTH: 124
<212> TYPE: PRT
<213> ORGANISM: Homo sapiens

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
    50                  55                  60

-continued

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gln His Ser Ser Phe Tyr Tyr Tyr Tyr Gly Met Asp
            100                 105                 110

Val Trp Gly Gln Gly Thr Thr Val Thr Val Ser Ser
        115                 120

<210> SEQ ID NO 27
<211> LENGTH: 122
<212> TYPE: PRT
<213> ORGANISM: Homo sapiens

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Tyr Asp Ile Leu Thr Gly Tyr Asp Tyr Phe Asp Tyr Trp
            100                 105                 110

Gly Gln Gly Thr Leu Val Thr Val Ser Ser
        115                 120

<210> SEQ ID NO 28
<211> LENGTH: 123
<212> TYPE: PRT
<213> ORGANISM: Homo sapiens

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asn
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Lys Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Tyr Tyr Asp Phe Leu Thr Gly Tyr Tyr His Val Phe Asp Tyr
            100                 105                 110

Trp Gly Gln Gly Thr Leu Val Thr Val Ser Ser
        115                 120

<210> SEQ ID NO 29
<211> LENGTH: 122

```
<212> TYPE: PRT
<213> ORGANISM: Homo sapiens

<400> SEQUENCE: 29

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Tyr Asp Phe Leu Thr Gly Tyr Asp Tyr Phe Asp Tyr Trp
            100                 105                 110

Gly Gln Gly Thr Leu Val Thr Val Ser Ser
        115                 120

<210> SEQ ID NO 30
<211> LENGTH: 119
<212> TYPE: PRT
<213> ORGANISM: Homo sapiens

<400> SEQUENCE: 30

Ser Gly Pro Gly Leu Val Lys Pro Ser Glu Thr Leu Ser Leu Thr Cys
 1               5                   10                  15

Thr Val Ser Gly Gly Ser Ile Ser Ser Tyr Tyr Trp Ser Trp Ile Arg
            20                  25                  30

Gln Pro Pro Gly Lys Gly Leu Glu Trp Ile Gly Tyr Ile Tyr Tyr Ser
        35                  40                  45

Gly Ser Thr Asn Tyr Asn Pro Ser Leu Lys Ser Arg Val Thr Ile Ser
    50                  55                  60

Val Asp Thr Ser Lys Asn Gln Phe Ser Leu Lys Leu Thr Ser Val Thr
65                  70                  75                  80

Ala Ala Asp Thr Ala Val Tyr Tyr Cys Ala Arg Asp Gln His Ser Ser
                85                  90                  95

Ser Val Tyr Tyr Tyr Tyr Tyr Gly Met Asp Val Trp Gly Gln Gly Thr
            100                 105                 110

Thr Val Thr Val Ser Ser Ala
        115

<210> SEQ ID NO 31
<211> LENGTH: 100
<212> TYPE: PRT
<213> ORGANISM: Homo sapiens

<400> SEQUENCE: 31

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro
            100

<210> SEQ ID NO 32
<211> LENGTH: 112
<212> TYPE: PRT
<213> ORGANISM: Homo sapiens

<400> SEQUENCE: 32

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Cys
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
            100                 105                 110

<210> SEQ ID NO 33
<211> LENGTH: 112
<212> TYPE: PRT
<213> ORGANISM: Homo sapiens

<400> SEQUENCE: 33

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Pro Leu Thr Phe Gly Gly Gly Thr Lys Val Glu Ile Lys
            100                 105                 110

<210> SEQ ID NO 34
<211> LENGTH: 112
<212> TYPE: PRT
<213> ORGANISM: Homo sapiens

<400> SEQUENCE: 34

Asp Ile Val Met Thr Gln Ser Pro Leu Ser Leu Pro Val Thr Pro Gly
  1               5                  10                  15
```

```
Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
        35                  40                  45

Pro Gln Phe Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Ser Phe Gly Gln Gly Thr Lys Leu Glu Ile Lys
            100                 105                 110
```

<210> SEQ ID NO 35
<211> LENGTH: 96
<212> TYPE: PRT
<213> ORGANISM: Homo sapiens

<400> SEQUENCE: 35

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 36
<211> LENGTH: 108
<212> TYPE: PRT
<213> ORGANISM: Homo sapiens

<400> SEQUENCE: 36

```
Glu Thr Gln Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Tyr Ile Asn
                20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Glu Val Glu Ile Lys Arg
            100                 105
```

<210> SEQ ID NO 37
<211> LENGTH: 108
<212> TYPE: PRT
<213> ORGANISM: Homo sapiens

```
<400> SEQUENCE: 37

Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Val Phe Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Pro Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 38
<211> LENGTH: 107
<212> TYPE: PRT
<213> ORGANISM: Homo sapiens

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys Gln Gln Tyr Gly Ser Ser Leu
                85                  90                  95

Thr Phe Gly Gly Gly Thr Lys Val Glu Ile Lys
            100                 105

<210> SEQ ID NO 39
<211> LENGTH: 108
<212> TYPE: PRT
<213> ORGANISM: Homo sapiens

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Phe Ser Pro
                85                  90                  95
```

```
Leu Thr Phe Gly Gly Gly Thr Lys Val Glu Ile Lys
            100                 105
```

<210> SEQ ID NO 40
<211> LENGTH: 107
<212> TYPE: PRT
<213> ORGANISM: Homo sapiens

<400> SEQUENCE: 40

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Val
                85                  90                  95

Thr Phe Gly Gly Gly Thr Lys Val Glu Ile Lys
            100                 105
```

<210> SEQ ID NO 41
<211> LENGTH: 109
<212> TYPE: PRT
<213> ORGANISM: Homo sapiens

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Asn
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Arg Phe Ser Phe Gly Gln Gly Thr Lys Leu Glu Ile Lys
            100                 105
```

<210> SEQ ID NO 42
<211> LENGTH: 108
<212> TYPE: PRT
<213> ORGANISM: Homo sapiens

<400> SEQUENCE: 42

```
Glu Ile Val Leu Thr Gln Ser Pro Gly Thr Leu Ser Leu Ser Pro Gly
1               5                   10                  15

Glu Arg Ala Thr Leu Ser Cys Trp Ala Ser Gln Ser Val Phe Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
            50                  55                  60
Gly Ser Gly Ser Gly Thr Asp Phe Pro Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys
            100                 105
```

<210> SEQ ID NO 43
<211> LENGTH: 108
<212> TYPE: PRT
<213> ORGANISM: Homo sapiens

<400> SEQUENCE: 43

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Thr Ser Pro
                 85                  90                  95

Ile Thr Phe Gly Gln Gly Thr Arg Leu Glu Ile Lys
            100                 105
```

<210> SEQ ID NO 44
<211> LENGTH: 107
<212> TYPE: PRT
<213> ORGANISM: Homo sapiens

<400> SEQUENCE: 44

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Ser Cys Gln Gln Tyr Gly Ser Ser Leu
                 85                  90                  95

Thr Phe Gly Gly Gly Thr Lys Val Glu Ile Lys
            100                 105
```

<210> SEQ ID NO 45
<211> LENGTH: 107
<212> TYPE: PRT
<213> ORGANISM: Homo sapiens

<400> SEQUENCE: 45

```
Glu Ile Val Leu Thr Gln Ser Pro Gly Thr Leu Ser Leu Ser Pro Gly
 1               5                  10                  15
```

Glu Arg Ala Thr Leu Ser Cys Arg Ala Ser Gln Ser Val Ser Val Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Val
                85                  90                  95

Thr Phe Gly Gly Gly Thr Lys Val Glu Ile Lys
            100                 105

<210> SEQ ID NO 46
<211> LENGTH: 109
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Asn
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Arg Phe Ser Phe Gly Gln Gly Thr Lys Leu Glu Ile Lys
            100                 105

<210> SEQ ID NO 47
<211> LENGTH: 94
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Leu Gln His Asn Ser Tyr Pro
                85                  90

<210> SEQ ID NO 48
<211> LENGTH: 107
<212> TYPE: PRT
<213> ORGANISM: Homo sapiens

```
<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Cys Ala Ala Ser Ser Leu Gln Ser Gly Val Pro Ser Ser Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Ser Glu Phe Thr Leu Thr Ile Ser Ser Leu Gln Pro
65                  70                  75                  80

Glu Asp Phe Ala Thr Tyr Tyr Cys Leu Gln Tyr His Ser Tyr Pro Trp
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Tyr Asp
            20                  25                  30

Leu Gly Trp Tyr Gln Gln Lys Pro Gly Lys Ala Pro Lys Arg Leu Ile
        35                  40                  45

Tyr Ala Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95
```

```
Thr Phe Gly Pro Gly Thr Lys Val Asp Ile Lys
            100                 105
```

<210> SEQ ID NO 51
<211> LENGTH: 107
<212> TYPE: PRT
<213> ORGANISM: Homo sapiens

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105
```

<210> SEQ ID NO 52
<211> LENGTH: 107
<212> TYPE: PRT
<213> ORGANISM: Homo sapiens

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Cys Ala Ala Ser Ser Leu Gln Ser Gly Val Pro Ser Ser Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 53
<211> LENGTH: 107
<212> TYPE: PRT
<213> ORGANISM: Homo sapiens

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
```

```
                    50                   55                   60
Ser Gly Ser Gly Thr Glu Phe Thr Leu Thr Ile Ser Ser Leu Gln Pro
 65                  70                  75                  80

Glu Asp Phe Thr Thr Tyr Tyr Cys Leu Gln Tyr Lys Ser Tyr Pro Trp
                 85                  90                  95

Thr Phe Gly Gln Gly Thr Lys Val Glu Ile Lys
            100                 105

<210> SEQ ID NO 54
<211> LENGTH: 107
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ala Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Ser Glu Phe Thr Leu Thr Ile Ser Ser Leu Gln Pro
 65                  70                  75                  80

Glu Asp Phe Ala Thr Tyr Tyr Cys Leu Gln Tyr His Ser Tyr Pro Trp
                 85                  90                  95

Thr Phe Gly Gln Gly Thr Lys Val Glu Ile Lys
            100                 105

<210> SEQ ID NO 55
<211> LENGTH: 107
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Tyr Asp
                 20                  25                  30

Leu Gly Trp Tyr Gln Gln Lys Pro Gly Lys Ala Pro Lys Arg Leu Ile
             35                  40                  45

Tyr Ala Thr Ser Asn Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Thr Phe Gly Pro Gly Thr Lys Val Asp Ile Lys
            100                 105

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Thr Thr Tyr Tyr Cys Leu Gln Tyr Lys Ser Tyr Pro Trp
                85                  90                  95

Thr Phe Gly Gln Gly Thr Lys Val Glu Ile Lys
            100                 105

<210> SEQ ID NO 57
<211> LENGTH: 107
<212> TYPE: PRT
<213> ORGANISM: Homo sapiens

<400> SEQUENCE: 57

Asp Ile Arg Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 58
<211> LENGTH: 107
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Tyr Ser Tyr Pro Leu
                85                  90                  95

Thr Phe Gly Gly Gly Thr Lys Val Glu Ile Lys
            100                 105

<210> SEQ ID NO 59
```

<211> LENGTH: 95
<212> TYPE: PRT
<213> ORGANISM: Homo sapiens

<400> SEQUENCE: 59

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 60
<211> LENGTH: 107
<212> TYPE: PRT
<213> ORGANISM: Homo sapiens

<400> SEQUENCE: 60

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ile Trp
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
                100                 105

<210> SEQ ID NO 61
<211> LENGTH: 107
<212> TYPE: PRT
<213> ORGANISM: Homo sapiens

<400> SEQUENCE: 61

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

```
Thr Phe Gly Gln Gly Thr Arg Leu Glu Ile Lys
            100                 105
```

<210> SEQ ID NO 62
<211> LENGTH: 107
<212> TYPE: PRT
<213> ORGANISM: Homo sapiens

<400> SEQUENCE: 62

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Pro Gly Thr Lys Val Asp Ile Lys
            100                 105
```

<210> SEQ ID NO 63
<211> LENGTH: 107
<212> TYPE: PRT
<213> ORGANISM: Homo sapiens

<400> SEQUENCE: 63

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ile Trp
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105
```

<210> SEQ ID NO 64
<211> LENGTH: 107
<212> TYPE: PRT
<213> ORGANISM: Homo sapiens

<400> SEQUENCE: 64

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Ile
                     85                  90                  95

Thr Phe Gly Gln Gly Thr Arg Leu Glu Ile Lys
                100                 105

<210> SEQ ID NO 65
<211> LENGTH: 95
<212> TYPE: PRT
<213> ORGANISM: Homo sapiens

<400> SEQUENCE: 65

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                     85                  90                  95

<210> SEQ ID NO 66
<211> LENGTH: 107
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Thr Asn Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Thr Pro Leu
                     85                  90                  95

Thr Phe Gly Gly Gly Thr Glu Val Glu Ile Lys
                100                 105

<210> SEQ ID NO 67
<211> LENGTH: 107
<212> TYPE: PRT
<213> ORGANISM: Homo sapiens

<400> SEQUENCE: 67

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30
```

Leu Asn Trp Tyr Gln Gln Lys Pro Gly Lys Val Pro Lys Leu Leu Ile
            35                  40                  45

Tyr Val Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Val Pro Lys Leu Leu Ile
            35                  40                  45

Tyr Val Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 69
<211> LENGTH: 107
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Thr Pro Leu
                85                  90                  95

Thr Phe Gly Gly Gly Thr Glu Val Glu Ile Lys
            100                 105

<210> SEQ ID NO 70
<211> LENGTH: 108
<212> TYPE: PRT
<213> ORGANISM: Homo sapiens

```
<400> SEQUENCE: 70

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gln Gly Thr Thr Val Thr Val Ser Ser
            100                 105

<210> SEQ ID NO 71
<211> LENGTH: 122
<212> TYPE: PRT
<213> ORGANISM: Homo sapiens

<400> SEQUENCE: 71

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Thr Arg Thr Ile Phe Gly Val Val Ser Gly Met Asp Val Trp
            100                 105                 110

Gly Gln Gly Thr Thr Val Thr Val Ser Ser
        115                 120

<210> SEQ ID NO 72
<211> LENGTH: 122
<212> TYPE: PRT
<213> ORGANISM: Homo sapiens

<400> SEQUENCE: 72

Gln Val Gln Leu Gln Glu Ser Gly Pro Gly Leu Val Lys Pro Ser Glu
 1               5                  10                  15

Thr Leu Ser Leu Thr Cys Ser Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Asn Asn His Phe Ser Leu
65                  70                  75                  80
```

```
Lys Leu Ser Ser Val Thr Ala Ala Asp Thr Ala Val Tyr Tyr Cys Ala
                85                  90                  95

Arg Asp Thr Arg Thr Ile Phe Gly Val Val Ser Gly Met Asp Val Trp
            100                 105                 110

Gly Gln Gly Thr Thr Val Thr Val Ser Ser
        115                 120

<210> SEQ ID NO 73
<211> LENGTH: 122
<212> TYPE: PRT
<213> ORGANISM: Homo sapiens

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Phe Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Thr Arg Thr Ile Phe Gly Val Val Ser Gly Met Asp Val Trp
            100                 105                 110

Gly Gln Gly Thr Thr Val Thr Val Ser Ser
        115                 120

<210> SEQ ID NO 74
<211> LENGTH: 110
<212> TYPE: PRT
<213> ORGANISM: Homo sapiens

<400> SEQUENCE: 74

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Gly Gln Gly Thr Leu Val Thr Val Ser Ser
            100                 105                 110

<210> SEQ ID NO 75
<211> LENGTH: 124
<212> TYPE: PRT
<213> ORGANISM: Homo sapiens

<400> SEQUENCE: 75

Gln Val Gln Leu Gln Glu Ser Gly Pro Gly Leu Val Lys Pro Ser Gln
```

-continued

```
                1               5                  10                  15
Thr Leu Ser Leu Thr Cys Thr Val Ser Gly Gly Ser Ile Ser Ser Gly
                    20                  25                  30

Gly Tyr Tyr Trp Ser Trp Ile Arg Gln His Pro Gly Lys Gly Leu Glu
                    35                  40                  45

Trp Ile Gly Tyr Ile Tyr Tyr Ser Gly Ser Thr Tyr Tyr Asn Pro Ser
                    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                    85                  90                  95

Cys Ala Arg Glu Asn Tyr Asp Ile Leu Thr Gly Phe Asn Trp Phe Asp
                    100                 105                 110

Pro Trp Gly Gln Gly Thr Leu Val Thr Val Ser Ser
                    115                 120
```

<210> SEQ ID NO 76
<211> LENGTH: 109
<212> TYPE: PRT
<213> ORGANISM: Homo sapiens

<400> SEQUENCE: 76

```
Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
                    20                  25                  30

Ser Met Asn Trp Val Arg Gln Ala Pro Gly Lys Gly Leu Glu Trp Val
                    35                  40                  45

Ser Ser Ile Ser Ser Ser Ser Tyr Ile Tyr Tyr Ala Asp Ser Val
                    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Trp Gly Gln Gly Thr Leu Val Thr Val Ser Ser
                    100                 105
```

<210> SEQ ID NO 77
<211> LENGTH: 117
<212> TYPE: PRT
<213> ORGANISM: Homo sapiens

<400> SEQUENCE: 77

```
Glu Val Gln Leu Val Glu Phe Gly Gly Gly Leu Val Lys Pro Gly Gly
1               5                  10                  15

Ser Leu Arg Leu Ser Cys Ala Ala Ser Gly Phe Thr Phe Ser Ser Phe
                    20                  25                  30

Arg Met Asn Trp Val Arg Gln Ala Pro Gly Glu Gly Leu Glu Trp Val
                    35                  40                  45

Ser Ser Ile Thr Ser Ser Ser Tyr Ile Tyr Tyr Ala Asp Ser Val
                    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Phe Thr Ala Met Ala Leu Asp Tyr Trp Gly Gln Gly Thr Leu
```

-continued

```
                100                 105                 110
Val Thr Val Ser Ser
        115

<210> SEQ ID NO 78
<211> LENGTH: 108
<212> TYPE: PRT
<213> ORGANISM: Homo sapiens

<400> SEQUENCE: 78

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Gly Gln Gly Thr Thr Val Thr Val Ser Ser
            100                 105

<210> SEQ ID NO 79
<211> LENGTH: 118
<212> TYPE: PRT
<213> ORGANISM: Homo sapiens

<400> SEQUENCE: 79

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Leu Ile Thr Gly Pro Tyr Gly Met Asp Val Trp Gly Gln Gly Thr
            100                 105                 110

Thr Val Thr Val Ser Ser
        115

<210> SEQ ID NO 80
<211> LENGTH: 107
<212> TYPE: PRT
<213> ORGANISM: Homo sapiens

<400> SEQUENCE: 80

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30
```

```
Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 81
<211> LENGTH: 107
<212> TYPE: PRT
<213> ORGANISM: Homo sapiens

<400> SEQUENCE: 81

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Arg Ser Leu
                85                  90                  95

Thr Phe Gly Gly Gly Thr Lys Val Glu Ile Lys
            100                 105

<210> SEQ ID NO 82
<211> LENGTH: 107
<212> TYPE: PRT
<213> ORGANISM: Homo sapiens

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Thr Val Tyr Ser Thr
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln His Tyr Gly Arg Ser Leu
                85                  90                  95

Thr Phe Gly Gly Gly Thr Lys Val Glu Ile Lys
            100                 105

<210> SEQ ID NO 83
<211> LENGTH: 107
<212> TYPE: PRT
<213> ORGANISM: Homo sapiens
```

```
<400> SEQUENCE: 83

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Asp Asp Phe Ala Val Tyr Tyr Cys Gln His Tyr Gly Arg Ser Leu
                85                  90                  95

Thr Phe Gly Gly Gly Thr Lys Val Glu Ile Lys
            100                 105

<210> SEQ ID NO 84
<211> LENGTH: 106
<212> TYPE: PRT
<213> ORGANISM: Homo sapiens

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Trp Thr
                85                  90                  95

Phe Gly Gln Gly Thr Lys Val Glu Ile Lys
            100                 105

<210> SEQ ID NO 85
<211> LENGTH: 106
<212> TYPE: PRT
<213> ORGANISM: Homo sapiens

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Ser Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Arg Thr
                85                  90                  95
```

Phe Gly Gln Gly Thr Lys Val Glu Ile Lys
            100                 105

<210> SEQ ID NO 86
<211> LENGTH: 107
<212> TYPE: PRT
<213> ORGANISM: Homo sapiens

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys
            100                 105

<210> SEQ ID NO 87
<211> LENGTH: 107
<212> TYPE: PRT
<213> ORGANISM: Homo sapiens

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Phe Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Val Tyr Tyr Cys Leu Lys Tyr Asn Ser Ala Pro Trp
                85                  90                  95

Thr Phe Gly Gln Gly Thr Lys Val Glu Ile Lys
            100                 105

<210> SEQ ID NO 88
<211> LENGTH: 107
<212> TYPE: PRT
<213> ORGANISM: Homo sapiens

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 89
<211> LENGTH: 107
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Ser Ser Leu Phe
                85                  90                  95

Thr Phe Gly Pro Gly Thr Lys Val Asp Ile Lys
            100                 105

<210> SEQ ID NO 90
<211> LENGTH: 141
<212> TYPE: PRT
<213> ORGANISM: Homo sapiens

<400> SEQUENCE: 90

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Thr Arg Thr Ile Phe Gly Val Val Ser Gly Met
        115                 120                 125

Asp Val Trp Gly Gln Gly Thr Thr Val Thr Val Ser Ser
    130                 135                 140

<210> SEQ ID NO 91
<211> LENGTH: 127
<212> TYPE: PRT

<213> ORGANISM: Homo sapiens

<400> SEQUENCE: 91

```
Met Glu Ala Pro Ala Gln Leu Leu Phe Leu Leu Leu Trp Leu Pro
 1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Tyr Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Pro Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln His Tyr
            100                 105                 110

Gly Arg Ser Leu Thr Phe Gly Gly Gly Thr Lys Val Glu Ile Lys
        115                 120                 125
```

<210> SEQ ID NO 92
<211> LENGTH: 141
<212> TYPE: PRT
<213> ORGANISM: Homo sapiens

<400> SEQUENCE: 92

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Glu Thr Leu Ser Leu Thr Cys Ser Val Ser Gly Gly Ser Ile
            35                  40                  45

Ser Ser Tyr Tyr Trp Ser Trp Ile Arg Gln Pro Pro Gly Lys Gly Leu
        50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Asn Asn His
                85                  90                  95

Phe Ser Leu Lys Leu Ser Ser Val Thr Ala Ala Asp Thr Ala Val Tyr
            100                 105                 110

Tyr Cys Ala Arg Asp Thr Arg Thr Ile Phe Gly Val Val Ser Gly Met
        115                 120                 125

Asp Val Trp Gly Gln Gly Thr Thr Val Thr Val Ser Ser
    130                 135                 140
```

<210> SEQ ID NO 93
<211> LENGTH: 127
<212> TYPE: PRT
<213> ORGANISM: Homo sapiens

<400> SEQUENCE: 93

```
Met Glu Thr Pro Ala Gln Leu Leu Phe Leu Leu Leu Trp Leu Pro
 1               5                  10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Thr Ser Gln Thr
            35                  40                  45
```

```
Val Tyr Ser Thr Tyr Leu Ala Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Cys Gln His Tyr
                100                 105                 110

Gly Arg Ser Leu Thr Phe Gly Gly Gly Thr Lys Val Glu Ile Lys
            115                 120                 125

<210> SEQ ID NO 94
<211> LENGTH: 141
<212> TYPE: PRT
<213> ORGANISM: Homo sapiens

<400> SEQUENCE: 94

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Thr Val Ser Gly Gly Ser Ile
         35                  40                  45

Ser Ser Tyr Tyr Trp Ser Trp Ile Arg Gln Pro Pro Gly Lys Gly Leu
     50                  55                  60

Glu Trp Ile Gly Tyr Ile Phe Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
                100                 105                 110

Tyr Cys Ala Arg Asp Thr Arg Thr Ile Phe Gly Val Val Ser Gly Met
            115                 120                 125

Asp Val Trp Gly Gln Gly Thr Thr Val Thr Val Ser Ser
        130                 135                 140

<210> SEQ ID NO 95
<211> LENGTH: 127
<212> TYPE: PRT
<213> ORGANISM: Homo sapiens

<400> SEQUENCE: 95

Met Glu Ala Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Tyr Ser Ser Tyr Leu Ala Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Asp Phe Ala Val Tyr Tyr Cys Gln His Tyr
                100                 105                 110
```

```
Gly Arg Ser Leu Thr Phe Gly Gly Thr Lys Val Glu Ile Lys
        115                 120                 125

<210> SEQ ID NO 96
<211> LENGTH: 143
<212> TYPE: PRT
<213> ORGANISM: Homo sapiens

<400> SEQUENCE: 96

Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
               20                  25                  30

Pro Ser Gln Thr Leu Ser Leu Thr Cys Thr Val Ser Gly Gly Ser Ile
           35                  40                  45

Ser Ser Gly Gly Tyr Tyr Trp Ser Trp Ile Arg Gln His Pro Gly Lys
       50                  55                  60

Gly Leu Glu Trp Ile Gly Tyr Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg Glu Asn Tyr Asp Ile Leu Thr Gly Phe Asn
        115                 120                 125

Trp Phe Asp Pro Trp Gly Gln Gly Thr Leu Val Thr Val Ser Ser
    130                 135                 140

<210> SEQ ID NO 97
<211> LENGTH: 126
<212> TYPE: PRT
<213> ORGANISM: Homo sapiens

<400> SEQUENCE: 97

Met Arg Val Pro Ala Gln Leu Leu Gly Leu Leu Leu Leu Trp Phe Pro
  1               5                  10                  15

Gly Ser Arg Cys Asp Ile Gln Met Thr Gln Ser Pro Ser Ser Val Ser
               20                  25                  30

Ala Ser Val Gly Asp Arg Val Thr Ile Thr Cys Arg Ala Ser Gln Gly
           35                  40                  45

Ile Ser Ser Trp Leu Ala Trp Tyr Gln Gln Lys Pro Gly Lys Ala Pro
       50                  55                  60

Lys Val Leu Ile Tyr Ser Thr Ser Arg Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Ala Asp
            100                 105                 110

Ser Phe Arg Thr Phe Gly Gln Gly Thr Lys Val Glu Ile Lys
        115                 120                 125

<210> SEQ ID NO 98
<211> LENGTH: 136
<212> TYPE: PRT
<213> ORGANISM: Homo sapiens

<400> SEQUENCE: 98
```

```
Met Glu Leu Gly Leu Arg Trp Val Phe Leu Val Ala Ile Leu Glu Gly
 1               5                  10                  15

Val Gln Cys Glu Val Gln Leu Val Glu Phe Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Arg Met Asn Trp Val Arg Gln Ala Pro Gly Glu Gly Leu
50                  55                  60

Glu Trp Val Ser Ser Ile Thr Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Phe Thr Ala Met Ala Leu Asp Tyr Trp Gly Gln
        115                 120                 125

Gly Thr Leu Val Thr Val Ser Ser
        130                 135
```

<210> SEQ ID NO 99
<211> LENGTH: 127
<212> TYPE: PRT
<213> ORGANISM: Homo sapiens

<400> SEQUENCE: 99

```
Met Arg Val Pro Ala Gln Leu Leu Gly Leu Leu Leu Leu Trp Leu Pro
 1               5                  10                  15

Asp Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Phe Asn Tyr Leu Ala Trp Tyr Gln Gln Lys Pro Gly Lys Val Pro
50                  55                  60

Lys Leu Leu Ile Tyr Ala Ala Ser Thr Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Val Tyr Tyr Cys Leu Lys Tyr Asn
            100                 105                 110

Ser Ala Pro Trp Thr Phe Gly Gln Gly Thr Lys Val Glu Ile Lys
        115                 120                 125
```

<210> SEQ ID NO 100
<211> LENGTH: 137
<212> TYPE: PRT
<213> ORGANISM: Homo sapiens

<400> SEQUENCE: 100

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Ala Gly Lys Gly Leu
50                  55                  60
```

```
Glu Trp Ile Gly Arg Ile Tyr Thr Ser Gly Ser Thr Asn Tyr Asn Pro
 65                  70                  75                  80

Ser Leu Lys Ser Arg Val Thr Met Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg Leu Ile Thr Gly Pro Tyr Gly Met Asp Val Trp Gly
        115                 120                 125

Gln Gly Thr Thr Val Thr Val Ser Ser
    130                 135

<210> SEQ ID NO 101
<211> LENGTH: 127
<212> TYPE: PRT
<213> ORGANISM: Homo sapiens

<400> SEQUENCE: 101

Met Arg Val Pro Ala Gln Leu Leu Gly Leu Leu Leu Leu Trp Leu Arg
  1               5                  10                  15

Gly Ala Arg Cys Asp Ile Gln Met Thr Gln Ser Pro Ser Ser Leu Ser
             20                  25                  30

Ala Ser Val Gly Asp Arg Val Thr Ile Thr Cys Arg Ala Ser Gln Ser
         35                  40                  45

Ile Ser Ser Tyr Leu Asn Trp Tyr Gln Gln Lys Pro Gly Lys Ala Pro
     50                  55                  60

Lys Leu Leu Ile Tyr Thr Ala Ser Asn Leu Arg Gly Gly Val Pro Ser
 65                  70                  75                  80

Arg Phe Ser Gly Ser Gly Ser Gly Thr Asp Phe Thr Leu Thr Ile Ser
                 85                  90                  95

Gly Leu Gln Pro Glu Asp Phe Ala Thr Tyr Tyr Cys Gln Gln Ser Tyr
            100                 105                 110

Ser Ser Leu Phe Thr Phe Gly Pro Gly Thr Lys Val Asp Ile Lys
        115                 120                 125

<210> SEQ ID NO 102
<211> LENGTH: 120
<212> TYPE: PRT
<213> ORGANISM: Homo sapiens

<400> SEQUENCE: 102

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gly Gln Trp Leu Glu Asp Tyr Gly Met Asp Val Trp Gly Gln
            100                 105                 110

Gly Thr Thr Val Thr Val Ser Ser
        115                 120
```

<210> SEQ ID NO 103
<211> LENGTH: 108
<212> TYPE: PRT
<213> ORGANISM: Homo sapiens

<400> SEQUENCE: 103

Glu Ile Val Leu Thr Gln Ser Pro Gly Thr Leu Ser Leu Ser Pro Gly
 1               5                  10                  15

Glu Arg Ala Thr Leu Ser Cys Trp Ala Ser Gln Ser Val Phe Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Pro Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 104
<211> LENGTH: 423
<212> TYPE: DNA
<213> ORGANISM: Homo sapiens

<400> SEQUENCE: 104
atgaaacacc tgtggttctt cctcctcctg gtggcagctc ccagatgggt cctgtcccag      60
gtgcagctgc aggagtcggg cccaggactg gtgaagcctt cggagaccct gtccctcacc     120
tgcactgtct ctggtggctc catcagtagt tactactgga gctggatccg cagccccca     180 gggaagggac tggagtggat tgggtatatc tattacagtg ggagcaccaa ctacaacccc     240
tccctcaaga gtcgagtcac catatcagta gacacgtcca agaaccagtt ctctctgaag     300
ctgagctctg tgaccgctgc ggacacggcc gtgtattact gtgcgagaga tacccgtacg     360 attttggag tggttagcgg tatggacgtc tggggccaag gaccacggt caccgtctcc      420 tca                                                                  423

<210> SEQ ID NO 105
<211> LENGTH: 384
<212> TYPE: DNA
<213> ORGANISM: Homo sapiens

<400> SEQUENCE: 105
atggaagccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgtttac agcagttact tagcctggta tcagcagaaa     180
cctggccagg ctcccaggct cctcatctat ggtgcatcca gcagggcccc tggcatccca     240
gacaggttca gtggcagtgg gtctgggaca gacttcactc tcaccatcag cagactggag     300
cctgaagatt ttgcagtgta ttactgtcag cactatggtc gctcactcac tttcggcgga     360
gggaccaagg tggagatcaa acga                                           384

<210> SEQ ID NO 106
<211> LENGTH: 423
<212> TYPE: DNA

<213> ORGANISM: Homo sapiens

<400> SEQUENCE: 106

| | |
|---|---|
| atgaagcatc tgtggttctt ccttctcctg gtggcagctc ccagatgggt cctgtcccag | 60 |
| gtgcagctgc aggagtcggg cccaggactg gtgaagcctt cggagaccct gtccctcacc | 120 |
| tgctctgtct ctggtggctc catcagtagt tactactgga gctggatccg gcagccccca | 180 |
| gggaagggac tggaatggat tgggtatatc tattacagtg ggagcaccaa ctacaacccc | 240 |
| tccctcaaga gtcgagtcac catatcggta gacacgtcca ataaccattt ctccctgaag | 300 |
| ctgagctctg tgaccgctgc ggacacggcc gtgtattact gtgcgagaga tacccgtacg | 360 |
| attttttggag tggttagcgg tatggacgtc tggggccaag gaccacggt caccgtctcc | 420 |
| tca | 423 |

<210> SEQ ID NO 107
<211> LENGTH: 384
<212> TYPE: DNA
<213> ORGANISM: Homo sapiens

<400> SEQUENCE: 107

| | |
|---|---|
| atggaaaccc cagctcagct tctcttcctc ctgctactct ggctcccaga taccaccgga | 60 |
| gaaattgtgt tgacgcagtc tccaggcacc ctgtctttgt ctccagggga aagagccacc | 120 |
| ctctcctgca ggaccagtca gactgtttac agcacctact tagcctggta ccagcagaaa | 180 |
| cctggccagg ctcccaggct cctcatctat ggtgcatcca gcagggccac tggcatccca | 240 |
| gacaggttca gtggcagtgg gtctgggaca gacttcactc tcaccatcag cagactggag | 300 |
| cctgaagatt ttgcagtgtt ttattgtcag cactatggtc gctcactcac tttcggcgga | 360 |
| gggaccaagg tggagatcaa acga | 384 |

<210> SEQ ID NO 108
<211> LENGTH: 423
<212> TYPE: DNA
<213> ORGANISM: Homo sapiens

<400> SEQUENCE: 108

| | |
|---|---|
| atgaagcatc tgtggttctt ccttctcctg gtggcagctc ccagatgggt cctgtcccag | 60 |
| gtgcagctgc aggagtcggg cccaggactg gtgaagcctt cggagaccct gtccctcacc | 120 |
| tgcactgtct ctggtggctc catcagtagt tactactgga gctggatccg gcagccccca | 180 |
| gggaagggac tggagtggat tgggtatatc ttttacagtg ggagcaccaa ctacaacccc | 240 |
| tccctcaaga gtcgagtcac catatcagta gacacgtcca agaaccagtt ctccctgaag | 300 |
| ctgagctctg tgaccgctgc ggacacggcc gtgtattact gtgcgagaga tacccgtacg | 360 |
| attttttggag tggttagcgg tatggacgtc tggggccaag gaccacggt caccgtctcc | 420 |
| tca | 423 |

<210> SEQ ID NO 109
<211> LENGTH: 384
<212> TYPE: DNA
<213> ORGANISM: Homo sapiens

<400> SEQUENCE: 109

| | |
|---|---|
| atggaagccc cagctcagct tctcttcctc ctgctactct ggctcccaga taccaccgga | 60 |
| gaaattgtgt tgacgcagtc tccaggcacc ctgtctttgt ctccagggga aagagccacc | 120 |
| ctctcctgca gggccagtca gagtgtttac agcagctact tagcctggta ccagcagaaa | 180 |

```
cctggccagg ctcccaggct cctcatctat ggtgcatcca gcagggccac tggcatccca    240
gacaggttca gtggcagtgg gtctgggaca gacttcactc tcaccatcag cagactggag    300
cctgatgatt ttgcagtgta ttactgtcag cactatggtc gctcactcac tttcggcgga    360
gggaccaagg tagagatcaa acga                                           384

<210> SEQ ID NO 110
<211> LENGTH: 429
<212> TYPE: DNA
<213> ORGANISM: Homo sapiens

<400> SEQUENCE: 110
atgaaacacc tgtggttctt cctcctgctg gtggcagctc ccagatgggt cctgtcccag     60
gtgcagctgc aggagtcggg cccaggactg gtgaagcctt cacagaccct gtccctcacc    120
tgcactgtct ctggtggctc catcagcagt ggtggttact actggagctg gatccgccag    180
cacccaggga agggcctgga gtggattggg tacatctatt acagtgggag cacctactac    240
aacccgtccc tcaagagtcg agttaccata tcagtagaca cgtctaagaa ccagttctcc    300
ctgaagctga gctctgtgac tgccgcggac acggccgtgt attactgtgc gagagagaat    360
tacgatattt tgactggttt caactggttc gaccccgggg ccagggaac cctggtcacc     420 gtctcctca                                                            429

<210> SEQ ID NO 111
<211> LENGTH: 381
<212> TYPE: DNA
<213> ORGANISM: Homo sapiens

<400> SEQUENCE: 111
atgagggtcc ctgctcagct cctggggctc ctgctgctct ggttcccagg ttccagatgc     60
gacatccaga tgacccagtc tccatcttcc gtgtctgcat ctgtaggaga cagagtcacc    120
atcacttgtc gggcgagtca gggtattagc agctggttag cctggtatca gcagaaacca    180
gggaaagccc ctaaggtcct gatctattct acatccaggt tgcaaagtgg ggtcccatca    240
aggttcagcg gcagtggatc tgggacagat ttcactctca ccatcagcag tctgcagcct    300
gaagattttg caacttacta ttgtcaacag gctgacagtt tccggacgtt cggccaaggg    360
accaaggtgg aaatcaaacg a                                              381

<210> SEQ ID NO 112
<211> LENGTH: 408
<212> TYPE: DNA
<213> ORGANISM: Homo sapiens

<400> SEQUENCE: 112
tggagttggg ggctgcgctg ggttttcctt gttgctattt tagaaggtgt ccagtgtgag     60
gtgcagttgg tggagtttgg gggaggcctg gtcaagcctg gggggtccct gagactctcc    120
tgtgcagcct ctggattcac cttcagtagt tttaggatga ctgggtccg ccaggctcca    180 ggggaggggc tggagtgggt ctcatccatt actagtagta gtagttacat atactacgca    240
gactcagtga agggccgatt caccatctcc agagacaacg ccaagaactc actgtatctg    300
caaatgaaca gcctgagagc cgaggacacg gctgtgtatt actgtgcgag atttacagct    360
atggcccttg actactgggg ccagggaacc ctggtcaccg tctcctca                 408

<210> SEQ ID NO 113
```

-continued

```
<211> LENGTH: 384
<212> TYPE: DNA
<213> ORGANISM: Homo sapiens

<400> SEQUENCE: 113
atgagggtcc ctgctcagct cctgggactc ctgctgctct ggctcccaga taccagatgt    60
gacatccaga tgacccagtc tccatcctcc ctgtctgcat ctgtaggaga cagagtcacc   120
atcacttgcc gggcgagtca ggcattttc aattatttag cctggtatca gcagaaacca   180
gggaaagttc ctaagctcct gatctatgct gcatccactt tgcaatcagg ggtcccatct   240
cggttcagtg gcagtggatc tgggacagat ttcactctca ccatcagcag tctgcagcct   300
gaagatgttg cagtttatta ctgtctaaag tataacagtg ccccgtggac gttcggccaa   360
gggaccaagg tggaaatcaa acga                                          384

<210> SEQ ID NO 114
<211> LENGTH: 411
<212> TYPE: DNA
<213> ORGANISM: Homo sapiens

<400> SEQUENCE: 114
atgaagcatc tgtggttctt ccttctgctg gtggcagctc ccagatgggt cctgtcccag    60
gtgcagctgc aggagtcggg cccaggactg gtgaagcctt cggagaccct gtccctcacc   120
tgcactgtct ctggtggctc catcagtagt tactactgga gctggatccg gcagcccgcc   180
gggaagggac tggagtggat tgggcgtatc tataccagtg ggagcaccaa ctacaacccc   240
tccctcaaga gtcgagtcac catgtcagta gacacgtcca agaaccagtt ctccctgaag   300
ctgagctctg tgaccgccgc ggacacggcc gtgtattact gtgcgagact tataactgga   360
ccctacggta tggacgtctg gggccaaggg accacggtca ccgtctcctc a            411

<210> SEQ ID NO 115
<211> LENGTH: 384
<212> TYPE: DNA
<213> ORGANISM: Homo sapiens

<400> SEQUENCE: 115
atgagggtcc ctgctcagct cctggggctc ctgctactct ggctccgagg tgccagatgt    60
gacatccaga tgacccagtc tccatcctcc ctgtctgcat ctgtgggaga cagagtcacc   120
atcacttgcc gggcaagtca gagcattagc agctatttaa attggtatca acagaaacca   180
gggaaagccc ctaagctcct gatctatact gcatccaatt tgcgaggtgg ggtcccatca   240
aggttcagtg gcagtggatc tgggacagat ttcactctca ccatcagcgg tctgcaacct   300
gaagattttg caacttacta ctgtcaacag agttacagtt ccctattcac tttcggccct   360
gggaccaaag tggatatcaa acga                                          384

<210> SEQ ID NO 116
<211> LENGTH: 367
<212> TYPE: DNA
<213> ORGANISM: Homo sapiens

<400> SEQUENCE: 116
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactgagtg gattgggtat atctattaca gtgggagcac caactacaac   180
ccctccctca agagtcgagt caccatatca gtagacacgt ccaagaacca gttctccctg   240
```

```
aagctgagct ctgtgaccgc tgcggacacg gccgtgtatt actgtgcgag aaggggtac  300 gacttttga ctggttatga ctactttgac tactggggcc agggaaccct ggtcaccgtc  360
tcctcag                                                          367

<210> SEQ ID NO 117
<211> LENGTH: 325
<212> TYPE: DNA
<213> ORGANISM: Homo sapiens

<400> SEQUENCE: 117
gaaattgtgt tgacgcagtc tccaggcacc ctgtctttgt ctccagggga aagagccacc  60
ctctcctgct gggccagtca gagtgttttc agcaactact tagcctggta ccagcagaaa  120
cctggccagg ctcccaggct cctcatctat ggtgcatcca gcagggccac tggcatccca  180
gacaggttca gtggcagtgg gtctgggaca gacttccctc tcaccatcag cagactggag  240
cctgaagatt ttgcagtgta ttactgtcag cagtatggta gctcaccgct cactttcggc  300
ggagggacca aggtggagat caaac                                      325

<210> SEQ ID NO 118
<211> LENGTH: 361
<212> TYPE: DNA
<213> ORGANISM: Homo sapiens

<400> SEQUENCE: 118
caggtgcagc tgcaggagtc gggcccagga ctggtgaagc cttcggagac cctgtccctc  60
acctgcactg tctctggtgg ctccatcagt agttactact ggagctggat ccggcagccc  120
gccgggaagg gactggagtg gattgggcgt atctatacca gtgggagcac caactacaac  180
ccctccctca gagtcgagt caccatgtca gtagacacgt ccaagaacca gttctccctg  240
aagctgagct ctgtgaccgc cgcggacacg gccgtgtatt actgtgcgag agatgggcag  300
tggctggaag actacggtat ggacgtctgg ggccaaggga ccacggtcac cgtctcctca  360
g                                                                361

<210> SEQ ID NO 119
<211> LENGTH: 325
<212> TYPE: DNA
<213> ORGANISM: Homo sapiens

<400> SEQUENCE: 119
gaaattgtgt tgacgcagtc tccaggcacc ctgtctttgt ctccagggga aagagccacc  60
ctctcctgct gggccagtca gagtgttttc agcaactact tagcctggta ccagcagaaa  120
cctggccagg ctcccaggct cctcatctat ggtgcatcca gcagggccac tggcatccca  180
gacaggttca gtggcagtgg gtctgggaca gacttccctc tcaccatcag cagactggag  240
cctgaagatt ttgcagtgta ttactgtcag cagtatggta gctcaccgct cactttcggc  300
ggagggacca aggtggagat caaac                                      325

<210> SEQ ID NO 120
<211> LENGTH: 21
<212> TYPE: DNA
<213> ORGANISM: Homo sapiens

<400> SEQUENCE: 120
gtacacaccg tgtgctggga c                                           21
```

```
<210> SEQ ID NO 121
<211> LENGTH: 20
<212> TYPE: DNA
<213> ORGANISM: Homo sapiens

<400> SEQUENCE: 121
cctcagatgc ctctggctgg                                                    20

<210> SEQ ID NO 122
<211> LENGTH: 33
<212> TYPE: DNA
<213> ORGANISM: Homo sapiens

<400> SEQUENCE: 122
atattacgtc gacgtacaca ccgtgtgctg gac                                      33

<210> SEQ ID NO 123
<211> LENGTH: 39
<212> TYPE: DNA
<213> ORGANISM: Homo sapiens

<400> SEQUENCE: 123
cagcttagag ctagcccagc agccaggcag gaattcagc                                39

<210> SEQ ID NO 124
<211> LENGTH: 118
<212> TYPE: PRT
<213> ORGANISM: Homo sapiens

<400> SEQUENCE: 124

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Tyr Tyr Tyr Tyr Gly Met Asp Val Trp Gly Gln Gly Thr
            100                 105                 110

Thr Val Thr Val Ser Ser
        115

<210> SEQ ID NO 125
<211> LENGTH: 124
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Gly Glu Leu Trp Ala Gly Tyr Tyr Tyr Tyr Gly Met Asp
                100                 105                 110

Val Trp Gly Gln Gly Thr Thr Val Thr Val Ser Ser
            115                 120

<210> SEQ ID NO 126
<211> LENGTH: 119
<212> TYPE: PRT
<213> ORGANISM: Homo sapiens

<400> SEQUENCE: 126

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Ser Thr Asn Tyr Asn Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Phe Leu Glu Trp Tyr Tyr Tyr Gly Met Asp Val Trp Gly Gln Gly
                100                 105                 110

Thr Thr Val Thr Val Ser Ser
            115

<210> SEQ ID NO 127
<211> LENGTH: 116
<212> TYPE: PRT
<213> ORGANISM: Homo sapiens

<400> SEQUENCE: 127

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Ser Gly
             20                  25                  30

Gly Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Thr Asn Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Met Val Arg Gly Phe Asp Tyr Trp Gly Gln Gly Thr Leu Val
                100                 105                 110

Thr Val Ser Ser
            115
```

<210> SEQ ID NO 128
<211> LENGTH: 120
<212> TYPE: PRT
<213> ORGANISM: Homo sapiens

<400> SEQUENCE: 128

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ile Ser Gly
             20                  25                  30

Gly Tyr Tyr Trp Ser Trp Ile Arg Gln Pro Pro Gly Lys Gly Leu Glu
         35                  40                  45

Trp Ile Gly Tyr Ile Tyr Tyr Ser Gly Ser Asn Tyr Asn Pro Ser
 50                  55                  60

Leu Lys Ser Arg Val Thr Ile Ser Val Asp Ala Ser Lys Asn Gln Phe
 65                  70                  75                  80

Ser Leu Arg Leu Ser Ser Val Thr Ala Ala Asp Thr Ala Val Tyr Tyr
                 85                  90                  95

Cys Ala Arg Ser Met Val Arg Gly Val Ser Phe Asp Tyr Trp Gly Gln
            100                 105                 110

Gly Thr Leu Val Thr Val Ser Ser
        115                 120
```

<210> SEQ ID NO 129
<211> LENGTH: 118
<212> TYPE: PRT
<213> ORGANISM: Homo sapiens

<400> SEQUENCE: 129

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Tyr Tyr Tyr Tyr Gly Met Asp Val Trp Gly Gln Gly Thr Thr
            100                 105                 110

Val Thr Val Ser Ser Ala
        115
```

<210> SEQ ID NO 130
<211> LENGTH: 121
<212> TYPE: PRT
<213> ORGANISM: Homo sapiens

<400> SEQUENCE: 130

```
Gln Val Gln Leu Glu Gln Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
```

```
              35                  40                  45
Ser Ala Ile Ser Gly Ser Gly Gly Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ser Gly Arg Tyr Tyr Tyr Tyr Asp Met Asp Val Trp Gly Gln
                100                 105                 110
Gly Thr Thr Val Thr Val Ser Ser Ala
        115                 120
```

<210> SEQ ID NO 131
<211> LENGTH: 119
<212> TYPE: PRT
<213> ORGANISM: Homo sapiens

<400> SEQUENCE: 131

```
Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
                 20                  25                  30
Gly Tyr Tyr Trp Ser Trp Ile Arg Gln His Pro Gly Lys Gly Leu Glu
             35                  40                  45
Trp Ile Gly Tyr Ile Tyr Tyr Ser Gly Ser Thr Tyr Tyr Asn Pro Ser
 50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Val Tyr Tyr Tyr Tyr Gly Met Asp Val Trp Gly Gln Gly
                100                 105                 110
Thr Thr Val Thr Val Ser Ser
        115
```

<210> SEQ ID NO 132
<211> LENGTH: 121
<212> TYPE: PRT
<213> ORGANISM: Homo sapiens

<400> SEQUENCE: 132

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
                 20                  25                  30
Gly Met His Trp Val Arg Gln Ala Pro Gly Lys Gly Leu Glu Trp Val
             35                  40                  45
Ala Val Ile Ser Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Thr Met Val Arg Gly Tyr Tyr Gly Met Asp Val Trp Gly
                100                 105                 110
Gln Gly Thr Thr Val Thr Val Ser Ser
```

<210> SEQ ID NO 133
<211> LENGTH: 126
<212> TYPE: PRT
<213> ORGANISM: Homo sapiens

<400> SEQUENCE: 133

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Phe Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Ile Thr Met Val Arg Gly Ala Pro Ser Tyr Tyr Gly
            100                 105                 110

Met Asp Val Trp Gly Gln Gly Thr Thr Val Thr Val Ser Ser
        115                 120                 125

<210> SEQ ID NO 134
<211> LENGTH: 116
<212> TYPE: PRT
<213> ORGANISM: Homo sapiens

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Trp Leu Tyr Gly Met Asp Val Trp Gly Gln Gly Thr Thr Val
            100                 105                 110

Thr Val Ser Ser
        115

<210> SEQ ID NO 135
<211> LENGTH: 119
<212> TYPE: PRT
<213> ORGANISM: Homo sapiens

<400> SEQUENCE: 135

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Glu Leu Leu Phe Asp Tyr Trp Gly Gln Gly
            100                 105                 110

Thr Leu Val Thr Val Ser Ser
            115

<210> SEQ ID NO 136
<211> LENGTH: 120
<212> TYPE: PRT
<213> ORGANISM: Homo sapiens

<400> SEQUENCE: 136

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Phe Ala
    50                  55                  60

Val Ser Val Lys Ser Arg Ile Thr Phe Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Glu Leu Leu Gly Phe Asp Tyr Trp Gly Gln
            100                 105                 110

Gly Thr Leu Val Thr Val Ser Ser
            115                 120

<210> SEQ ID NO 137
<211> LENGTH: 120
<212> TYPE: PRT
<213> ORGANISM: Homo sapiens

<400> SEQUENCE: 137

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Phe Ala
    50                  55                  60

Val Ser Val Lys Ser Arg Ile Thr Phe Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp Glu Leu Leu Gly Phe Asp Tyr Trp Gly Gln
            100                 105                 110

```
Gly Thr Leu Val Thr Val Ser Ser
        115                 120

<210> SEQ ID NO 138
<211> LENGTH: 118
<212> TYPE: PRT
<213> ORGANISM: Homo sapiens

<400> SEQUENCE: 138

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Tyr Gly Ser Gly Ser Asp Tyr Trp Gly Gln Gly Thr
            100                 105                 110

Leu Val Thr Val Ser Ser
        115

<210> SEQ ID NO 139
<211> LENGTH: 120
<212> TYPE: PRT
<213> ORGANISM: Homo sapiens

<400> SEQUENCE: 139

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Val Tyr Tyr Tyr Gly Met Asp Val Trp Gly Gln
            100                 105                 110

Gly Thr Thr Val Thr Val Ser Ser
        115                 120

<210> SEQ ID NO 140
<211> LENGTH: 119
<212> TYPE: PRT
<213> ORGANISM: Homo sapiens

<400> SEQUENCE: 140

Gln Val Gln Leu Gln Glu Ser Gly Pro Gly Leu Val Lys Pro Ser Gln
 1               5                  10                  15
```

```
Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
            85                  90                  95

Cys Ala Arg Gly Asn Tyr Tyr Gly Met Asp Val Trp Gly Gln Gly
            100                 105                 110

Thr Thr Val Thr Val Ser Ser
        115
```

<210> SEQ ID NO 141
<211> LENGTH: 114
<212> TYPE: PRT
<213> ORGANISM: Homo sapiens

<400> SEQUENCE: 141

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                   70                  75                  80

Met Glu Leu Ser Arg Leu Arg Ser Asp Asp Thr Ala Val Tyr Tyr Cys
            85                  90                  95

Ala Arg Gly Ala Phe Asp Tyr Trp Gly Gln Gly Thr Leu Val Thr Val
            100                 105                 110

Ser Ser
```

<210> SEQ ID NO 142
<211> LENGTH: 117
<212> TYPE: PRT
<213> ORGANISM: Homo sapiens

<400> SEQUENCE: 142

```
Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                   70                  75                  80

Met Glu Leu Ser Arg Leu Arg Ser Asp Asp Thr Ala Val Phe Tyr Cys
            85                  90                  95

Ala Arg Leu Gly Ala Thr Ser Phe Asp Tyr Trp Gly Gln Gly Thr Leu
```

<210> SEQ ID NO 143
<211> LENGTH: 119
<212> TYPE: PRT
<213> ORGANISM: Homo sapiens

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Asp Ile Leu Thr Gly Tyr Tyr Phe Asp Tyr Trp Gly Gln Gly
            100                 105                 110

Thr Leu Val Thr Val Ser Ser
        115

<210> SEQ ID NO 144
<211> LENGTH: 120
<212> TYPE: PRT
<213> ORGANISM: Homo sapiens

<400> SEQUENCE: 144

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Tyr Asn Tyr Trp Tyr Phe Asp Leu Trp Gly Arg
            100                 105                 110

Gly Thr Leu Val Thr Val Ser Ser
        115                 120

<210> SEQ ID NO 145
<211> LENGTH: 114
<212> TYPE: PRT
<213> ORGANISM: Homo sapiens

<400> SEQUENCE: 145

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
            85                  90                  95

Ala Arg Gly Met Asp Val Trp Gly Gln Gly Thr Thr Val Thr Val Ser
            100                 105                 110

Ser Ala
```

<210> SEQ ID NO 146
<211> LENGTH: 119
<212> TYPE: PRT
<213> ORGANISM: Homo sapiens

<400> SEQUENCE: 146

```
Arg Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                  55                  60

Lys Gly Arg Phe Thr Ile Ser Arg Asp Ser Ala Lys Asn Ser Leu Tyr
 65                  70                  75                  80

Leu Gln Met Asn Ser Leu Arg Asp Glu Asp Thr Ala Val Tyr Tyr Cys
            85                  90                  95

Ala Arg Ser Leu Arg Ser Gly Gly Met Asp Val Trp Gly Gln Gly Thr
            100                 105                 110

Thr Val Thr Val Ser Ser Ala
        115
```

<210> SEQ ID NO 147
<211> LENGTH: 122
<212> TYPE: PRT
<213> ORGANISM: Homo sapiens

<400> SEQUENCE: 147

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
            85                  90                  95
```

```
Cys Ala Arg Tyr Tyr Asp Ile Leu Thr Gly Tyr Gly Met Asp Val Trp
                100                 105                 110

Gly Gln Gly Thr Thr Val Thr Val Ser Ser
            115                 120

<210> SEQ ID NO 148
<211> LENGTH: 113
<212> TYPE: PRT
<213> ORGANISM: Homo sapiens

<400> SEQUENCE: 148

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Phe Asp Tyr Trp Gly Gln Gly Thr Leu Val Thr Val Ser
                100                 105                 110

Ser

<210> SEQ ID NO 149
<211> LENGTH: 121
<212> TYPE: PRT
<213> ORGANISM: Homo sapiens

<400> SEQUENCE: 149

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Trp Phe Gly Glu Leu Tyr Gly Met Asp Val Trp Gly
                100                 105                 110

Gln Gly Thr Thr Val Thr Val Ser Ser
            115                 120

<210> SEQ ID NO 150
<211> LENGTH: 127
<212> TYPE: PRT
<213> ORGANISM: Homo sapiens

<400> SEQUENCE: 150

Gln Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Leu Trp Phe Gly Glu Leu Ser Pro His Tyr
            100                 105                 110

Gly Met Asp Val Trp Gly Gln Gly Thr Thr Val Thr Val Ser Ser
        115                 120                 125

<210> SEQ ID NO 151
<211> LENGTH: 121
<212> TYPE: PRT
<213> ORGANISM: Homo sapiens

<400> SEQUENCE: 151

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Leu Leu Trp Phe Gly Tyr Gly Met Asp Val Trp Gly
            100                 105                 110

Gln Gly Thr Thr Val Thr Val Ser Ser
        115                 120

<210> SEQ ID NO 152
<211> LENGTH: 121
<212> TYPE: PRT
<213> ORGANISM: Homo sapiens

<400> SEQUENCE: 152

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Tyr Tyr Asp Ile Leu Thr Gly Tyr Ala Phe Asp Ile Trp Gly
            100                 105                 110
Gln Gly Thr Met Val Thr Val Ser Ser
        115                 120

<210> SEQ ID NO 153
<211> LENGTH: 125
<212> TYPE: PRT
<213> ORGANISM: Homo sapiens

<400> SEQUENCE: 153

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Ser Tyr Trp Thr Trp Ile Arg Gln His Pro Gly Lys Gly Leu Glu
        35                  40                  45

Trp Ile Gly Tyr Ile Tyr Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Tyr Tyr Asp Ile Leu Thr Gly Tyr Pro Asp Ala Phe
            100                 105                 110

Asp Ile Trp Gly Gln Gly Thr Met Val Thr Val Ser Ser
        115                 120                 125

<210> SEQ ID NO 154
<211> LENGTH: 121
<212> TYPE: PRT
<213> ORGANISM: Homo sapiens

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Ser Tyr Tyr Tyr Tyr Gly Met Asp Val Trp Gly Gln
            100                 105                 110

Gly Thr Thr Val Thr Val Ser Ser Ala
        115                 120

<210> SEQ ID NO 155
<211> LENGTH: 105
<212> TYPE: PRT
<213> ORGANISM: Homo sapiens

<400> SEQUENCE: 155
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Thr Phe
                85                  90                  95

Gly Gly Gly Thr Lys Val Glu Ile Lys
            100                 105
```

<210> SEQ ID NO 156
<211> LENGTH: 108
<212> TYPE: PRT
<213> ORGANISM: Homo sapiens

<400> SEQUENCE: 156

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105
```

<210> SEQ ID NO 157
<211> LENGTH: 110
<212> TYPE: PRT
<213> ORGANISM: Homo sapiens

<400> SEQUENCE: 157

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Thr Phe Gly Gly Gly Thr Lys Val Glu Ile Lys
            100                 105                 110
```

```
<210> SEQ ID NO 158
<211> LENGTH: 105
<212> TYPE: PRT
<213> ORGANISM: Homo sapiens

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Thr Phe
                85                  90                  95

Gly Gly Gly Thr Lys Val Glu Ile Lys
            100                 105

<210> SEQ ID NO 159
<211> LENGTH: 107
<212> TYPE: PRT
<213> ORGANISM: Homo sapiens

<400> SEQUENCE: 159

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Glu Asp Phe Ala Thr Tyr Tyr Cys Leu Gln His Asn Ser Tyr Pro Pro
                    85                  90                  95

Thr Phe Gly Pro Gly Thr Lys Val Asp Ile Lys
                100                 105

<210> SEQ ID NO 161
<211> LENGTH: 114
<212> TYPE: PRT
<213> ORGANISM: Homo sapiens

<400> SEQUENCE: 161

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
                100                 105                 110

Lys Arg

<210> SEQ ID NO 162
<211> LENGTH: 114
<212> TYPE: PRT
<213> ORGANISM: Homo sapiens

<400> SEQUENCE: 162

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val Tyr Ser
            20                  25                  30

Asp Gly Asp Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
                100                 105                 110

Lys Arg

<210> SEQ ID NO 163
<211> LENGTH: 106
<212> TYPE: PRT
<213> ORGANISM: Homo sapiens

<400> SEQUENCE: 163

Glu Ile Val Leu Thr Gln Ser Pro Gly Thr Leu Ser Leu Ser Pro Gly
```

```
                1               5                  10                  15
Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Gly Gln Gly Thr Lys Leu Glu Ile Lys
                100                 105
```

<210> SEQ ID NO 164
<211> LENGTH: 107
<212> TYPE: PRT
<213> ORGANISM: Homo sapiens

<400> SEQUENCE: 164

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Pro Gly Thr Lys Val Asp Ile Lys
                100                 105
```

<210> SEQ ID NO 165
<211> LENGTH: 110
<212> TYPE: PRT
<213> ORGANISM: Homo sapiens

<400> SEQUENCE: 165

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Gly Gln Gly Thr Lys Leu Glu Ile Lys
                100                 105                 110
```

```
<210> SEQ ID NO 166
<211> LENGTH: 107
<212> TYPE: PRT
<213> ORGANISM: Homo sapiens

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 167
<211> LENGTH: 111
<212> TYPE: PRT
<213> ORGANISM: Homo sapiens

<400> SEQUENCE: 167

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Thr Phe Gly Gly Gly Thr Lys Val Glu Ile Lys Arg
            100                 105                 110

<210> SEQ ID NO 168
<211> LENGTH: 113
<212> TYPE: PRT
<213> ORGANISM: Homo sapiens

<400> SEQUENCE: 168

Asp Ile Val Met Thr Gln Thr Pro Leu Ser Ser Pro Val Thr Leu Gly
1               5                   10                  15

Gln Pro Ala Ser Ile Ser Cys Arg Ala Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

Arg

<210> SEQ ID NO 169
<211> LENGTH: 171
<212> TYPE: PRT
<213> ORGANISM: Homo sapiens

<400> SEQUENCE: 169

Val Ser Gly Val Arg Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Ser Arg Tyr Ser Met Asn Trp Val Arg Gln Ala Pro Gly Lys Gly
        35                  40                  45

Leu Glu Trp Val Ser Tyr Ile Ser Ser Ser Ser Thr Ile Tyr Tyr
    50                  55                  60

Ala Asp Ser Val Lys Gly Arg Phe Thr Ile Ser Arg Asp Ser Ala Lys
65                  70                  75                  80

Asn Ser Leu Tyr Leu Gln Met Asn Ser Leu Arg Asp Glu Asp Thr Ala
                85                  90                  95

Val Tyr Tyr Cys Ala Arg Ser Leu Arg Ser Gly Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly
                165                 170

<210> SEQ ID NO 170
<211> LENGTH: 515
<212> TYPE: DNA
<213> ORGANISM: Homo sapiens

<400> SEQUENCE: 170
gtgtccggtg tgagggtgca gctggtggag tctgggggag gcttggtaca gcctgggggg    60
tccctgagac tctcctgtgc agcctctgga ttcaccttca gtagatatag catgaactgg   120
gtccgccagg ctccagggaa ggggctggag tgggtttcat acattagtag tagtagtagt   180
accatatact acgcagactc tgtgaagggc cgattcacca tctccagaga cagtgccaag   240
aactcactgt atctgcaaat gaacagcctg agagacgagg acacggctgt gtattactgt   300
gcgagatcct tacggtccgg cggtatggac gtctggggcc aagggaccac ggtcaccgtc   360
tcctcagcct ccaccaaggg cccatcggtc ttccccctgg cgccctgctc caggagcacc   420
tccgagagca cagcggccct gggctgcctg gtcaaggact acttccccga accggtgacg   480
gtgtcgtgga actcaggcgc tctgaccagc ggcgt                              515

<210> SEQ ID NO 171
<211> LENGTH: 179
```

```
<212> TYPE: PRT
<213> ORGANISM: Homo sapiens

<400> SEQUENCE: 171

Ser Gly Pro Gly Leu Val Lys Pro Ser Glu Thr Leu Ser Leu Thr Cys
 1               5                  10                  15

Thr Val Ser Gly Gly Ser Ile Ser Ser Tyr Tyr Trp Ser Trp Ile Arg
             20                  25                  30

Gln Pro Pro Gly Lys Gly Leu Glu Trp Ile Gly Tyr Ile Tyr Tyr Ser
         35                  40                  45

Gly Ser Thr Asn Tyr Asn Pro Ser Leu Lys Ser Arg Val Thr Ile Ser
     50                  55                  60

Val Asp Thr Ser Lys Asn Gln Phe Ser Leu Lys Leu Thr Ser Val Thr
 65                  70                  75                  80

Ala Ala Asp Thr Ala Val Tyr Tyr Cys Ala Arg Asp Gln His Ser Ser
                 85                  90                  95

Ser Val Tyr Tyr Tyr Tyr Gly Met Asp Val Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly

<210> SEQ ID NO 172
<211> LENGTH: 539
<212> TYPE: DNA
<213> ORGANISM: Homo sapiens

<400> SEQUENCE: 172
tcgggcccag gactggtgaa gccttcggag accctgtccc tcacctgcac tgtctctggt    60
ggctccatca gtagttacta ctggagctgg atccggcagc ccccagggaa gggactggag   120
tggattgggt atatctatta cagtgggagc accaactaca cccctccct caagagtcga   180 gtcaccatat cagtagacac gtccaagaac cagttctccc tgaagctgac ctctgtgacc   240
gctgcggaca cggccgtgta ttactgtgcg agagatcagc atagcagcag cgtttactac   300
tactactacg gtatggacgt ctggggccaa gggaccacgg tcaccgtctc ctcagcctcc   360
accaagggcc catcggtctt ccccctggcg ccctgctcca ggagcacctc cgagagcaca   420
gcggccctgg gctgcctggt caaggactac ttccccgaac cggtgacggt gtcgtggaac   480
tcaggcgctc tgaccagcgg cgtgcacacc ttcccagctg tcctacagtc ctcaggatc    539

<210> SEQ ID NO 173
<211> LENGTH: 173
<212> TYPE: PRT
<213> ORGANISM: Homo sapiens

<400> SEQUENCE: 173

Gln Leu Glu Gln Ser Gly Pro Gly Leu Val Lys Pro Ser Glu Thr Leu
 1               5                  10                  15

Ser Leu Thr Cys Thr Val Ser Asp Gly Ser Ile Ser Ser Ser Tyr
             20                  25                  30
```

```
Tyr Trp Gly Trp Ile Arg Gln Pro Pro Gly Lys Gly Leu Glu Trp Ile
            35                  40                  45

Gly Ser Ile Tyr Tyr Ser Gly Ser Thr Tyr Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Ser Phe Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln
                165                 170
```

<210> SEQ ID NO 174
<211> LENGTH: 519
<212> TYPE: DNA
<213> ORGANISM: Homo sapiens

<400> SEQUENCE: 174

```
cagctggagc agtcgggccc aggactggtg aagccttcgg agaccctgtc cctcacctgc      60
actgtctctg atggctccat cagcagtagt agttactact ggggctggat ccgccagccc     120
ccagggaagg gactggagtg gattgggagt atctattata gtgggagcac ctactacaac     180
ccgtccctca gagtcgagt caccatatcc gtagacacgt ccaagaacca gttctccctg      240
aagctgagct ctgtgaccgc cgcagacacg gctgtgtatt actgtgcgag acacgggtcc     300
ttctttgact actggggcca gggaaccctg gtcaccgtct cctcagcctc caccaagggc     360
ccatcggtct tcccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacag                             519
```

<210> SEQ ID NO 175
<211> LENGTH: 173
<212> TYPE: PRT
<213> ORGANISM: Homo sapiens

<400> SEQUENCE: 175

```
Ala Gln Leu Leu Gly Leu Leu Met Leu Trp Val Pro Gly Ser Ser Gly
1               5                   10                  15

Asp Ile Val Met Thr Gln Thr Pro Leu Ser Ser Pro Val Thr Leu Gly
                20                  25                  30

Gln Pro Ala Ser Ile Ser Cys Arg Ala Ser Gln Ser Leu Val His Ser
            35                  40                  45

Asp Gly Asn Thr Tyr Leu Ser Trp Leu Gln Gln Arg Pro Gly Gln Pro
        50                  55                  60

Pro Arg Leu Leu Ile Tyr Lys Ile Ser Asn Arg Phe Ser Gly Val Pro
65                  70                  75                  80

Asp Arg Phe Ser Gly Ser Gly Ala Gly Thr Asp Phe Thr Leu Lys Ile
                85                  90                  95
```

-continued

```
Ser Arg Val Glu Ala Glu Asp Val Gly Val Tyr Tyr Cys Met Gln Ala
            100                 105                 110

Thr Gln Phe Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn
                165                 170
```

<210> SEQ ID NO 176
<211> LENGTH: 521
<212> TYPE: DNA
<213> ORGANISM: Homo sapiens

<400> SEQUENCE: 176

```
gctcagcttc tggggctgct aatgctctgg gtccctggat ccagtgggga tattgtgatg    60
acccagaccc cactctcctc acctgtcacc cttggacagc cggcctccat ctcctgcagg   120
gctagtcaaa gcctcgtaca cagtgatgga aacacctatt tgagttggct tcagcagagg   180
ccaggccagc ctccaagact cctaatttat aagatttcta accggttctc tggggtccca   240
gacagattca gtggcagtgg ggcagggaca gatttcacac tgaaaatcag cagggtggaa   300
gctgaggatg tcggggttta ttactgcatg caagctacaa atttccgctc actttcggc   360
ggagggacca aggtggagat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg c                       521
```

<210> SEQ ID NO 177
<211> LENGTH: 143
<212> TYPE: PRT
<213> ORGANISM: Homo sapiens

<400> SEQUENCE: 177

```
Glu Thr Gln Leu Thr Gln Ser Pro Gly Thr Leu Ser Leu Ser Pro Gly
 1               5                  10                  15

Glu Arg Ala Thr Leu Ser Cys Arg Ala Ser Gln Ser Ile Tyr Ile Asn
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Glu Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu
    130                 135                 140
```

<210> SEQ ID NO 178

<211> LENGTH: 430
<212> TYPE: DNA
<213> ORGANISM: Homo sapiens

<400> SEQUENCE: 178

```
gaaacgcagc tgacgcagtc tccaggcacc ctgtctttgt ctccagggga aagagccacc      60
ctctcctgca gggccagtca gagtatttac atcaactact tagcctggta ccagcagaaa     120
cctggccagg ctcccaggct cctcatctct ggtgcatcca gcagggccac tggcatccca     180
gacaggttca gtggcagtgg gtctgggaca gacttcactc tcaccatcag cagactggag     240
cctgaggatt ttgcagtgta ttactgtcag cagtatggta ggtcactcac tttcggcgga     300
gggaccgagg tggagatcaa acgaactgtg gctgcaccat ctgtcttcat cttcccgcca     360
tctgatgagc agttgaaatc tggaactgcc tctgttgtgt gcctgctgaa taacttctat     420
cccagagagg                                                            430
```

<210> SEQ ID NO 179
<211> LENGTH: 173
<212> TYPE: PRT
<213> ORGANISM: Homo sapiens

<400> SEQUENCE: 179

```
Leu Leu Gly Leu Leu Met Leu Trp Val Pro Gly Ser Ser Gly Asp Val
 1               5                  10                  15

Val Met Thr Gln Ser Pro Leu Ser Leu Pro Val Thr Leu Gly Gln Pro
            20                  25                  30

Ala Ser Ile Ser Cys Arg Ser Ser Gln Ser Leu Val Tyr Ser Asp Gly
        35                  40                  45

Asp Thr Tyr Leu Asn Trp Phe Gln Gln Arg Pro Gly Gln Ser Pro Arg
    50                  55                  60

Arg Leu Ile Tyr Lys Val Ser Asn Trp Asp Ser Gly Val Pro Asp Arg
65                  70                  75                  80

Phe Ser Gly Ser Gly Ser Gly Thr Asp Phe Thr Leu Lys Ile Ser Arg
                85                  90                  95

Val Glu Ala Glu Asp Val Gly Val Tyr Tyr Cys Met Gln Gly Thr His
            100                 105                 110

Trp Pro Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala
                165                 170
```

<210> SEQ ID NO 180
<211> LENGTH: 519
<212> TYPE: DNA
<213> ORGANISM: Homo sapiens

<400> SEQUENCE: 180

```
ctcctggggc tgctaatgct ctgggtccca ggatccagtg ggatgttgt gatgactcag      60 tctccactct ccctgcccgt cacccttgga cagccggcct ccatctcctg caggtctagt     120
caaagcctcg tatacagtga tggagacacc tacttgaatt ggtttcagca gaggccaggc     180
caatctccaa ggcgcctaat ttataaggtt tctaactggg actctggggt cccagacaga     240
```

```
ttcagcggca gtgggtcagg cactgatttc acactgaaaa tcagcagggt ggaggctgag    300
gatgttgggg tttattactg catgcaaggt acacactggc ctccgctcac tttcggcgga    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                           519
```

<210> SEQ ID NO 181
<211> LENGTH: 367
<212> TYPE: DNA
<213> ORGANISM: Homo sapiens

<400> SEQUENCE: 181

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag aaggggggtac   300 gacttttga ctggttatga ctactttgac tactggggcc agggaaccct ggtcaccgtc    360
tcctcag                                                             367
```

<210> SEQ ID NO 182
<211> LENGTH: 361
<212> TYPE: DNA
<213> ORGANISM: Homo sapiens

<400> SEQUENCE: 182

```
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcgt atctatacca gtgggagcac caactacaac   180
ccctccctca agagtcgagt caccatgtca gtagacacgt ccaagaacca gttctccctg   240
aagctgagct ctgtgaccgc cgcggacacg gccgtgtatt actgtgcgag agatgggcag   300
tggctggaag actacggtat ggacgtctgg ggccaaggga ccacggtcac cgtctcctca   360
g                                                                   361
```

<210> SEQ ID NO 183
<211> LENGTH: 367
<212> TYPE: DNA
<213> ORGANISM: Homo sapiens

<400> SEQUENCE: 183

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag aaggggggtac   300 gatattttga ctggttatga ctactttgac tactggggcc agggaaccct ggtcaccgtc    360
tcctcag                                                             367
```

<210> SEQ ID NO 184
<211> LENGTH: 376

```
<212> TYPE: DNA
<213> ORGANISM: Homo sapiens

<400> SEQUENCE: 184
caggtgcagc tgcaggagtc gggcccagga ctggtgaagc cttcacagac cctgtccctc      60
acctgcactg tctctggtgg ctccatcagc agtggtggtt actactggaa ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgaggacg     300
tattacgata ttttgactgg ttatcccgat gcttttgata tctggggcca agggacaatg     360
gtcaccgtct cttcag                                                      376

<210> SEQ ID NO 185
<211> LENGTH: 370
<212> TYPE: DNA
<213> ORGANISM: Homo sapiens

<400> SEQUENCE: 185
caggtgcagc tggagcagtc gggcccagga ctggtgaagc cttcacagac cctgtccctc      60
acctgcactg tctctggtgg ctccatcagc agtggtggtc gctactggag ctggatccgc     120
cagcacccag ggaagggcct ggagtggatt gggtacatct attacagtgg gagcacctac     180
tacaacccgt ccctcaagag tcgagttacc atatcaatag acacgtctaa gaaccagttc     240
tccctgaagc tgagctctgt gactgccgcg gacacggccg tgtattactg tgcgagagcg     300
gggacttact atggttcggg gagttacctt gactactggg gccagggaac cctggtcacc     360
gtctcctcag                                                             370

<210> SEQ ID NO 186
<211> LENGTH: 370
<212> TYPE: DNA
<213> ORGANISM: Homo sapiens

<400> SEQUENCE: 186
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gggaaatact atggttcggg gagttacctt gactactggg gccagggaac cctggtcacc     360
gtctcctcag                                                             370

<210> SEQ ID NO 187
<211> LENGTH: 376
<212> TYPE: DNA
<213> ORGANISM: Homo sapiens

<400> SEQUENCE: 187
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gaacacctac     180
tacaacccgt ccctcaagag tcgaattacc atatcagtag acacgtctaa gaaccagttc     240
```

```
tccctgaagc tgagctctgt gactgccgcg acacggccg tgtattactg tgcgagaacg      300
tattacgatt ttttgactgg ttaccccgat gcttttgata tctggggcca agggacaatg    360
gtcaccgtct cttcag                                                      376
```

<210> SEQ ID NO 188
<211> LENGTH: 373
<212> TYPE: DNA
<213> ORGANISM: Homo sapiens

<400> SEQUENCE: 188

```
caggtgcagc tggtgcagtc gggggctgag gtgaagaagc ctggggcctc agtgaaggtc     60
tcctgcaagg cttctggata caccttcacc ggctactata tgcactgggt gcgacaggcc   120
cctggacaag gcttgagtg gatgggatgg atcaaccccta acagtggtgg cacaaactat   180
gcacagaagt tcagggcag gtcaccatg accagggaca cgtccatcag cacagcctac    240
atggagctga gcaggctgag atctgacgac acggccgtgt attactgtac gagaggggaa    300
ctgtgggcgg aggggtacta ctactacggt atggacgtct ggggccaagg gaccacggtc    360
accgtctcct cag                                                        373
```

<210> SEQ ID NO 189
<211> LENGTH: 370
<212> TYPE: DNA
<213> ORGANISM: Homo sapiens

<400> SEQUENCE: 189

```
caggtgcagc tgcaggagtc gggcccagga ctggtgaagc cttcacagac cctgtccctc     60
acctgcactg tctctggtgg ctccatcagc agtggtggtt actactggag ctggatccgc   120
cagcacccag ggaagggcct ggagtggatt gggtacatct attacagtgg gaccacctac   180
tacaacccgt ccctcaagag tcgagttacc atatcagtag acacgtctaa gaaccagttc   240
tccctgaagc tgagctctgt gactgccgcg acacggccg tgtattactg tgcgagagta    300
ttactatggt cggggaaga ctacggtgtg gacgtctggg gccaagggac cacggtcacc    360
gtctcctcag                                                            370
```

<210> SEQ ID NO 190
<211> LENGTH: 361
<212> TYPE: DNA
<213> ORGANISM: Homo sapiens

<400> SEQUENCE: 190

```
caggtacagc tgcagcagtc gggtccagga ctggtgaagc cctcgcagac cctctcactc     60
acctgtgcca tctccgggga cagtgtctct agcaacagtg ctgcttggaa ctggatcagg   120
cagtccccat cgagaggcct tgagtggctg gaaggacat actacaggtc caagtggtat    180
aatgattttg cagtatctgt gaaaagtcga ataaccttca acccagacac gtccaagaac    240
cagttctccc tgcagctgaa ctctgtgact cccgaggaca cggctgtgta ttactgtgca    300
agatgggagc tactagggtt tgactactgg ggccaggaa ccctggtcac cgtctcctca    360
g                                                                     361
```

<210> SEQ ID NO 191
<211> LENGTH: 361
<212> TYPE: DNA
<213> ORGANISM: Homo sapiens

<400> SEQUENCE: 191

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagtacctac     180
tacaacccgt ccctcaagag tcgagttacc atatcagtag acacgtctaa gaaccagttc     240
tccctgaagc tgagctctgt gactgccgcg gacacggccg tgtattactg tgcgagagat     300
ggctacaatt actggtactt cgatctctgg ggccgtggca ccctggtcac tgtctcctca     360
g                                                                     361

<210> SEQ ID NO 192
<211> LENGTH: 373
<212> TYPE: DNA
<213> ORGANISM: Homo sapiens

<400> SEQUENCE: 192
caggtgcagc tgcaggagtc gggcccaggc ctggtgaagc cttcggagac cctgtccctc      60
acctgcactg tctctggtgg ctccatcagt agttactact ggagctggat ccggcagccc     120
ccagggaagg gactggagtg gattgggtat atctattcca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agatcagcat     300
agtagcagct tttactacta ctactacggt atggacgtct ggggccaagg gaccacggtc     360
accgtctcct cag                                                        373

<210> SEQ ID NO 193
<211> LENGTH: 361
<212> TYPE: DNA
<213> ORGANISM: Homo sapiens

<400> SEQUENCE: 193
caggtgcagc tgcaggagtc gggcccagga ctggtgaagc cttcggagac cctgtccctc      60
acctgcactg tctctggtgg ctccgtcatc agtggtggtt actactggag ctggatccgg     120
cagcccccag ggaagggact ggagtggatc gggtatatct attatagtgg aagctccaac     180 tacaaccccct ccctcaagag tcgagtcacc atatctgtag acgcgtccaa gaaccagttc    240
tccctgaggc tgagctctgt gaccgctgcg gacacggccg tgtattactg tgcgaggtct     300
atggttcggg gagtatcctt tgactactgg ggccagggaa ccctggtcac cgtctcctca     360
g                                                                     361

<210> SEQ ID NO 194
<211> LENGTH: 382
<212> TYPE: DNA
<213> ORGANISM: Homo sapiens

<400> SEQUENCE: 194
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gtacacctac     180
tacaacccgt ccctcaagag tcgagttacc atatcagtag acacgtctaa gaaccagttc     240
tccctgaagc tgagctctgt gactgccgcg gacacggccg tgtattactg tgcgagagat     300
cggtattacg atatttttgac tggttattat aactacggta tggacgtctg gggccaaggg   360
```

```
accacggtca ccgtctcctc ag                                              382

<210> SEQ ID NO 195
<211> LENGTH: 367
<212> TYPE: DNA
<213> ORGANISM: Homo sapiens

<400> SEQUENCE: 195
caggtgcagc tgcaggagtc gggcccagga ctggtgaagc cttcacagac cctgtccctc      60
acctgcactg tctctggtgg ctccatcagc agtggtgttt actactggag ctggatccgc     120
cagcacccag ggaagggcct ggagtggatt gggtacatct attacagtcg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagaggg     300
aatgcccacg actactactt cggtatggac gtctggggcc aagggaccac ggtcaccgtc     360
tcctcag                                                              367

<210> SEQ ID NO 196
<211> LENGTH: 367
<212> TYPE: DNA
<213> ORGANISM: Homo sapiens

<400> SEQUENCE: 196
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca gagtcgagt caccatatca gtagacacgt ccaagaacca gttctccctg     240
aagctgagct ctgtgaccgc tgcggacacg gccgtgtatt actgtgcgag aaggggtac     300 gatattttga ctggttatga ctactttgac tactggggcc agggaaccct ggtcaccgtc     360
tcctcag                                                              367

<210> SEQ ID NO 197
<211> LENGTH: 376
<212> TYPE: DNA
<213> ORGANISM: Homo sapiens

<400> SEQUENCE: 197
caggtgcagc tgcaggagtc gggcccagga ctggtgaagc cttcacagac cctgtccctc      60
acctgcactg tctctggtgg ctccatcagc agtggtggtt actactggaa ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgaggacg     300
tattacgata ttttgactgg ttatcccgat gcttttgata tctggggcca agggacaatg     360
gtcaccgtct cttcag                                                    376

<210> SEQ ID NO 198
<211> LENGTH: 367
<212> TYPE: DNA
<213> ORGANISM: Homo sapiens

<400> SEQUENCE: 198
caggtgcagc tgcaggagtc gggcccagga ctggtgaagc cttcggagac cctgtccctc      60
acctgcactg tctctggtgg ctccatcagt ttttactact ggaactggat ccggcagccc     120
```

```
gccgggaagg gactggagtg ggttgggcgt atctatacca gtgggagcac caactacaac    180
ccctccctca agagtcgagt caccatgtca gtagacacgt ccaagaacca gttctccctg    240
aagctgagct ctgtgaccgc cgcggacacg gccgtgtatt actgtgcgag agggggtttt    300
ttggagtggg actactacta cggtatggac gtctggggcc aagggaccac ggtcaccgtc    360
tcctcag                                                              367

<210> SEQ ID NO 199
<211> LENGTH: 376
<212> TYPE: DNA
<213> ORGANISM: Homo sapiens

<400> SEQUENCE: 199
caggtgcagc tgcaggagtc gggcccagga ctggtgaagc cttcacagac cctgtccctc     60
acctgcactg tctctggtgg ctccatcagc agtggtggtt cctactggac ctggatccgc    120
cagcacccag ggaagggcct ggagtggatt gggtacatct attacagtgg gaacacctac    180
tacaacccgt ccctcaagag tcgagttacc atatcagtag acacgtctaa gaaccagttc    240
tccctgaagc tgagctctgt gactgccgcg gacacggccg tgtattactg tgcgaggacg    300
tattacgata ttttgactgg ttaccccgat gcttttgata tctggggcca agggacaatg    360
gtcaccgtct cttcag                                                   376

<210> SEQ ID NO 200
<211> LENGTH: 370
<212> TYPE: DNA
<213> ORGANISM: Homo sapiens

<400> SEQUENCE: 200
caggtgcagc tgcaggagtc gggcccagga ctggtgaagc cttcacagac cctggccctc     60
acctgcactg tctccggtgg ctccatcagc agtggtggtt actactggag ctggatccgc    120
cagcacccag ggaagggcct ggagtggatt gggtacatct attacagtgg gtacacctac    180
tacaacccgt ccctcaagag tcgagttacc atatcagtag acacgtctaa gaaccagttc    240
tccctgaagc tgagctctgt gactgccgcg gacacggccg tgtattactg tgcgagagag    300
acagtaactg actactacta ctacggtatg gacgtctggg gccaagggac cacggtcacc    360
gtctcctcag                                                          370

<210> SEQ ID NO 201
<211> LENGTH: 370
<212> TYPE: DNA
<213> ORGANISM: Homo sapiens

<400> SEQUENCE: 201
caggtgcagc tgcaggagtc gggcccagga ctggtgaagc cttcacagac cctgtccctc     60
acctgcactg tctctggtgg ctccatcaac agtggtggtt actactggag ctggatccgc    120
cagcacccag ggaagggcct ggagtggatt gggtacatct attacagtgg gagcacctac    180
tacaacccgt ccctcaagag tcgagttatt atatcagttg acacgtctga gaaccagttc    240
tccctgaagt tgagctctgt gactgccgcg gacacggccg tgtattactg tgcgagagag    300
agggtgactg actactacta ctacggttttg gacgtctggg gccaagggac cacggtcacc    360
gtctcctcag                                                          370

<210> SEQ ID NO 202
```

<211> LENGTH: 361
<212> TYPE: DNA
<213> ORGANISM: Homo sapiens

<400> SEQUENCE: 202
caggtacagc tgcagcagtc gggtccagga ctggtgaagc cctcgcagac cctctcactc    60
acctgtgcca tctccgggga cagtgtctct agcaacagtg ctgcttggaa ctggatcagg   120
cagtccccat cgagaggcct gagtggctg ggaaggacat actacaggtc caagtggtat    180
aatgattttg cagtatctgt gaaaagtcga ataaccttca acccagacac gtccaagaac   240
cagttctccc tgcagctgaa ctctgtgact cccgaggaca cggctgtgta ttactgtgca   300
agatgggagc tactagggtt tgactactgg ggccagggaa ccctggtcac cgtctcctca   360
g                                                                   361

<210> SEQ ID NO 203
<211> LENGTH: 352
<212> TYPE: DNA
<213> ORGANISM: Homo sapiens

<400> SEQUENCE: 203
cagctgcagc tgcaggagtc gggcccagga ctggtgaagc cttcggagac cctgtccctc    60
acctgcactg tctctgatgg ctccatcagc agtagtagtt actactgggg ctggatccgc   120
cagcccccag ggaagggact ggagtggatt gggagtatct attatagtgg gagcacctac   180
tacaacccgt ccctcaagag tcgagtcacc atatccgtag acacgtccaa gaaccagttc   240
tccctgaagc tgagctctgt gaccgccgca gacacggctg tgtattactg tgcgagacac   300
gggtccttct ttgactactg gggccaggga accctggtca ccgtctcctc ag           352

<210> SEQ ID NO 204
<211> LENGTH: 370
<212> TYPE: DNA
<213> ORGANISM: Homo sapiens

<400> SEQUENCE: 204
caggtgcagc tgcaggagtc gggcccagga ctggtgaagc cttcggagac cctgtccctc    60
acctgcactg tctctggtgg ctccatcagt agaaactact ggagctggat ccggcagccc   120
ccagggaagg gactggagtg gattgggtat atctattaca gtgggagcac caagtacaac   180
ccctccctca agagtcgagt caccatatca gtagacacgt ccaagaacca gttctccctg   240
aagctgagct ctgtgaccgc tgcggacacg gccgtatatt actgtgcgcg atcatattac   300
gattttttga ctggttatta tcacgttttt gactactggg gccagggaac cctggtcacc   360
gtctcctcag                                                          370

<210> SEQ ID NO 205
<211> LENGTH: 546
<212> TYPE: DNA
<213> ORGANISM: Homo sapiens

<400> SEQUENCE: 205
caggtgcagc tggagcagtc ggggggaggc ttggtacagc ctgggggtc cctgagactc     60 tcctgtgcag cctctggatt caccttagc agctatgcca tgagctgggt ccgccaggct   120
ccagggaagg ggctggagtg gtctcagct attagtggta gtggtggtgg cacatactac   180
gcagactccg tgaagggccg gttcaccatc tccagagaca attccaagaa cacgctgtat   240
ctgcaaatga acagcctgag agccgaggac acggccgtat attactgtgc cagtgggagg   300

```
tactactact actacgatat ggacgtctgg ggccaaggga ccacggtcac cgtctcctca    360
gcctccacca agggcccatc ggtcttcccc ctggcgccct gctccaggag cacactccga    420
gagcacagcg ccctgggct gcctggtcaa ggactacttc cccgaaccgg tgacggtgtc     480
gtggaactca ggcgctctga ccagcggcgt gcacaccttc ccagctgtcc tacagtcctc    540
aggact                                                               546

<210> SEQ ID NO 206
<211> LENGTH: 361
<212> TYPE: DNA
<213> ORGANISM: Homo sapiens

<400> SEQUENCE: 206
caggtgcagc tgcaggagtc gggcccagga ctggtgaagc cttcggagac cctgtccctc     60
acctgcactg tctctggtgg ctccatcagt agttactact ggagctggat ccggcagccc    120
gccgggaagg gactggagtg gattgggcgt atctatacca gtgggagcac caactacaac    180
ccctccctca agagtcgagt caccatgtca gtagacacgt ccaagaacca gttctccctg    240
aagctgagct ctgtgaccgc cgcggacacg gccgtgtatt actgtgcgag agatgggcag    300
tggctggaag actacggtat ggacgtctgg ggccaaggga ccacggtcac cgtctcctca    360
g                                                                    361

<210> SEQ ID NO 207
<211> LENGTH: 382
<212> TYPE: DNA
<213> ORGANISM: Homo sapiens

<400> SEQUENCE: 207
caggtgcagc tggtggagtc ggggggaggc gtggtccagc ctgggaggtc cctgagactc     60
tcctgtgcag cgtctggatt caccttcagt agctatgcca tgcactgggt ccgccaggct    120
ccaggcaagg gctggagtg gtggcagtt atatggtatg atggaagtac taaatactat      180
gcagactccg tgaagggccg attcaccatc tccagagaca attccaagaa cacgctgtat    240
ctgcaaatga acagcctgag agccgaggac acggctgtgt attactgtgc gagagatcga    300
ggattactat ggttcgggga gttatccccca cactacggta tggacgtctg gggccaaggg    360
accacggtca ccgtctcctc ag                                              382

<210> SEQ ID NO 208
<211> LENGTH: 361
<212> TYPE: DNA
<213> ORGANISM: Homo sapiens

<400> SEQUENCE: 208
caggtgcagc tgcaggagtc gggcccagga ctggtgaagc cttcggagac cctgtccctc     60
acctgcactg tctctggtgg ctccatcagt agtaattact ggagttggat ccggcagccc    120
gccgggaagg gactggagtg gattgggcgt atctatacca gtgggagcac caactacaac    180
ccctccctca agagtcgagt caccatgtca gtagacacgt ccaagaacca gttctccctg    240
aagctgagct ctgtgaccgc cgcggacacg gccgtgtatt actgtgcgag agatcaggga    300
tttttggagt ggttacctct ggacgtctgg ggccaaggga ccacggtcac cgtctcctca    360
g                                                                    361

<210> SEQ ID NO 209
```

<211> LENGTH: 352
<212> TYPE: DNA
<213> ORGANISM: Homo sapiens

<400> SEQUENCE: 209

```
caggtgcagc tggtgcagtc gggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccta acagtggtgg cacaaactat       180
gcacagaagt ttcagggcag ggtcaccatg accaggaca cgtccatcag cacagcctac      240
atggagctga gcaggctgag atctgacgac acggccgtgt tttactgtgc gagactggga     300
gctacctcct tgactactg gggccaggga accctggtca ccgtctcctc ag              352
```

<210> SEQ ID NO 210
<211> LENGTH: 367
<212> TYPE: DNA
<213> ORGANISM: Homo sapiens

<400> SEQUENCE: 210

```
caggtgcagc tgcaggagtc gggcccagga ctggtgaagc cttcggagac cctgtccctc      60
acctgcactg tctctggtgg ctccatcagt ttttactact ggaactggat ccggcagccc     120
gccgggaagg gactgagtg ggttgggcgt atctatacca gtgggagcac caactacaac      180
ccctccctca agagtcgagt caccatgtca gtagacacgt ccaagaacca gttctccctg     240
aagctgagct ctgtgaccgc cgcggacacg gccgtgtatt actgtgcgag aggggttttt    300
ttggagtggg actactacta cggtatggac gtctggggcc aagggaccac ggtcaccgtc     360
tcctcag                                                               367
```

<210> SEQ ID NO 211
<211> LENGTH: 379
<212> TYPE: DNA
<213> ORGANISM: Homo sapiens

<400> SEQUENCE: 211

```
caggtgcagc tggtggagtc ggggggaggc gtggtccagc ctgggaggtc cctgagactc      60
tcctgtgcag cctctggatt caccttcagt agctatggca tgcactgggt ccgccaggct     120
ccaggcaagg gctggagtg ggtggcagtt atatcatatg atggaagtaa taatactat       180
gcagactccg tgaagggccg attcaccttc tccagagaca attccaagaa cacgctgtat     240
ctgcaaatga acagcctgag agctgaggac acggctgtgt attactgtgc gagaagggggt   300
attactatgg ttcggggagc cccctcctac tacggtatgg acgtctgggg ccaagggacc    360
acggtcaccg tctcctcag                                                  379
```

<210> SEQ ID NO 212
<211> LENGTH: 370
<212> TYPE: DNA
<213> ORGANISM: Homo sapiens

<400> SEQUENCE: 212

```
caggtgcagc tgcaggagtc gggcccagga ctggtgaagc cttcacagac cctgtccctc      60
acctgcactg tctctggtgg ctccatcaac agtggtggtt actactggag ctggatccgc     120
cagcacccag ggaagggcct ggagtggatt gggtacatct attacagtgg gagcacctac     180
tacaaccgt ccctcaagag tcgagttatt atatcagttg acacgtctga gaaccagttc      240
tccctgaagt tgagctctgt gactgccgcg gacacggccg tgtattactg tgcgagagag    300
```

```
agggtgactg actactacta ctacggtttg gacgtctggg gccaagggac cacggtcacc    360
gtctcctcag                                                           370
```

<210> SEQ ID NO 213
<211> LENGTH: 322
<212> TYPE: DNA
<213> ORGANISM: Homo sapiens

<400> SEQUENCE: 213

```
gacatccaga tgacccagtc tccatcttcc gtgtctgcat ctgtaggaga cagagtcacc    60
atcacttgtc gggcgagtca gggtattagc agctggttag cctggtttca gcagaaacca   120
gggaaagccc ccaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctatcac cttcggccaa   300
gggacacgac tggagattaa ac                                            322
```

<210> SEQ ID NO 214
<211> LENGTH: 325
<212> TYPE: DNA
<213> ORGANISM: Homo sapiens

<400> SEQUENCE: 214

```
gaaattgtgt tgacgcagtc tccaggcacc ctgtctttgt ctccagggga aagagccacc    60
ctctcctgct gggccagtca gagtgttttc agcaactact tagcctggta ccagcagaaa   120
cctggccagg ctcccaggct cctcatctat ggtgcatcca gcagggccac tggcatccca   180
gacaggttca gtggcagtgg gtctgggaca gacttccctc tcaccatcag cagactggag   240
cctgaagatt ttgcagtgta ttactgtcag cagtatggta gctcaccgct cactttcggc   300
ggagggacca aggtggagat caaac                                         325
```

<210> SEQ ID NO 215
<211> LENGTH: 322
<212> TYPE: DNA
<213> ORGANISM: Homo sapiens

<400> SEQUENCE: 215

```
gacatccaga tgacccagtc tccatcttcc gtgtctgcat ctgtaggaga cagagtcacc    60
atcacttgtc gggcgagtca gggtattagc atctggttaa cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctatcac cttcggccaa   300
gggacacgac tggagattaa ac                                            322
```

<210> SEQ ID NO 216
<211> LENGTH: 322
<212> TYPE: DNA
<213> ORGANISM: Homo sapiens

<400> SEQUENCE: 216

```
gacatccaga tgacccagtc tccatcctcc ctgtctgcat ctgtaggaga cagagtcacc    60
atcacttgcc gggcaagtca ggacattaga aatgatttag ctggtatca gcagaaacca   120 gggaaagccc ctaagcgcct gatctgtgct gcatccagtt tgcaaagtgg ggtcccatca   180
```

```
agtttcagcg gcagtggatc tgggacagaa ttcactctca caatcagcag ccttcagcct    240
gaagattttg caacttatta ctgtctacag cataatagtt acccgtggac gttcggccaa    300
gggaccaagg tggaaatcaa ac                                             322
```

<210> SEQ ID NO 217
<211> LENGTH: 337
<212> TYPE: DNA
<213> ORGANISM: Homo sapiens

<400> SEQUENCE: 217

```
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtgtccacag ctcctgatct atttgggttc taatcgggcc    180
tccggggtcc ctgacaggtt cagtggcagt ggatcaggca cagattttac actgaaaatc    240
agcagagtgg aggctgagga tgttgggggtt tattactgca tgcaagctct acaaactccg    300
ctcactttcg gcggagggac caaggtggag atcaaac                             337
```

<210> SEQ ID NO 218
<211> LENGTH: 337
<212> TYPE: DNA
<213> ORGANISM: Homo sapiens

<400> SEQUENCE: 218

```
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacaa ctcctgatct atttgggttc taatcgggcc    180
tccggggtcc ctgacaggtt cagtggcagt ggatcaggca cagattttac actgaaaatc    240
agcagagtgg aggctgagga tgttgggggtt tattactgca tgcaagctct acaaactccg    300
ctcactttcg gcggagggac caaggtggag atcaaac                             337
```

<210> SEQ ID NO 219
<211> LENGTH: 322
<212> TYPE: DNA
<213> ORGANISM: Homo sapiens

<400> SEQUENCE: 219

```
gacatccaga tgacccagtc tccatcctcc ctgtctgcat ctgtaggaga cagagtcact     60
atcacttgcc gggcaagtca ggccattaga aatgatttag gctggtatca gcagaaaccg    120
gggaaagccc ctaagcgcct gatctatgct gcatccagtt tgcaaagtgg ggtcccatca    180
aggttcagcg gcagtggatc tgggtcagag ttcactctca caatcagcag cctgcagcct    240
gaagattttg caacttatta ctgtctacag tatcatagtt acccgtggac gttcggccaa    300
gggaccaagg tggaaatcaa ac                                             322
```

<210> SEQ ID NO 220
<211> LENGTH: 322
<212> TYPE: DNA
<213> ORGANISM: Homo sapiens

<400> SEQUENCE: 220

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
```

```
gacaggttca gtggcagtgg gtctgggaca gacttcactc tcaccatcag cagactggag    240
cctgaagatt ttgcagtgta ttcctgtcag cagtatggta gctcactcac tttcggcgga    300
gggaccaagg tggagatcaa ac                                             322
```

<210> SEQ ID NO 221
<211> LENGTH: 322
<212> TYPE: DNA
<213> ORGANISM: Homo sapiens

<400> SEQUENCE: 221

```
gacatccaga tgacccagtc tccatcctcc ctgtctgcat ctgtaggaga cagagtcacc     60
atcacttgcc gggcaagtca gagcattacc aactatttaa attggtatca gcagaaacca    120
gggaaagccc ctaagctcct gatctatgct gcatccagct tgcaaagtgg ggtcccatca    180
aggttcagtg gcagtggatc tgggacagat ttcactctca ccatcagcag tctgcaacct    240
gaagattttg caacttacta ctgtcaacag agttacatta cccctctcac tttcggcgga    300
gggaccgagg tggagatcaa ac                                             322
```

<210> SEQ ID NO 222
<211> LENGTH: 322
<212> TYPE: DNA
<213> ORGANISM: Homo sapiens

<400> SEQUENCE: 222

```
gacatccaga tgacccagtc tccatcctcc ctgtctgcat ctgtaggaga cagagtcacc     60
atcacttgcc gggcaagtca gggcattaga tatgatttag ctggtatca gcagaaacca    120 gggaaagccc ctaagcgcct gatctatgct acatccaatt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcccac tttcggccct    300
gggaccaagg tggatatcaa ac                                             322
```

<210> SEQ ID NO 223
<211> LENGTH: 325
<212> TYPE: DNA
<213> ORGANISM: Homo sapiens

<400> SEQUENCE: 223

```
gaaattgtgt tgacgcagtc tccaggcacc ctgtctttgt ctccagggga aagagccacc     60
ctctcctgca gggccagtca gagtgttggc agcagctact tagcctggta ccagcagaaa    120
cctggccaga ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggtt tctcacctct cactttcggc    300
ggagggacca aggtggagat caaac                                          325
```

<210> SEQ ID NO 224
<211> LENGTH: 322
<212> TYPE: DNA
<213> ORGANISM: Homo sapiens

<400> SEQUENCE: 224

```
gacatccaga tgacccagtc tccatcttcc gtgtctgcat ctgtaggaga cagagtcacc     60
atcacttgtc gggcgagtca gggtattagc agctggttag cctggtatca gcagaaacca    120
```

| | | |
|---|---|---|
| gggaaagccc ctaagctcct gatctatgct gcatccagtt tgcaaagtgg ggtcccatca | 180 | |
| aggttcagcg gcagtggatc tgggacagat ttcactctca ccatcagcag cctgcagcct | 240 | |
| gaagattttg caacttacta ttgtcaacag gctaacagtt tccctctcac tttcggccct | 300 | |
| gggaccaaag tggatatcaa ac | 322 | |

<210> SEQ ID NO 225
<211> LENGTH: 322
<212> TYPE: DNA
<213> ORGANISM: Homo sapiens

<400> SEQUENCE: 225

| | |
|---|---|
| gacatccaga tgacccagtc tccatcctcc ctgtctgcat ctgtaggaga cagagtcacc | 60 |
| atcacttgcc gggcaagtca gggcattaga aatgatttag gctggtatca gcagaaacca | 120 |
| gggaaagccc ctaagcgcct gatctatgct gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt acccgctcac tttcggcgga | 300 |
| gggaccaagg tggagatcaa ac | 322 |

<210> SEQ ID NO 226
<211> LENGTH: 322
<212> TYPE: DNA
<213> ORGANISM: Homo sapiens

<400> SEQUENCE: 226

| | |
|---|---|
| gacatccaga tgacccagtc tccatcctcc ctgtctgcat ctgtaggaga cagagtcacc | 60 |
| atcacttgcc gggcaagtca gagcattagc agctatttaa attggtatca gcagaaacca | 120 |
| gggaaagtcc ctaagctcct gatctatgtt gcatccagtt tgcaaagtgg ggtcccatca | 180 |
| aggttcagtg gcagtggatc tgggacagat ttcactctca ccatcagcag tctgcaacct | 240 |
| gaagatttcg caacttacta ctgtcaacag agttacagta ccccgctcac tttcggcgga | 300 |
| gggaccaagg tggagatcaa ac | 322 |

<210> SEQ ID NO 227
<211> LENGTH: 322
<212> TYPE: DNA
<213> ORGANISM: Homo sapiens

<400> SEQUENCE: 227

| | |
|---|---|
| gacatccaga tgacccagtc tccatcctcc ctgtctgcat ctgtaggaga cagagtcacc | 60 |
| atcacttgcc gggcaagtca gagcattagc agctatttaa attggtatca gcagaaacca | 120 |
| gggaaagtcc ctaagctcct gatctatgtt gcatccagtt tgcaaagtgg ggtcccatca | 180 |
| aggttcagtg gcagtggatc tgggacagat ttcactctca ccatcagcag tctgcaacct | 240 |
| gaagatttcg caacttacta ctgtcaacag agttacagta ccccgctcac tttcggcgga | 300 |
| gggaccaagg tggagatcaa ac | 322 |

<210> SEQ ID NO 228
<211> LENGTH: 322
<212> TYPE: DNA
<213> ORGANISM: Homo sapiens

<400> SEQUENCE: 228

| | |
|---|---|
| gacatccaga tgacccagtc tccatcttcc gtgtctgcat ctgtaggaga cagagtcacc | 60 |
| atcacttgtc gggcgagtca gggtattagc atctggttaa cctggtatca gcagaaacca | 120 |

```
gggaaagccc ctaagctcct gatctatgct gcatccagtt tgcaaagtgg ggtcccatca    180
aggttcagcg gcagtggatc tgggacagat tcactctca ccatcagcag cctgcagcct    240
gaagattttg caacttacta ttgtcaacag gctaacagtt ccctatcac cttcggccaa    300 gggacacgac tggagattaa ac                                            322
```

<210> SEQ ID NO 229
<211> LENGTH: 322
<212> TYPE: DNA
<213> ORGANISM: Homo sapiens

<400> SEQUENCE: 229

```
gacatccaga tgacccagtc tccatcctcc ctgtctgcat ctgtaggaga cagagtcacc    60
atcacttgcc gggcaagtca ggacattaga aatgatttag gctggtatca gcagaaacca   120
gggaaagccc ctaagcgcct gatctgtgct gcatccagtt tgcaaagtgg ggtcccatca   180
agtttcagcg gcagtggatc tgggacagaa ttcactctca caatcagcag ccttcagcct   240
gaagattttg caacttatta ctgtctacag cataatagtt acccgtggac gttcggccaa   300
gggaccaagg tggaaatcaa ac                                            322
```

<210> SEQ ID NO 230
<211> LENGTH: 322
<212> TYPE: DNA
<213> ORGANISM: Homo sapiens

<400> SEQUENCE: 230

```
gaaattgtgt tgacgcagtc tccaggcacc ctgtctttgt ctccagggga aagagccacc    60
ctctcctgca gggccagtca gagtgttagc gtcacctact tagcctggta ccagcagaaa   120
cctggccagg ctcccaggct cctcatttat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcggtcac tttcggcgga   300
gggaccaagg tggagatcaa ac                                            322
```

<210> SEQ ID NO 231
<211> LENGTH: 322
<212> TYPE: DNA
<213> ORGANISM: Homo sapiens

<400> SEQUENCE: 231

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag tataaaagtt acccgtggac gttcggccaa   300
gggaccaagg tggaaatcaa ac                                            322
```

<210> SEQ ID NO 232
<211> LENGTH: 322
<212> TYPE: DNA
<213> ORGANISM: Homo sapiens

<400> SEQUENCE: 232

```
gacatccaga tgacccagtc tccatcctcc ctgtctgcat ctgtaggaga cagagtcact    60
```

```
atcacttgcc gggcaagtca ggccattaga aatgatttag gctggtatca gcagaaaccg    120
gggaaagccc ctaagcgcct gatctatgct gcatccagtt tgcaaagtgg ggtcccatca    180
aggttcagcg gcagtggatc tgggtcagag ttcactctca caatcagcag cctgcagcct    240
gaagattttg caacttatta ctgtctacag tatcatagtt acccgtggac gttcggccaa    300
gggaccaagg tggaaatcaa ac                                             322
```

<210> SEQ ID NO 233
<211> LENGTH: 322
<212> TYPE: DNA
<213> ORGANISM: Homo sapiens

<400> SEQUENCE: 233

```
gacatccaga tgacccagtc tccatcctcc ctgtctgcat ctgtaggaga cagagtcacc     60
atcacttgcc gggcaagtca gagcattacc aactatttaa attggtatca gcagaaacca    120
gggaaagccc ctaagctcct gatctatgct gcatccagct tgcaaagtgg ggtcccatca    180
aggttcagtg gcagtggatc tgggacagat ttcactctca ccatcagcag tctgcaacct    240
gaagattttg caacttacta ctgtcaacag agttacatta ccctctcac tttcggcgga    300 gggaccgagg tggagatcaa ac                                             322
```

<210> SEQ ID NO 234
<211> LENGTH: 322
<212> TYPE: DNA
<213> ORGANISM: Homo sapiens

<400> SEQUENCE: 234

```
gacatccaga tgacccagtc tccatcctcc ctgtctgcat ctgtaggaga cagagtcacc     60
atcacttgcc gggcaagtca ggcattaga tatgatttag gctggtatca gcagaaacca    120
gggaaagccc ctaagcgcct gatctatgct acatccaatt tgcaaagtgg ggtcccatca    180
aggttcagcg gcagtggatc tgggacagaa ttcactctca caatcagcag cctgcagcct    240
gaagattttg caacttatta ctgtctacag cataatagtt accctcccac tttcggccct    300
gggaccaagg tggatatcaa ac                                             322
```

<210> SEQ ID NO 235
<211> LENGTH: 322
<212> TYPE: DNA
<213> ORGANISM: Homo sapiens

<400> SEQUENCE: 235

```
gacatccaga tgacccagtc tccatcctcc ctgtctgcat ctgtaggaga cagagtcacc     60
atcacttgcc gggcaagtca ggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagatttta caacttatta ctgtctacag tataaaagtt acccgtggac gttcggccaa    300
gggaccaagg tggaaatcaa ac                                             322
```

<210> SEQ ID NO 236
<211> LENGTH: 328
<212> TYPE: DNA
<213> ORGANISM: Homo sapiens

<400> SEQUENCE: 236

```
gaaattgtgt tgacgcagtc tccaggcacc ctgtctttgt ctccagggga aagagccacc     60
```

|  |  |
|---|---|
| ctctcctgca gggccagtca gagtgtttac agcaactact ttgcctggta ccagcagaaa | 120 |
| cctggccagg ctcccaggct cctcatctat ggtgcatcca gcagggccgc tggcatccca | 180 |
| gacaggttca gtggcagtgg gtctgggaca gacttcactc tcaccatcag cagactggag | 240 |
| cctgaagatt ttgcagtgta ttactgtcag cagtatggta cctcacctcg attcagtttt | 300 |
| ggccagggga ccaagctgga gatcaaac | 328 |

<210> SEQ ID NO 237
<211> LENGTH: 460
<212> TYPE: DNA
<213> ORGANISM: Homo sapiens

<400> SEQUENCE: 237

|  |  |
|---|---|
| gacatcaggc tgacccagtc tccatcctcc ctgtctgcat ctgtaggaga cagagtcacc | 60 |
| atcacttgcc gggcaagtca gggcattaga aatgatttag ctggtatca gcagaaacca | 120 |
| gggaaagccc ctaagcgcct gatctatgct gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt acccgctcac tttcggcgga | 300 |
| gggaccaagg tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgcct | 460 |

<210> SEQ ID NO 238
<211> LENGTH: 322
<212> TYPE: DNA
<213> ORGANISM: Homo sapiens

<400> SEQUENCE: 238

|  |  |
|---|---|
| gacatccaga tgacccagtc tccatcttcc gtgtctgcat ctgtaggaga cagagtcacc | 60 |
| atcacttgtc gggcgagtca gggtattagc agctggttag cctggtttca gcagaaacca | 120 |
| gggaaagccc ccaagctcct gatctatgct gcatccagtt tgcaaagtgg ggtcccatca | 180 |
| aggttcagcg gcagtggatc tgggacagat ttcactctca ccatcagcag cctgcagcct | 240 |
| gaagattttg caacttacta ttgtcaacag gctaacagtt ccctatcac cttcggccaa | 300 |
| gggacacgac tggagattaa ac | 322 |

<210> SEQ ID NO 239
<211> LENGTH: 322
<212> TYPE: DNA
<213> ORGANISM: Homo sapiens

<400> SEQUENCE: 239

|  |  |
|---|---|
| gacatccaga tgacccagtc tccatcctcc ctgtctgcat ctgtgggaga cagagtcacc | 60 |
| atcacttgcc gggcaagtca gggcattaga aatgatttag ctggtatca gcagaaaccg | 120 |
| gggaaagccc ctaagcgcct gatctatgct gcatccagtt tgcaaagtgg ggtcccatca | 180 |
| aggttcagcg gcagtggatc tgggacagat ttcactctca caatcagcag cctgcagcct | 240 |
| gaagattttg caacttatta ctgtctacag cattatagtt acccgctcac tttcggcgga | 300 |
| gggaccaagg tggagatcaa ac | 322 |

<210> SEQ ID NO 240
<211> LENGTH: 325
<212> TYPE: DNA

<213> ORGANISM: Homo sapiens

<400> SEQUENCE: 240

```
gaaattgtgt tgactcagtc tccaggcacc ctgtctttgt ctccagggga aagagccacc    60
ctctcctgca gggccagtca gagtgttagc agctactact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta cctcaccgat caccttcggc   300
caagggacac gactggagat taaac                                         325
```

<210> SEQ ID NO 241
<211> LENGTH: 322
<212> TYPE: DNA
<213> ORGANISM: Homo sapiens

<400> SEQUENCE: 241

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttcctgtcag cagtatggta gctcactcac tttcggcgga   300
gggaccaagg tggagatcaa ac                                            322
```

<210> SEQ ID NO 242
<211> LENGTH: 322
<212> TYPE: DNA
<213> ORGANISM: Homo sapiens

<400> SEQUENCE: 242

```
gaaattgtgt tgacgcagtc tccaggcacc ctgtctttgt ctccagggga aagagccacc    60
ctctcctgca gggccagtca gagtgttagc gtcacctact tagcctggta ccagcagaaa   120
cctggccagg ctcccaggct cctcatttat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcggtcac tttcggcgga   300
gggaccaagg tggagatcaa ac                                            322
```

<210> SEQ ID NO 243
<211> LENGTH: 337
<212> TYPE: DNA
<213> ORGANISM: Homo sapiens

<400> SEQUENCE: 243

```
gatattgtga tgactcagtc tccactctcc ctgcccgtca cccctggaga gccggcctcc    60
atctcctgca ggtctagtca gagcctcctg tatagtaatg gatacaacta tttggattgg   120
tacctgcaga agccagggca gtctccacag ttcctgatct atttgggttc taatcgggcc   180
tccggggtcc ctgacaggtt cagtggcagt ggatcaggca cagatttac actgaaaatc   240
agcagagtgg aggctgagga tgttggggtt tattactgca tgcaagctct acaaactcct   300
cgcagttttg gccaggggac caagctggag atcaaac                            337
```

<210> SEQ ID NO 244
<211> LENGTH: 328

<212> TYPE: DNA
<213> ORGANISM: Homo sapiens

<400> SEQUENCE: 244

```
gaaattgtgt tgacgcagtc tccaggcacc ctgtctttgt ctccagggga aagagccacc     60
ctctcctgca gggccagtca gagtgtttac agcaactact ttgcctggta ccagcagaaa    120
cctggccagg ctcccaggct cctcatctat ggtgcatcca gcagggccgc tggcatccca    180
gacaggttca gtggcagtgg gtctgggaca gacttcactc tcaccatcag cagactggag    240
cctgaagatt ttgcagtgta ttactgtcag cagtatggta cctcacctcg attcagtttt    300
ggccagggga ccaagctgga gatcaaac                                        328
```

<210> SEQ ID NO 245
<211> LENGTH: 153
<212> TYPE: PRT
<213> ORGANISM: Homo sapiens

<400> SEQUENCE: 245

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala
145                 150

<210> SEQ ID NO 246
<211> LENGTH: 182
<212> TYPE: PRT
<213> ORGANISM: Homo sapiens

<400> SEQUENCE: 246

Gln Val Gln Leu Glu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

-continued

```
                85                  90                  95
Ala Ser Gly Arg Tyr Tyr Tyr Tyr Asp Met Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Leu Arg Glu His Ser Gly
        130                 135                 140

Pro Gly Leu Pro Gly Gln Gly Leu Leu Pro Arg Thr Gly Asp Gly Val
145                 150                 155                 160

Val Glu Leu Arg Arg Ser Asp Gln Arg Arg Ala His Leu Pro Ser Cys
                165                 170                 175

Pro Thr Val Leu Arg Thr
                180
```